US008685666B2

(12) United States Patent
Cao

(10) Patent No.: US 8,685,666 B2
(45) Date of Patent: *Apr. 1, 2014

(54) ARL-1 SPECIFIC ANTIBODIES AND USES THEREOF

(75) Inventor: Deliang Cao, Chatham, IL (US)

(73) Assignee: The Board of Trustees of Southern Illinois University, Springfield, IL (US)

( * ) Notice: Subject to any disclaimer, the term of this patent is extended or adjusted under 35 U.S.C. 154(b) by 464 days.

This patent is subject to a terminal disclaimer.

(21) Appl. No.: 13/017,618

(22) Filed: Jan. 31, 2011

(65) Prior Publication Data

US 2011/0195411 A1 Aug. 11, 2011

Related U.S. Application Data

(63) Continuation-in-part of application No. 12/032,327, filed on Feb. 15, 2008, now Pat. No. 8,114,606.

(60) Provisional application No. 60/890,414, filed on Feb. 16, 2007.

(51) Int. Cl.
G01N 33/577 (2006.01)
G01N 33/554 (2006.01)
G01N 33/573 (2006.01)
G01N 33/532 (2006.01)
G01N 33/534 (2006.01)
G01N 33/535 (2006.01)

(52) U.S. Cl.
USPC ......... 435/40.52; 435/7.1; 435/7.4; 435/7.92; 435/25; 435/40.5; 435/40.51; 435/189; 435/960; 436/501; 436/503; 436/504; 436/63; 436/64; 436/804; 436/813

(58) Field of Classification Search
USPC .......... 435/7.1, 7.4, 7.25, 190, 7.92, 25, 40.5, 435/40.51, 40.52, 189, 960; 436/501, 503, 436/504, 63, 64, 804, 813
See application file for complete search history.

(56) References Cited

U.S. PATENT DOCUMENTS

| 4,196,265 A | 4/1980 | Koprowski et al. |
| 4,444,887 A | 4/1984 | Hoffmann |
| 4,612,132 A | 9/1986 | Wollenberg et al. |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,946,778 A | 8/1990 | Ladner et al. |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,331,573 A | 7/1994 | Balaji et al. |
| 5,403,484 A | 4/1995 | Ladner et al. |
| 5,427,908 A | 6/1995 | Dower et al. |
| 5,463,564 A | 10/1995 | Agrafiotis |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,573,905 A | 11/1996 | Lerner et al. |
| 5,580,717 A | 12/1996 | Dower et al. |
| 5,585,089 A | 12/1996 | Queen et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimai et al. |
| 5,780,225 A | 7/1998 | Wigler et al. |
| 5,807,715 A | 9/1998 | Morrison et al. |
| 5,821,047 A | 10/1998 | Garrard et al. |
| 5,880,972 A | 3/1999 | Horlbeck |
| 5,969,108 A | 10/1999 | McCafferty et al. |
| 6,331,415 B1 | 12/2001 | Cabilly et al. |

FOREIGN PATENT DOCUMENTS

| EP | 0 045 665 A1 | 2/1982 |
| EP | 0 239 400 A2 | 9/1987 |
| EP | 0 519 596 A1 | 12/1992 |
| EP | 0 592 106 A1 | 4/1994 |
| WO | WO 86/05807 A1 | 10/1986 |
| WO | WO 89/01036 A1 | 2/1989 |
| WO | WO 90/02809 A1 | 3/1990 |
| WO | WO 91/09967 A1 | 7/1991 |
| WO | WO 91/10737 A1 | 7/1991 |
| WO | WO 91/10741 A1 | 7/1991 |
| WO | WO 92/01047 A1 | 1/1992 |
| WO | WO 92/18619 A1 | 10/1992 |
| WO | WO 92/22324 A1 | 12/1992 |
| WO | WO 93/11236 A1 | 6/1993 |
| WO | WO 95/15982 A2 | 6/1995 |
| WO | WO 95/20401 A1 | 8/1995 |
| WO | WO 96/33735 A1 | 10/1996 |
| WO | WO 96/34096 A1 | 10/1996 |
| WO | WO 98/16654 A1 | 4/1998 |

(Continued)

OTHER PUBLICATIONS

Andrei et al., 1999, Mol Biol Cell, 10: 1463-1475.
Berg, et al., 2004, Radiology 233: 830-849.
Burnside et al., 2005, AJR Am J Roentgeno, 185: 790-796.
Colin et al., 2007, Mol Diagn Ther 11: 355-360.
del Rey et al., 2006, J Biol Chem, 281: 35147-35155.
Dowsett et al., 2006, Ann Oncol 17: 818-826.
Dowsett et al., 2008, J Clin Oncol 26: 1059-1065.
Duffy et al., 2006 Clin Chem 52: 345-351.
Esteva et al., 2004 Breast Cancer Res 6: 109-118.
Ferrari et al., 1997, J Immunol, 159: 1451-1458.

(Continued)

Primary Examiner — Ram R Shukla
Assistant Examiner — Anne Holleran
(74) Attorney, Agent, or Firm — McDonnell Boehnen Hulbert & Berghoff LLP

(57) ABSTRACT

This invention provides antibodies immunologically specific for human ARL-1 (also referred to AKR1B10), a species of the aldo-keto reductase superfamily of proteins. The invention also provides methods of making and methods of using said antibodies.

16 Claims, 30 Drawing Sheets

(56) References Cited

FOREIGN PATENT DOCUMENTS

| | | |
|---|---|---|
| WO | WO 98/24893 A2 | 6/1998 |
| WO | WO 98/46645 A2 | 10/1998 |
| WO | WO 98/50433 A2 | 11/1998 |
| WO | WO 03/046165 | 6/2003 |

OTHER PUBLICATIONS

Ferrari et al., 1997, J Exp Med 185: 579-582.
Girdhani et al., 2005, J Cancer Res ther 1: 129-131.
Hamon et al., 1997 Blood, 90: 2911-2915.
Johansson et al., 2009, Exp Hematol, 37: 969-978.
Kolb et al., 2002, Radiology 225: 165-175.
Levenson et al, 2007 Biochim Biophys Acta 1770: 847-856.
Ling et al., 1998, Kidney Int, 53: 1706-1712.
Ma et al., 2008, J Biol Chem, 283: 3418-3423.
Mariani et al., 2009 Biomakers 14: 130-136.
Mason et al., 1993, biochem J, 296 (Pt 1): 33-39.
Masuda et al., 2009, Cancer Chemother Pharmacol 64: 361-369.
Nickel et al., 2003, Eur J Biochem, 270: 2109-2119.
Pritchard et al., 2008 J Clin Oncol 26: 736-744.
Rodriguez et al., 1997, J Cell Biol 137: 93-104.
Rossi et al., 2003, Mol Cancer Res 1: 707-715.
Sehdev et al., 2009, Curr Oncol 16: S14-23.
Slamon et al., 1987, Science 235: 177-182.
Tan et al., 2008, Cancer 14: 343-351.
Tapper et al., 1990, Biochem J 272: 407-414.
Urruticoechea et al., 2005 J Clin Oncol 23: 7212-7220.
Viktorsson et al., 2005, Adv Cancer Res 94: 143-196.
Wang et al., 2009, J Biol Chem 284: 26742-26748.
Witters et al., 1994, Int J Biochem 26: 589-594.
Yan et al., 2007, Int J Cance, 121: 2301-2306.
Zheng et al., 2007, Endocrinology 148: 2764-2777.
Zhong et al., 2009, Biochem Biophys Res Commun 387: 245-250.
Zu et al., 2007, Taxicol Sci, 97: 562-568.
Mulligan RC & Berg P. Selection for animal cells that express the *Escherichia coli* gene coding for xanthine-guanine phosphoribosyltransferase. Proceedings of the National Academy of Sciences of the United States of America, 1981; vol. 78, No. 4, pp. 2072-2076.
Mulligan RC. The basic science of gene therapy. Science, 1993; vol. 260, No. 5110, pp. 926-932.
Colberre-Garapin F et al. A new dominant hybrid selective marker for higher eukaryotic cells. Journal of Molecular Biology, 1981; vol. 150, No. 1, pp. 1-14.
Crouse GF et al. Expression and amplification of engineered mouse dihydrofolate reductase minigenes. Molecular and Cellular Biology, 1983; vol. 3, No. 2, pp. 257-266.
Proudfoot NJ. Transcriptional interference and termination between duplicated alpha-globin gene constructs suggests a novel mechanism for gene regulation. Nature, 1986; vol. 322, No. 6079, pp. 562-565.
Kohler G. Immunoglobulin chain loss in hybridoma lines. Proceedings of the National Academy of Sciences of the United States of America, 1980; vol. 77, No. 4, pp. 2197-2199.
Veber DF & Freidinger RM. The design of metabolically-stable peptide analogs. Trends in Neuroscience, 1985; vol. 8, pp. 392-396.
Evans BE et al. Design of nonpeptidal ligands for a peptide receptor: cholecystokinin antagonists. Journal of Medicinal Chemistry, 1987; vol. 30, No. 7, pp. 1229-1239.
Merrifield RB. Solid Phase Peptide Synthesis. I. The Synthesis of a Tetrapeptide. Journal of the American Chemical Society, 1963; vol. 85, No. 14, pp. 2149-2154.
Carpino LA. New amino-protecting groups in organic synthesis. Accounts of Chemical Research, 1973; vol. 6, No. 6, pp. 191-198.
Kent SB. Chemical synthesis of peptides and proteins. Annual Review of Biochemistry, 1988; vol. 57, pp. 957-989.
Morley JS. Modulation of the Action of Regulatory Peptides by Structural Modification. Trends in Pharmacological Sciences; vol. 1, pp. 463-468, 1980.
Spatola AF et al. Structure-activity relationships of enkephalins containing serially replaced thiomethylene amide bond surrogates. Life Sciences, 1986; vol. 38, No. 14, pp. 1243-1249.
Hann M et al. On the double bond isostere of the peptide bond: preparation of an enkephalin analogue. Journal of the Chemical Society, Perkin Transactions 1, 1982; pp. 307-314.
Almquist RG et al. Synthesis and biological activity of a ketomethylene analogue of a tripeptide inhibitor of angiotensin converting enzyme. Journal of Medicinal Chemistry, 1980; vol. 23, No. 12, pp. 1392-1398.
Hruby VJ. Conformational restrictions of biologically active peptides via amino acid side chain groups. Life Sciences, 1982; vol. 31, No. 3, pp. 189-199.
McPherson A. Current approaches to macromolecular crystallization. European Journal of Biochemistry, 1990; vol. 189, No. 1, pp. 1-23.
Gallop MA et al. Applications of combinatorial technologies to drug discovery. 1. Background and peptide combinatorial libraries. Journal of Medicinal Chemistry, 1994; vol. 37, No. 9, pp. 1233-1251.
Gordon EM et al. Applications of combinatorial technologies to drug discovery. 2. Combinatorial organic synthesis, library screening strategies, and future directions. Journal of Medicinal Chemistry, 1994; vol. 37, No. 10, pp. 1385-1401.
Ruhland B et al. Solid-Supported Combinatorial Synthesis of Structurally Diverse β-Lactams. Journal of the American Chemical Society, 1996; vol. 118, No. 1, pp. 253-254.
Thompson LA & Ellman JA. Synthesis and Applications of Small Molecule Libraries. Chemical Reviews, 1996; vol. 96, No. 1, pp. 555-600.
Fruchtel JS & Jung G. Organic Chemistry on Solid Supports. Angewandte Chemie International Edition in English, 1996; vol. 35, No. 1, pp. 17-42.
Pavia MR. The Chemical Generation of Molecular Diversity. Network Science Center, www.netsi.org, 1995.
Mjalli AM & Toyonaga BE. Solid Support Combinatorial Chemistry in Lead Discovery and SAR optimization. Network Science Center, www.netsi.org, 1995.
Davies K & Briant C. Combinatorial Chemistry Library Design Using Pharmacophere Diversity. Network Science Center, www.netsi.org, 1995.
Pavia MR. Chemically Generated Screening Libraries: Present and Future. Network Science Center, www.netsi.org, 1996.
Fukumoto S et al. Overexpression of the aldo-keto reductase family protein AKR1B10 is highly correlated with smokers' non-small cell lung carcinomas. Clinical Cancer Research, 2005; vol. 11, No. 5, pp. 1776-1785.
Martinet W et al. Detection of autophagy in tissue by standard immunohistochemistry: possibilities and limitations. Autophagy, 2006; vol. 2, No. 1, pp. 55-57.
Suzuki D et al. Immunohistochemical evidence for an increased oxidative stress and carbonyl modification of proteins in diabetic glomerular lesions. Journal of the American Society of Nephrology, 1999; vol. 10, No. 4, pp. 822-832.
Dake BL et al. Effect of an insulin-like growth factor binding protein fusion protein on thymidine incorporation in neuroblastoma and rhabdomyosarcoma cell lines. Endocrinology, 2004; vol. 145, No. 7, pp. 3369-3374.
Yuan J et al. Cyclin B1 depletion inhibits proliferation and induces apoptosis in human tumor cells. Oncogene, 2004; vol. 23, No. 34, pp. 5843-5852.
Koh JY & Choi DW. Quantitative determination of glutamate mediated cortical neuronal injury in cell culture by lactate dehydrogenase efflux assay. Journal of Neuroscience Methods, 1987; vol. 20, No. 1, pp. 83-90.
Li Y et al. Cleavage of lumican by membrane-type matrix metalloproteinase-1 abrogates this proteoglycan-mediated suppression of tumor cell colony formation in soft agar. Cancer Research, 2004; vol. 64, No. 19, pp. 7058-7064.
Jin JF et al. Preparation and characterization of polyclonal antibodies against ARL-1 protein. World Journal of Gastroenterology, 2003; vol. 9, No. 7, pp. 1455-1459.

(56) References Cited

OTHER PUBLICATIONS

Shan J et al. [Preparation and characterization of monoclonal antibody against ARL-1 protein]. Xi Bao Yu Fen Zi Mian Yi Xue Za Zhi = Chinese Journal of Cellular and Molecular Immunology, 2005; vol. 21, No. 1, pp. 60-63 (abstract).
Martin HJ et al. Purification and characterization of akr1b10 from human liver: role in carbonyl reduction of xenobiotics. Drug Metabolism and Disposition, 2006; vol. 34, No. 3, pp. 464-470.
Hyndman DJ & Flynn TG. Sequence and expression levels in human tissues of a new member of the aldo-keto reductase family. Biochimica et Biophysica Acta, 1998; vol. 1399, No. 2-3, pp. 198-202.
Petrash JM. All in the family: aldose reductase and closely related aldo-keto reductases. Cellular and Molecular Life Sciences, 2004; vol. 61, No. 7-8, pp. 737-749.
Ruther U & Muller-Hill B. Easy identification of cDNA clones. The EMBO Journal, 1983; vol. 2, No. 10, pp. 1791-1794.
Inouye S & Inouye M. Up-promoter mutations in the lpp gene of *Escherichia coli*. Nucleic Acids Research, 1985; vol. 13, No. 9, pp. 3101-3110.
Van Heeke G & Schuster SM. Expression of human asparagine synthetase in *Escherichia coli*. The Journal of Biological Chemistry, 1989; vol. 264, No. 10, pp. 5503-5509.
Logan J & Shenk T. Adenovirus tripartite leader sequence enhances translation of mRNAs late after infection. Proceedings of the National Academy of Sciences of the United States of America, 1984; vol. 81, No. 12, pp. 3655-3659.
Bitter GA et al. Expression and secretion vectors for yeast. Methods in Enzymology, 1987; vol. 153, pp. 516-544.
Szybalska EH & Szybalska W. Genetics of human cell lines, IV. DNA-mediated heritable transformation of a biochemical trait. Proceedings of the National Academy of Sciences of the United States of America, 1962; vol. 48, pp. 2026-2034.
Lowy I et al. Isolation of transforming DNA: cloning the hamster aprt gene. Cell, 1980; vol. 22, No. 3, pp. 817-823.
Wigler M et al. Transformation of mammalian cells with an amplifiable dominant-acting gene. Proceedings of the National Academy of Sciences of the United States of America, 1980; vol. 77, No. 6, pp. 3567-3570.
O'Hare K et al. Transformation of mouse fibroblasts to methotrexate resistance by a recombinant plasmid expressing a prokaryotic dihydrofolate reductase. Proceedings of the National Academy of Sciences of the United States of America, 1981; vol. 78, No. 3, pp. 1527-1531.
Nyska A et al. Glutathione S-transferase pi expression in forestomach carcinogenesis process induced by gavage-administered 2,4-hexadienal in the F344 rat. Archives of Toxicology, 2001; vol. 75, No. 10, pp. 618-624.
Ames BN. Dietary carcinogens and anticarcinogens. Oxygen radicals and degenerative diseases. Science, 1983; vol. 221, No. 4617, pp. 1256-1264.
Davydov VV et al. Possible role of alteration of aldehyde's scavenger enzymes during aging. Experimental Gerontology, 2004; vol. 39, No. 1, pp. 11-16.
De Bont R & van Larebeke N. Endogenous DNA damage in humans: a review of quantitative data. Mutagenesis, 2004; vol. 19, No. 3, pp. 169-185.
Choudhary S et al. Toxicity and detoxification of lipid-derived aldehydes in cultured retinal pigmented epithelial cells. Toxicology and Applied Pharmacology, 2005; vol. 204, No. 2, pp. 122-134.
Persic L et al. An integrated vector system for the eukaryotic expression of antibodies or their fragments after selection from phage display libraries. Gene, 1997; vol. 187, No. 1, pp. 9-18.
Schuler BD & Eder E. Development of a 32P-postlabelling method for the detection of 1,N2-propanodeoxyguanosine adducts of crotonaldehyde in vivo. Archives of Toxicology, 2000; vol. 74, No. 7, pp. 404-414.
Seaman VY et al. A sensitive method for the quantification of acrolein and other volatile carbonyls in ambient air. Analytical Chemistry, 2006; vol. 78, No. 7, pp. 2405-2412.
Uchida K et al. Protein-bound acrolein: potential markers for oxidative stress. Proceedings of the National Academy of Sciences of the United States of America, 1998; vol. 95, No. 9, pp. 4882-4887.
Burton DR & Barbas CF. Human antibodies from combinatorial libraries. Advances in Immunology, 1994; vol. 57, pp. 191-280.
Hashimoto M et al. Structural basis of protein-bound endogenous aldehydes. Chemical and immunochemical characterizations of configurational isomers of a 4-hydroxy-2-nonenal-histidine adduct. The Journal of Biological Chemistry, 2003; vol. 278, No. 7, pp. 5044-5051.
Okada K et al. 4-Hydroxy-2-nonenal-mediated impairment of intracellular proteolysis during oxidative stress. Identification of proteasomes as target molecules. The Journal of Biological Chemistry, 1999; vol. 274, No. 34, pp. 23787-23793.
Uchida K et al. Selective cleavage of thioether linkage in proteins modified with 4-hydroxynonenal. Proceedings of the National Academy of Sciences of the United States of America, 1992; vol. 89, No. 12, pp. 5611-5615.
Yang IY et al. Mutagenesis by acrolein-derived propanodeoxyguanosine adducts in human cells. Biochemistry, 2002; vol. 41, No. 46, pp. 13826-13832.
Mullinax RL et al. Expression of a heterodimeric Fab antibody protein in one cloning step. BioTechniques, 1992; vol. 12, No. 6, pp. 864-869.
Nagy E et al. DNA adduct and tumor formations in rats after intratracheal administration of the urban air pollutant 3-nitrobenzanthrone. Carcinogenesis, 2005; vol. 26, No. 10, pp. 1821-1828.
Cline SD et al. Malondialdehyde adducts in DNA arrest transcription by T7 RNA polymerase and mammalian RNA polymerase II. Proceedings of the National Academy of Sciences of the United States of America, 2004; vol. 101, No. 19, pp. 7275-7280.
Homann N et al. Microbially produced acetaldehyde from ethanol may increase the risk of colon cancer via folate deficiency. International Journal of Cancer, 2000; vol. 86, No. 2, pp. 169-173.
Korenaga D et al. Impaired antioxidant defense system of colonic tissue and cancer development in dextran sulfate sodium-induced colitis in mice. The Journal of Surgical Research, 2002; vol. 102, No. 2, pp. 144-149.
Schaeferhenrich A et al. Human adenoma cells are highly susceptible to the genotoxic action of 4-hydroxy-2-nonenal. Mutation Research, 2003; vol. 526, No. 1-2, pp. 19-32.
Sawai H et al. Direct production of the Fab fragment derived from the sperm immobilizing antibody using polymerase chain reaction and cDNA expression vectors. AJRI, 1995; vol. 34, pp. 26-34.
Salaspuro MP. Alcohol consumption and cancer of the gastrointestinal tract. Best Practice & Research Clinical Gastroenterology, 2003; vol. 17, No. 4, pp. 679-694.
Sladek NE. Human aldehyde dehydrogenases: potential pathological, pharmacological, and toxicological impact. Journal of Biochemical and Molecular Toxicology, 2003; vol. 17, No. 1, pp. 7-23.
Coles BF & Kadluber FF. Detoxification of electrophilic compounds by glutathione S-transferase catalysis: determinants of individual response to chemical carcinogens and chemotherapeutic drugs? Biofactors, 2003; vol. 17, No. 1-4, pp. 115-130.
Sharma R et al. Antioxidant role of glutathione S-transferases: protection against oxidant toxicity and regulation of stress-mediated apoptosis. Antioxidants & Redox Signaling, 2004; vol. 6, No. 2, pp. 289-300.
Cao D et al. Identification and characterization of a novel human aldose reductase-like gene. The Journal of Biological Chemistry, 1998; vol. 273, No. 19, pp. 11429-11435.
Better M et al. *Escherichia coli* secretion of an active chimeric antibody fragment. Science, 1988; vol. 240, No. 4855, pp. 1041-1043.
Huston JS et al. Protein engineering of single-chain Fv analogs and fusion proteins. Methods in Enzymology, 1991; vol. 203, pp. 46-88.
Shu L et al. Secretion of a single-gene-encoded immunoglobulin from myeloma cells. Proceedings of the National Academy of Sciences of the United States of America, 1993; vol. 90, No. 17, pp. 7995-7999.

(56) References Cited

OTHER PUBLICATIONS

Skerra A & Pluckthun A. Assembly of a functional immunoglobulin Fv fragment in *Escherichia coli*. Science, 1988; vol. 240, No. 4855, pp. 1038-1041.

Morrison SL. Transfectomas provide novel chimeric antibodies. Science, 1985; vol. 229, No. 4719, pp. 1202-1207.

Gillies SD et al. High-level expression of chimeric antibodies using adapted cDNA variable region cassettes. Journal of Immunological Methods, 1989; vol. 125, No. 1-2, pp. 191-202.

Riechmann L et al. Reshaping human antibodies for therapy. Nature, 1988; vol. 332, No. 6162, pp. 323-327.

Padlan EA. A possible procedure for reducing the immunogenicity of antibody variable domains while preserving their ligand-binding properties. Molecular Immunology, 1991; vol. 28, No. 4-5, pp. 489-498.

Kohler G & Milstein C. Continuous cultures of fused cells secreting antibody of predefined specificity. Nature, 1975; vol. 256, No. 5517, pp. 495-497.

Kohler G & Milstein C. Derivation of specific antibody-producing tissue culture and tumor lines by cell fusion. European Journal of Immunology, 1976; vol. 6, No. 7, pp. 511-519.

Kohler G et al. Fusion between immunoglobulin-secreting and nonsecreting myeloma cell lines. European Journal of Immunology, 1976; vol. 6, No. 4, pp. 292-295.

Roguska MA et al. Humanization of murine monoclonal antibodies through variable domain resurfacing. Proceedings of the National Academy of Sciences of the United States of America, 1994; vol. 91, No. 3, pp. 969-973.

Jespers LS et al. Guiding the selection of human antibodies from phage display repertoires to a single epitope of an antigen. Bio/Technology, 1994; vol. 12, No. 9, pp. 899-903.

Kutmeier G et al. Assembly of humanized antibody genes from synthetic oligonucleotides using a single-round PCR. BioTechniques, 1994; vol. 17, No. 2, pp. 242-246.

Chothia C et al. Structural determinants in the sequences of immunoglobulin variable domain. Journal of Molecular Biology, 1998; vol. 278, No. 2, pp. 457-479.

Huse WD et al. Generation of a large combinatorial library of the immunoglobulin repertoire in phage lambda. Science, 1989; vol. 246, No. 4935, pp. 1275-1281.

Ward ES et al. Binding activities of a repertoire of single immunoglobulin variable domains secreted from *Escherichia coli*. Nature, 1989; vol. 341, No. 6242, pp. 544-546.

Morrison SL et al. Chimeric human antibody molecules: mouse antigen-binding domains with human constant region domains. Proceedings of the National Academy of Sciences of the United States of America, 1984; vol. 81, No. 21, pp. 6851-6855.

Ames RS et al. Conversion of murine Fabs isolated from a combinatorial phage display library to full length immunoglobulins. Journal of Immunological Methods, 1995; vol. 184, No. 2, pp. 177-186.

Kettleborough CA et al. Isolation of tumor cell-specific single-chain Fv from immunized mice using phage-antibody libraries and the re-construction of whole antibodies from these antibody fragments. European Journal of Immunology, 1994; vol. 24, No. 4, pp. 952-958.

Neuberger MS et al. Recombinant antibodies possessing novel effector functions. Nature, 1984; vol. 312, No. 5995, pp. 604-608.

Takeda S et al. Construction of chimaeric processed immunoglobulin genes containing mouse variable and human constant region sequences. Nature, 1985; vol. 314, No. 6010, pp. 452-454.

Bird RE et al. Single-chain antigen-binding proteins. Science, 1988; vol. 242, No. 4877, pp. 423-426.

Huston JS et al. Protein engineering of antibody binding sites: recovery of specific activity in an anti-digoxin single-chain Fv analogue produced in *Escherichia coli*. Proceedings of the National Academy of Sciences of the United States of America, 1988; vol. 85, No. 16, pp. 5879-5883.

Figure 1A
AKR1B10 Antibody Specificity
1A1  1B1  1B10  1C1  1C2  1C3  1C4
1:1000 1° *anti*-AKR1B10
1:1000 2° *anti*-rabbit IgG
2 µg recombinant protein
1A1  1B1  1B10  1C1  1C2  1C3  1C4
1:1000 1° *anti*-AKR1B10
1:1000 2° *anti*-mouse IgG
2 µg recombinant protein
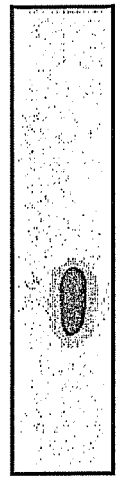
1A1  1B1  1B10  1C1  1C2  1C3  1C4
1:1000 1° *anti*-1B10
1:1000 2° *anti*-rabbit IgG
2 µg recombinant protein

ACTIVITY AND SPECIFICITY OF AKR1B10 ANTIBODY
FIG. 1B) Activity and specificity of AKR1B10 and AR antibodies
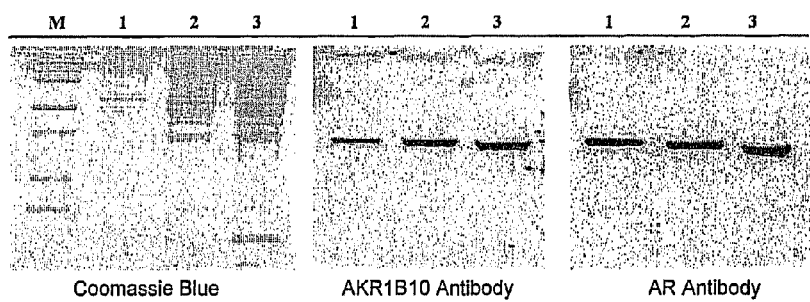
FIG. 1C) Cross-reactivity of AKR1B10 and AR antibodies
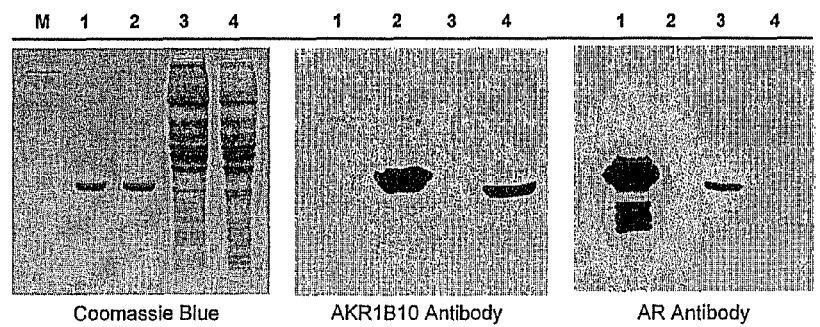

Figures 2A and 2B Cellular distribution of ARL-1 protein in normal column tissues
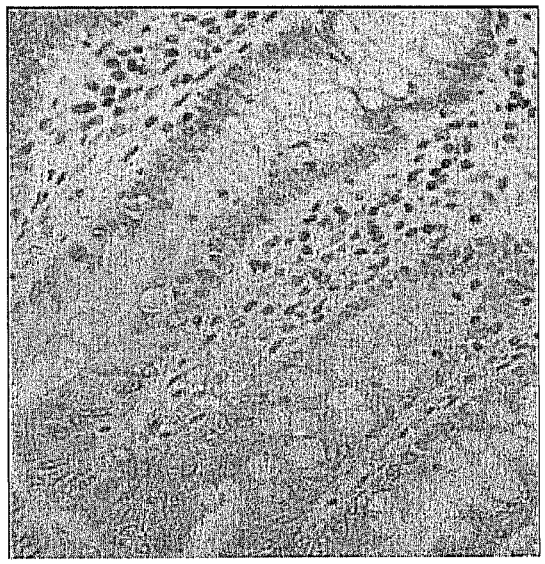
2A
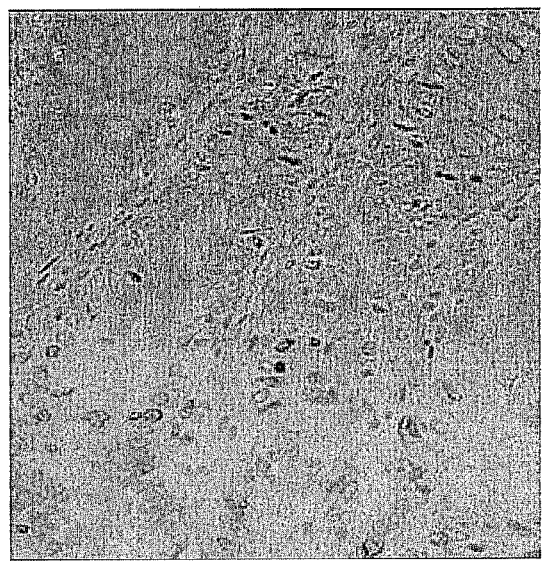
2B A) Clonogenic growth B) Colony formation efficiency

|  | Oligo | Scrambled | siRNA 1 | siRNA 2 |
|---|---|---|---|---|
| Colony formation (%) | 65.7 ± 8.3 | 64.9 ± 5.9 | 47.4 ± 9.7* | 44.75 ± 5.8* |

A) Normal prostate 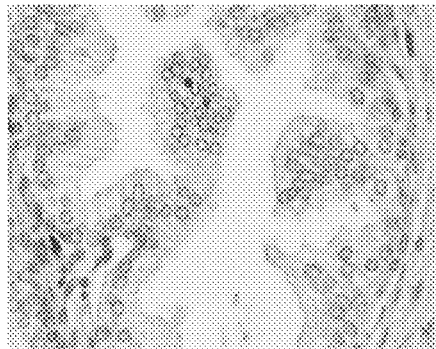 B) Prostate adenocarcinoma 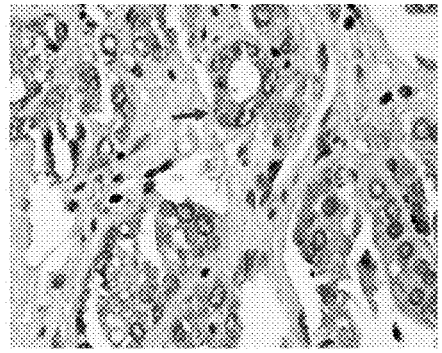
C) Another prostate cancer case 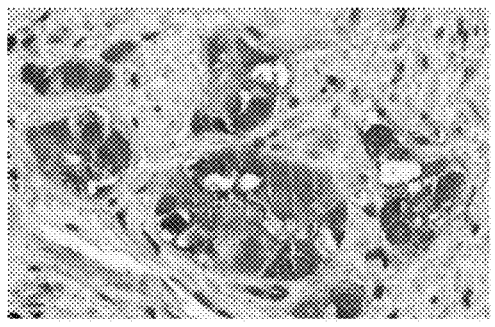 D) Prostate hyperplasia 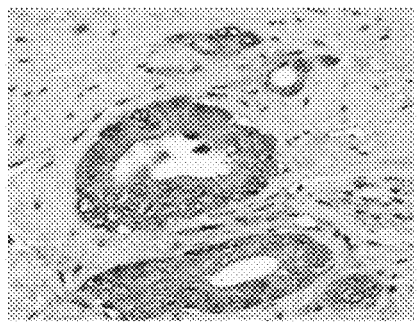
Figure 14

A. hyperplasia of the breast
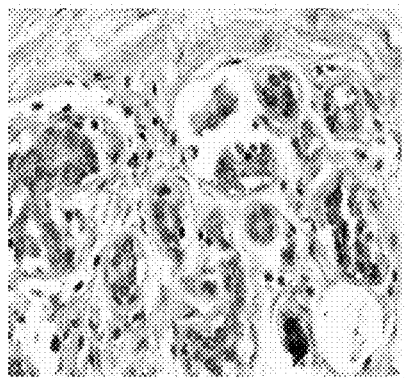
B. ductal carcinoma *in situ*
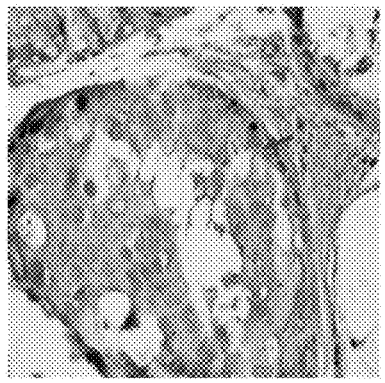
C. recurrent breast cancer
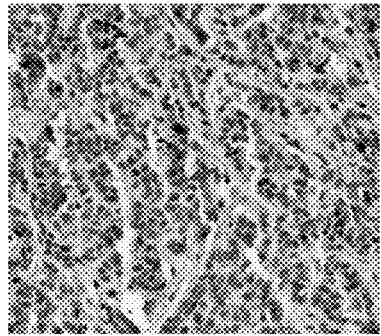
D. metastatic lymph node
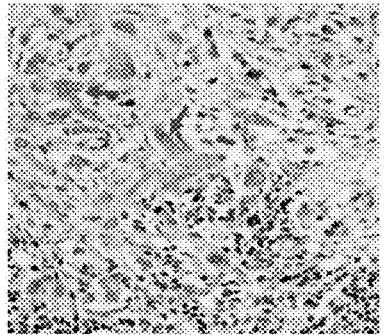
Figure 16

A.

B.

|  | Survival by AKR1B10 expression (%) | | | |
| --- | --- | --- | --- | --- |
|  | 0 | 1 | 2 | 3 |
| *5 year* | 76.47 | 75.76 | 63.24 | 57.83 |
| *10 year* | 52.94 | 45.45 | 41.18 | 32.53 |
| *15 year* | 44.12 | 36.36 | 30.88 | 24.10 |
| *20 year* | 44.12 | 30.30 | 26.47 | 17.99 |

A. Western Blot
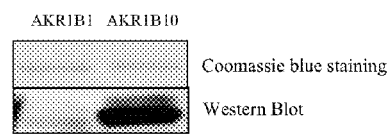
B. Sensitivity and Specificity
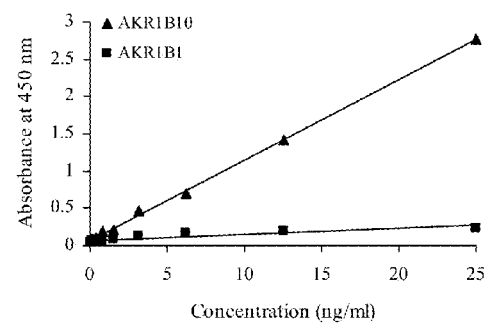
Figure 19

A. Immunohistochemistry
i) Small intestine
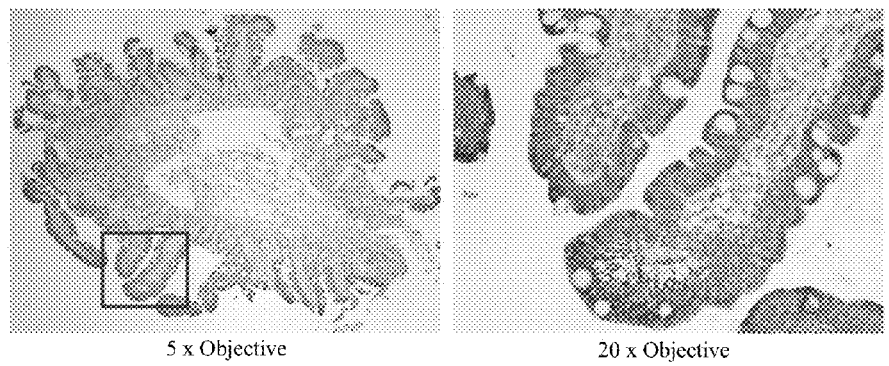
5 x Objective        20 x Objective
ii) Colon
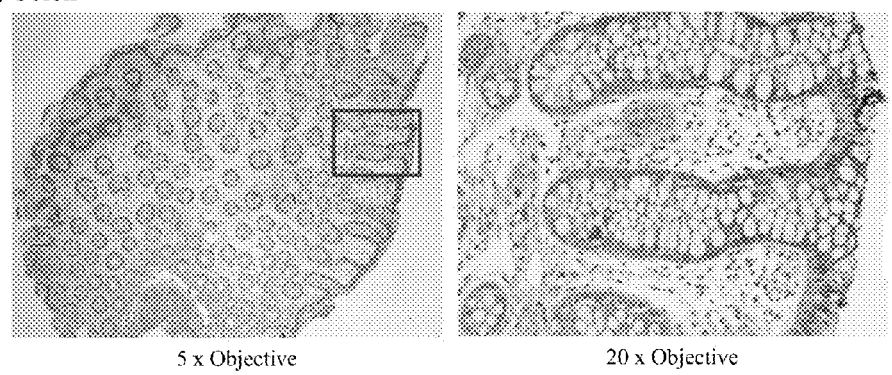
5 x Objective        20 x Objective
B.
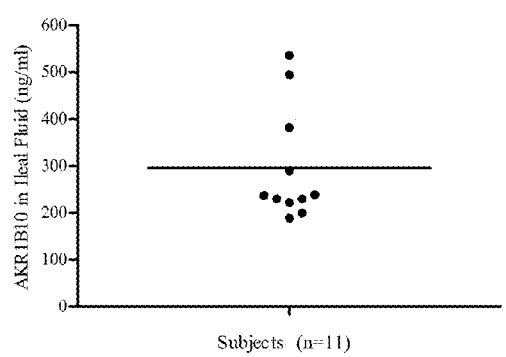
Figure 21

A. Lysosome Isolation
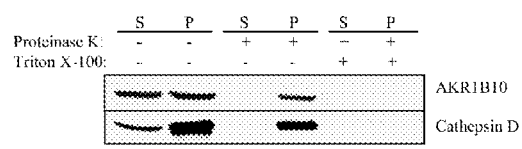
B. Fluorescence Protease Protection
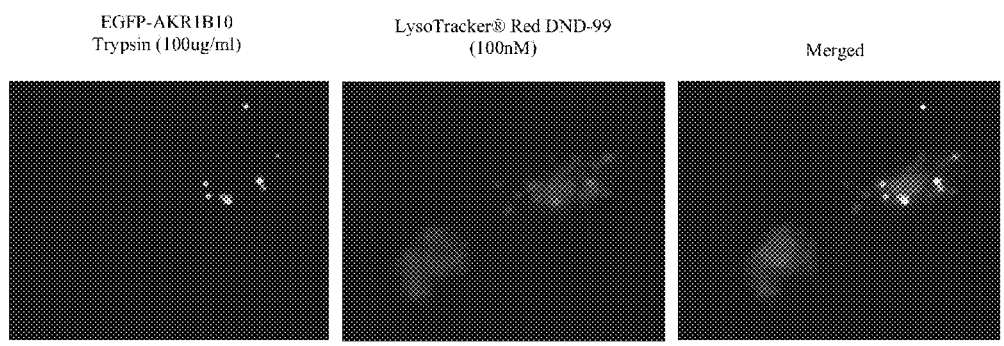
Figure 23

ARL-1 SPECIFIC ANTIBODIES AND USES THEREOF

This application is a continuation-in-part of, and claims the benefit of priority to, U.S. utility patent application Ser. No. 12/032,327, filed Feb. 15, 2008, which relates to and claims priority to U.S. provisional patent application Ser. No. 60/890,414, filed Feb. 16, 2007. The disclosure of each of the above-referenced applications is expressly incorporated by reference herein in its entirety.

This invention was made with government support under grant number W81XWH-09-1-0317 awarded by the U.S. Army Medical Research Acquisition Activity and grant number CA122327 awarded by the National Institutes of Health. The government has certain rights in this invention.

BACKGROUND OF THE INVENTION

1. Field of the Invention

This invention relates to antibodies specific for proteins differentially expressed in normal and tumor or precancerous cells and tissues and methods of use thereof. The invention more specifically relates to antibodies that are immunologically specific for a particular human protein, ARL-1 (also referred to as AKR1B10), a species of protein in the aldo-keto reductase (AKR) superfamily. The invention particularly relates to polyclonal antisera, monoclonal antibodies and fragments and derivatives thereof that are immunologically specific for ARL-1 differentially expressed in normal and tumor or precancerous cells and tissues. Methods for making and using said antibodies are also provided. In specific embodiments, the invention provides methods for detecting ARL-1 using said antibodies for detecting cancer and precancerous lesions, cancer recurrence and cancer metastasis.

2. Summary of the Related Art

Cancer remains one of the leading causes of death in the United States, with colon cancer representing the second leading cause of cancer death, and breast cancer being the leading cause of cancer death in women (Nyska et al., 2001, *Arch Toxicol.* 75: 618-624). It has long been recognized that development of cancer, particularly cancers that occur in later life such as colon cancer, are in part the result of lifelong exposure to environmental carcinogens. Surprisingly, many of these carcinogens are contained in or produced from foods and other natural products. See, Ames, 1983, *Science* 221: 1256-1264

For example, electrophilic carbonyls are constantly produced during metabolism of carbohydrate and lipid (Davydov et al., 2004, *Exp Gerontol.* 39: 11-16; De Bont & van Larebeke, 2004, *Mutagenesis* 19: 169-185; Choudhary et al., 2005, *Toxicol Appl Pharmacol* 204: 122-134, 2005). Carbonyls also widely exist in air, water, and various foodstuffs and beverages (Bowmer & Higgins, 1976, *Arch Environ Contam Toxicol.* 5: 87-96; Schuler & Eder, 2000, *Arch Toxicol.* 74: 404-414; Seaman et al., 2006, *Anal Chem.* 78: 2405-2412). Human exposure to carbonyls occurs in consumption of fruits, vegetables, fish, meat, and alcoholic beverages, such as wine and whisky (Bowmer & Higgins, 1976, Id; Uchida et al., 1998, *Proc Natl Acad Sci USA* 95: 4882-4887). Indeed, carcinogenic methylglyoxal is a constituent of daily consumed coffee, whereas carcinogenic crotonaldehyde is widely present in fruit (5.4-78 µg/kg), vegetables (1.4-100 µg/kg), fish (71.4-1000 µg/kg), meat (10-270 µg/kg), and alcoholic beverages, such as wine (300-700 µg/L) and whisky (30-210 µg/L) (Schuler et al., 2000, *Arch Toxicol.* 74: 404-414.).

Because of their reactivity, carbonyls can interact with free amino and sulfhydryl groups of proteins, peptides and amino acids, forming covalently modified adducts (Davydov et al., 2004, Id.; Vasiliou et al., 2000, *Chem Biol Interact.* 129: 1-19; Hashimoto et al., 2003, *J Biol. Chem.* 278: 5044-5051; Okada et al., 1999, *J Biol. Chem.* 274: 23787-23793; Uchida et al., 1992, *Proc Natl Acad Sci USA,* 89: 5611-5615). These non-specific, covalent modifications may cause protein dysfunction, resistance to intracellular proteolysis, or depolymerization. Protein adducts may also act as secondary messengers, autoantigens, or inhibitors of proteosomes, causing cellular damage and/or autoimmune disorders.

Electrophilic carbonyls can also react with nucleic acids (DNA), forming covalently modified DNA adducts. DNA adducts can block DNA semiconservative replication performed by DNA polymerase, arrest transcription driven by RNA polymerase, and cause DNA mutations and breaks (De Bont & van Larebeke, 2004, Id.; Yang et al., 2002, *Biochemistry* 41: 13826-13832; Hou et al., 1995, *Environ Mol Mutagen* 26: 286-291; Nagy et al., 2005, *Carcinogenesis* 26: 1821-1828; Cline et al., 2004, *Proc Natl Acad Sci USA* 101: 7275-7280, 2004). Documented evidence has indicated the pathogenic effect of carbonyl-derived DNA modifications, resulting in mutagenesis, carcinogenesis, and other age-related diseases (Davydov et al., 2004, Id.; Yang et al., 2002, *Biochemistry* 41: 13826-13832; Nagy et al., 2005, *Carcinogenesis* 26: 1821-1828; Ames, 1983, Id.).

Consequently, electrophilic dietary carbonyls are important pathogens of gastrointestinal (GI) diseases, including neoplasms (Homann et al., 2000, *Int J Cancer* 86: 169-173; Nyska et al., 2001, Id.; Korenaga et al., 2002, *J Surg Res* 102: 144-149; Schaeferhenrich et al., 2003, *Mutat Res.* 526: 19-32). Via food consumption, GI cells are repeatedly exposed to various reactive carbonyls (Ames, 1983, Id.; Fujioka & Shibamoto, 2004, *Lipids* 39: 481-486, 2004). This long-term and cumulative carbonyl exposure, even though minimal in each instance, may eventually cause carcinogenic changes of GI cells after cumulative exposure thereto. Indeed, exposure of F344 rats to 2,4-hexadienal induced stomach hyperplasia, squamous papilloma, and carcinoma, and high levels of malondialdehyde (MDA) in colonic mucosa has been pathogenically related to neoplastic lesions in ulcerative colitis (Korenaga et al., 2002, Id.; Nyska et al., 2001, Id.). In addition, local accumulation of acetaldehyde, microbially produced after alcohol consumption, has been considered a carcinogenic factor for colon and gastric cancers (Homann et al., 2000, Id.; Salaspuro, 2003, *Best Pract Res Clin Gastroenterol.* 17: 679-694).

Nevertheless, little is known of the GI-specific protective mechanisms against carcinogenic lesions induced by dietary carbonyls. Aldehyde dehydrogenase and glutathione-S-transferase (GST) are important enzymes in elimination of intracellular carbonyls by catalyzing carbonyl oxidation to carbonic acids or conjugation with glutathione, but no evidence demonstrates their GI-specificity (Vasiliou et al., 2000, Id.; Sladek, 2003, *J Biochem Mol. Toxicol.* 17: 7-23; Coles & Kadlubar, 2003, *Biofactors* 17: 115-130; Sharma et al., 2004, *Antioxid Redox Signal.* 6: 289-300, 2004).

There is therefore a need in this art to identify endogenous protective mechanisms and proteins involved in such mechanisms. There is further a need in this art to identify whether differential expression of proteins involved in protecting gastrointestinal cells and tissues from the mutagenic and carcinogenic effects of food-related reactive carbonyls provides a marker for cells and tissues at risk for neoplastic transformation and tumor formation, or identifies cells having resistance to anticancer chemotherapeutic drugs, or provides a target for therapeutic and prevention interventions in cancer or precancerous states.

There is also a need in the art to understand the roles of proteins involved in these endogenous protective mechanisms in the tumorigenesis process in other tissues, such as liver, lung, prostate and breast, and for evaluating the clinical relevance of these proteins as markers for cancer in these tissues. Currently, mammography is the only routinely used method for breast cancer screening, with a reported 67.8% sensitivity and 75% specificity for detecting DCIS (ductal carcinoma in situ). However, mammography is costly and the interpretation of results are affected by multiple factors, such as density of breast tissue, experience of radiologists, and volume of tumor cells in a specific location (Berg et al., 2004, *Radiology* 233: 830-849; Burnside et al., 2005, *AJR Am J. Roentgeno*. 185: 790-796). Further, for women undergoing hormone replacement therapy, the sensitivity of mammography for detecting breast cancer can be as low as 25% (Kolb et al., 2002, *Radiology* 225: 165-175).

Currently, estrogen receptor (ER), progesterone receptor (PR) and human epidermal growth factor receptor 2 (HER2) are representatives of therapeutic targets for breast cancer, and targeted therapies of theses markers have significantly improved clinical outcomes of breast cancer (Sehdev et al., 2009, *Curr Oncol* 16: S14-23; Dowsett et al., 2006, *Ann Oncol* 17: 818-826; Slamon et al., 1987, *Science* 235: 177-182; and Dowsett et al., 2008, *J Clin Oncol* 26: 1059-1065). These targeted therapies, however, cannot benefit patients who have triple negative breast cancer (Tan et al., 2008, *Cancer* 14: 343-351). Moreover, the use of these receptor markers for early detection and prognostic prediction is limited (Esteva et al., 2004, *Breast Cancer Res* 6: 109-118). Other biomarkers currently used in breast cancer detection include cancer antigen (CA) 15-3, carcinoembryonic antigen (CEA), ki-67, toposiomerase IIa, and oncotype DX (Duffy et al., 2006, *Clin Chem* 52: 345-351; Levenson et al., 2007, *Biochim Biophys Acta* 1770: 847-856; Urruticoechea et al., 2005, *J Clin Oncol* 23: 7212-7220; Pritchard et al., 2008, *J Clin Oncol* 26: 736-744; Mariani et al., 2009, *Biomarkers* 14: 130-136; and Conlin et al., 2007, *Mol Diagn Ther* 11: 355-360). However, these markers lack sensitivity for early detection and disease-related specificity, and have not been demonstrated as having valid clinical relevance. Therefore, a better marker for detecting cancers, breast cancer in particular, with high sensitivity and specificity is needed.

SUMMARY OF THE INVENTION

This invention provides antibodies and methods of using antibodies that specifically bind to human ARL-1 protein, also referred to as AKR1B10. In certain embodiments, the antibodies comprise polyclonal antisera. In alternative particular embodiments are provided monoclonal antibodies. In particular embodiments, antibodies suitable for use in the invention specifically bind to an epitope defined by an amino acid sequence identified by SEQ ID NO: 1, advantageously produced by immunizing an animal with a peptide having the amino acid sequence as identified by SEQ ID NO: 1. The invention also provides methods for detecting human ARL-1 protein comprising the steps of contacting a sample comprising human ARL-1 protein with an antibody specific for ARL-1 protein and detecting binding of the antibody with the protein. In certain other embodiments, the antibody suitable for use in the present invention is produced by immunizing an animal with the full length ARL-1 protein having the amino acid sequence as identified by SEQ ID NO:5, or an antigenic fragment thereof. In certain advantageous embodiments, the antibodies suitable for use in the present invention comprise a combination of the ARL-1-specific antibodies described above.

ARL-1 expression can be detected in certain normal tissues or certain cancerous tissues, particularly in human gastrointestinal tissues (such as stomach, small intestine or colon), liver, lung, breast, or prostate, using an ARL-1-specific antibody. Thus, the invention provides methods for detecting ARL-1 protein in a normal or cancerous tissue sample, particularly a liver, lung, breast, or prostate tissue sample. ARL-1 protein is detected using methods including but not limited to in situ immunohistochemistry and Western blot analysis. In certain embodiments, ARL-1 expression is detected by using antibodies of the invention produced by immunizing an animal with a peptide having the amino acid sequence as identified by SEQ ID NO:1. In other embodiments, ARL-1 expression is detected by using antibodies produced by immunizing an animal with the full length ARL-1 protein or an antigenic fragment thereof. In certain other embodiments, the antigenic fragment of ARL-1 comprises a peptide having the amino acid sequence of SEQ ID NO:1.

The invention also provides diagnostic methods for identifying a human having breast cancer, breast cancer at early stage or a precancerous lesion of the breast in a breast epithelium tissue sample from a human, using an antibody specific for ARL-1, wherein breast cancer or a precancerous lesion thereof is identified when ARL-1 expression is higher in the breast tissue sample from the human than ARL-1 expression in a control normal breast tissue sample. In certain embodiments, ARL-1 expression is detected by in situ immunohistochemistry. In other embodiments, ARL-1 expression is detected by Western blot analysis.

The invention also provides diagnostic or prognostic methods for identifying a human having prostate cancer, prostate cancer at early stage or a precancerous lesion in a prostate epithelium tissue sample from a human, using an antibody specific for ARL-1 protein, wherein prostate cancer or a precancerous lesion is identified when ARL-1 expression is higher in the prostate tissue sample from the human than ARL-1 expression in a control normal prostate sample. In certain embodiments, ARL-1 expression is detected by in situ immunohistochemistry. In other embodiments, ARL-1 expression is detected by Western blot analysis.

The invention also provides methods for identifying a human at risk for developing breast cancer or prostate cancer using an antibody specific for ARL-1 protein, by identifying increased expression of ARL-1 protein in a non-cancerous human breast tissue sample or by identifying increased expression of ARL-1 protein in a non-cancerous human prostate tissue sample as compared to a normal control breast or normal control prostate tissue sample, respectively. In certain embodiments, ARL-1 expression is detected by in situ immunohistochemistry. In other embodiments, ARL-1 expression is detected by Western blot analysis.

The invention also provides diagnostic or prognostic methods for identifying a human at risk for recurrence of breast cancer or prostate cancer using an antibody specific for ARL-1 protein, by identifying increased expression of ARL-1 protein in a sample from a human who is in remission of breast cancer or prostate cancer, wherein a human at risk for recurrence of breast cancer or prostate cancer is identified when ARL-1 expression in the breast tissue sample or prostate tissue sample from the human in remission of breast cancer or prostate cancer is greater than ARL-1 expression in a control normal breast tissue sample or control normal prostate tissue sample, respectively. In alternative embodiments, a human at risk for recurrence of breast cancer or prostate cancer is identified by detecting increased expression of ARL-1 protein in a sample from a human during remission of breast cancer or prostate cancer as compared to the ARL-1 protein levels in a sample from the same human taken from an earlier time point during remission. In certain embodiments, ARL-1 expression is detected by in situ immunohistochemistry. In other embodiments, ARL-1 expression is detected by Western blot analysis.

ARL-1 expression in tissues can also be assayed by detecting ARL-1 mRNA levels. Thus, the invention provides methods for identifying a human with breast cancer or prostate cancer, or precancerous lesions of the breast or prostate, a human at risk for developing breast or prostate cancer, or a human at risk for recurrence of breast cancer or prostate cancer, comprising the step of identifying increased expression of ARL-1 mRNA in a tissue of the breast or prostate from the human as compared with normal breast or prostate tissue, respectively. In certain embodiments, ARL-1 mRNA is detected by in situ hybridization. In certain other embodiments, ARL-1 mRNA is detected by Northern blot analysis. In other embodiments, ARL-1 mRNA is detected by in vitro amplification, particularly polymerase chain reaction (PCR) and more particularly by reverse transcription-polymerase chain reaction (RT-PCR).

The invention yet further provides methods for detecting expression of human ARL-1 mRNA comprising the steps of hybridizing a nucleic acid sample comprising ARL-1 mRNA with a nucleic acid probe complementary to at least a portion of the nucleotide sequence that encodes the amino acid identified by SEQ ID NO: 1. In other embodiments, nucleic acid probes suitable for use in the present invention comprise an oligonucleotide or polynucleotide complementary to at least a portion of the polynucleotide sequence of SEQ ID NO:4. In certain embodiments, ARL-1 mRNA is detected by in situ hybridization. In other embodiments, ARL-1 mRNA is detected by in vitro amplification, particularly PCR and more particularly by RT-PCR.

It was discovered by the applicant of the instant application that ARL-1 protein can also be detected in a bodily fluid. Accordingly, the invention also provides methods for detecting ARL-1 protein in a bodily fluid. Suitable bodily fluids include without limitation blood plasma, serum, lymph, urine, breast secretion, breast milk, semen, prostate fluid or sputa. Further, the invention provides methods for diagnosing cancer or a precancerous lesion thereof in a human, wherein the cancer is breast cancer, lung cancer, liver cancer, or prostate cancer, comprising the step of identifying a human likely to have cancer or a precancerous lesion thereof by assaying a bodily fluid sample from a human to detect differential amounts or concentrations of ARL-1 protein, wherein the human is identified as likely to have cancer or precancerous lesion thereof when the amounts or concentrations of ARL-1 protein in the bodily fluid sample from the human is greater than the amounts or concentrations of ARL-1 protein in a bodily fluid sample from a normal human, and subjecting the human to further testing to confirm the presence of cancer or precancerous lesion thereof in the human. In certain embodiments, the bodily fluid is blood plasma, serum, lymph, urine, breast secretion, breast milk, semen, prostate fluid or sputa. Suitable further testing is well-known to one skilled in the art, including, without limitation, mammography, and examination of a specific target tissue for changes in gene expression or morphology. In certain particular embodiments, the specific target tissue is a breast, lung, liver or prostate tissue.

In certain embodiments, suitable further testing comprises obtaining a tissue sample from the human for analysis, wherein the tissue sample is a breast tissue, lung tissue, liver tissue or prostate tissue sample. In certain other embodiments, the analysis comprises assaying the tissue sample to detect differential ARL-1 expression, wherein cancer or a precancerous lesion thereof is identified when ARL-1 expression in the tissue sample from the human is greater than ARL-1 expression in a normal tissue sample. In certain other embodiments, suitable further testing comprises obtaining a second bodily fluid, particularly a tissue-specific bodily fluid, for detecting differential ARL-1 expression. In certain particular embodiments, the method for diagnosing cancer or a precancerous lesion thereof in a human comprises the step of detecting the ARL-1 protein levels in urine or serum from a human as compared to the levels of ARL-1 protein in the serum or urine of a control normal human, wherein the human is identified as likely to have cancer or a precancerous lesion thereof when the amounts or concentrations of ARL-1 protein in the bodily fluid sample from the human is greater than the amounts or concentrations of ARL-1 protein in a bodily fluid sample from a control normal human. The method further comprises obtaining a tissue-specific bodily fluid, such as breast milk/secretion, semen or prostate fluid, or sputa, from the human, wherein cancer or a precancerous lesion of the breast, prostate or lung, respectively, is identified when ARL-1 protein expression in the tissue-specific fluid from the human is greater than that from a control normal human. In certain other embodiments, ARL-1 protein is detected by Western blot analysis, radioimmunoassay or enzyme-linked immunosorbent assay (ELISA).

The invention further provides diagnostic or prognostic methods for identifying cancer metastasis or recurrence or identifying a risk for cancer metastasis or recurrence in a human, comprising the step of assaying a bodily fluid sample from a human to detect differential amounts or concentrations of ARL-1 protein, wherein the patient had primary tumor and is in remission of the primary tumor, wherein cancer metastasis or recurrence or the risk for cancer metastasis or recurrence is identified when the amounts or concentrations of ARL-1 protein in the bodily fluid sample from the human is greater than the amounts or concentrations of ARL-1 protein in a control bodily fluid sample from a control normal human, and wherein the cancer is breast cancer, lung cancer, liver cancer or prostate cancer.

In certain embodiments, whether the human has cancer metastasis or recurrence is further determined by subjecting the human to additional testing, including without limitation, examining other symptoms and biopsy samples.

In certain particular embodiments, the invention provides methods for identifying cancer metastasis, comprising the step of assaying a bodily fluid sample from a human having a tumor in a first organ before or after treatment thereof to detect differential amounts or concentrations of ARL-1 protein, wherein cancer metastasis is identified when the amounts or concentrations of ARL-1 protein in the bodily fluid sample from the human are greater than the amounts or concentrations of ARL-1 protein in a control bodily fluid sample from a control normal human. In certain other particular embodiments, the human identified as having or likely to have cancer metastasis previously had primary tumor in a first organ and may have undergone or completed treatments for the primary tumor. More particularly, the human would show normal levels of ARL-1 protein expression in a bodily fluid, as compared with the ARL-1 expression levels of a control normal human, after the treatment for primary tumor and before the development and/or diagnosis of cancer metastasis.

In certain other embodiments, the human identified for having cancer metastasis or likely to have cancer metastasis is subjected to additional testing for the presence of cancer in the proximal or distal site from the primary cancer. Accordingly, in certain particular embodiments, the human identified for having cancer metastasis or likely to have cancer metastasis when the amounts or concentrations of ARL-1 protein in a bodily fluid sample from a second organ from the human are greater than the amounts or concentrations of ARL-1 protein levels in a bodily fluid sample from the second organ from a normal individual. In certain embodiments, the first organ is breast, lung, liver or prostate. In certain other embodiments, the second organ-specific bodily fluid is blood plasma, serum, lymph, urine, breast secretion, breast milk, semen, prostate fluid or sputa. In certain particular embodiments, the human has or previously had breast cancer; and lymph node metastasis of the breast cancer is detected when the ARL-1 protein levels in the lymph of the human are higher as compared to the ARL-1 protein levels in the lymph of a normal individual. In certain other embodiments, ARL-1 protein is detected by Western blot analysis, radioimmunoassay or enzyme-linked immunosorbent assay (ELISA).

In a further aspect, the invention provides methods for treating cancer in a cancer patient comprising the step of administering a treatment to the cancer patient, and assaying a bodily fluid sample from the cancer patient before and after the treatment to detect differential ARL-1 protein amounts or concentrations, wherein the cancer patient continues to receive the treatment when ARL-1 protein amounts or concentrations in the bodily fluid sample from the cancer patient are greater before treatment than ARL-1 protein amounts or concentrations in the bodily fluid sample from the cancer patient after treatment, wherein treatment requires modification when ARL-1 protein amounts or concentrations in the bodily fluid sample from the cancer patient after treatment are no less than ARL-1 protein amounts or concentrations in the bodily fluid sample from the cancer patient before the treatment, and wherein the cancer is breast cancer, lung cancer, liver cancer or prostate cancer. Suitable treatments include without limitation chemotherapy, radiation therapy and hormone therapy. In certain embodiments, the treatment comprises chemotherapy. In certain other embodiments, the treatment comprises radiotherapy. In yet other embodiments, the bodily fluid is blood plasma, serum, lymph, urine, breast secretion, breast milk, semen, prostate fluid or sputa. In certain other embodiments, ARL-1 protein is detected by Western blot analysis, radioimmunoassay or enzyme-linked immunosorbent assay (ELISA).

In yet another aspect, the invention provides uses of a reagent for detecting breast cancer or prostate cancer or a precancerous lesion of the breast or prostate in a human, wherein the breast cancer or prostate cancer or a precancerous lesion thereof is identified when ARL-1 expression in the breast or prostate tissue sample from the human is greater than ARL-1 expression in a normal breast tissue sample or a normal prostate tissue sample. In another aspect, the invention provides uses of a reagent for determining the risk of developing a breast cancer or prostate cancer in a human, wherein the risk is identified when ARL-1 expression in the breast or prostate tissue sample from the human is greater than ARL-1 expression in a normal breast tissue sample or a normal prostate tissue sample. In yet another aspect, the invention provides uses of a reagent for determining the risk of recurrence of a breast cancer or prostate cancer in a human who is in remission of breast or prostate cancer, wherein the risk is identified when ARL-1 expression in the breast or prostate tissue sample from the human is greater than ARL-1 expression in a normal breast tissue sample or a normal prostate tissue sample.

In a further aspect, the invention provides uses of a reagent for diagnosing cancer or a precancerous lesion thereof in a human, wherein the cancer is breast cancer, prostate cancer, lung cancer, or liver cancer, and wherein the human is identified as likely to have cancer or precancerous lesion thereof when the amounts or concentrations of ARL-1 protein in a bodily fluid sample from the human is greater than the amounts or concentrations of ARL-1 protein levels in a bodily fluid sample from a normal individual.

In another aspect, the invention provides uses of a reagent for identifying cancer metastasis or recurrence or a risk of cancer metastasis or recurrence in a human, wherein the human is in remission of a primary cancer, wherein the cancer is breast cancer, prostate cancer, lung cancer, or liver cancer, and wherein cancer metastasis or recurrence or the risk of cancer metastasis or recurrence is identified when the amounts or concentrations of ARL-1 protein in a bodily fluid sample from the human is greater than the amounts or concentrations of ARL-1 protein levels in a bodily fluid sample from a normal individual. In yet another aspect, the invention provides uses of a reagent for identifying cancer metastasis or a risk of cancer metastasis in a human, wherein the human had primary cancer in a first organ before treatment thereof, wherein the cancer is breast cancer, prostate cancer, lung cancer, or liver cancer, and wherein cancer metastasis or the risk of cancer metastasis is detected when the amounts or concentrations of ARL-1 protein in a bodily fluid sample from a second organ from the human is greater than the amounts or concentrations of ARL-1 protein levels in a bodily fluid sample from the second organ from a normal individual. In certain embodiments, the first organ is breast, lung, liver or prostate. In certain other embodiments, the second organ-specific bodily fluid is lymph, breast secretion, breast milk, semen, prostate fluid or sputa.

Suitable reagent for use in the instant invention comprises ARL-1 specific reagents, including without limitation one or more oligonucleotide probes specific for the ARL-1 gene or one or more antibodies or antigen-binding fragments thereof that specifically bind to human ARL-1 protein; in some particular embodiments, the one or more antibodies or antigen-binding fragments thereof comprise an antibody produced by immunizing an animal using a peptide antigen with the amino acid sequence identified by SEQ ID NO:1. An ordinary artisan would understand that both oligonucleotide probes and antibodies or antigen-binding fragments thereof can be used to detect ARL-1 expression in a tissue sample; and antibodies or antigen-binding fragments thereof can be used to detect ARL-1 protein level in a bodily fluid sample.

In a further aspect, the invention provides uses of pharmaceutical compositions for treating cancer in a cancer patient, wherein the cancer is breast cancer, prostate cancer, lung cancer, or liver cancer, and wherein the patient continues to receive the treatment when the amounts or concentrations of ARL-1 protein in a bodily fluid sample from the cancer patient before the treatment are greater than the amounts or concentrations of ARL-1 protein in a bodily fluid sample from the cancer patient after the treatment, and wherein the treatment requires modification when the amounts or concentrations of ARL-1 protein in a bodily fluid sample from the cancer patient before the treatment are equal to or less than the amounts or concentrations of ARL-1 protein in a bodily fluid sample from the cancer patient after the treatment.

The invention also provides kits for the practice of the diagnostic and prognostic methods of the invention, comprising preparations of the detection reagents of the invention in one or more containers and instructions for use. In certain embodiments, detection reagents comprise ARL-1 specific antibodies. In other embodiments, detection reagents comprise nucleic acid probes specific for detecting ARL-1 mRNA. In certain other embodiments, detection reagents comprise oligonucleotide PCR primers specific for ARL-1 mRNA for PCR-mediated amplification and probes specific for detection of ARL-1 mRNA. In certain embodiments, kits also contain reagents, such as reagents for immunohistochemistry, Western blot analysis, ELISA, radioimmunoassay, in situ hybridization, or Northern blot analysis, useful in the practice of the methods of the invention. In certain other embodiments, the kits further comprise a control sample.

The invention advantageously provides a better cancer marker with improved sensitivity and disease-related specificity, particularly a bodily fluid cancer marker that allows non-invasive detection of cancer or a precancerous lesion thereof, cancer recurrence and metastasis. In certain particular embodiments, the cancer is breast cancer.

Specific preferred embodiments of the present invention will become evident from the following more detailed description of certain preferred embodiments and the claims.

BRIEF DESCRIPTION OF THE DRAWINGS

FIG. 1A shows the results of Western blot analysis of several members of the aldo-keto reductase (AKR) superfamily detected using polyclonal antisera as provided herein and two alternative antibody preparations. 2.0 μg of purified protein were electrophoresed per lane.

FIG. 1B shows the results of Coomassie blue staining and Western blot analysis of cell lysates from increasing numbers (Lane 2: 10,000; Lane 3: 50,000; Lane 4: 100,000) of A549 cells, which express both AR and ARL-1 (AKR1B10); Lane M contains size marker. Western blots are probed with anti-AR antibodies and anti-ARL-1 antibodies according to the invention.

FIG. 1C shows the results of Western blot analysis of purified AR (Lane 1) and ARL-1 (AKR1B10; Lane 2) protein probed with AR and ARL-1 (AKR1B10) antibodies; also shown are whole cell lysates from 293T cells (that express AR; Lane 3) and HCT-8 cells (that express ARL-1; Lane 4). Lane M contains size marker.

FIGS. 2A and 2B are photomicrographs (20× objective) showing ARL-1 expression in normal colon. Adjacent paraffin sections of a normal colon tissue were assayed by immunohistochemistry as described in Example 3. FIG. 2A demonstrates that the ARL-1 protein is specifically expressed in mature epithelial cells of the colon, as indicated by Ki-67, a protein marker of proliferating cells shown in FIG. 2B. Ki-67 positive cells are mainly located in the crypts.

FIG. 7B), and thymidine incorporation assessment (FIG. 7D). Cells for growth rate assays were collected by trypsinization at indicated time points and viable cells were counted by trypan blue staining Western blot, enzymatic activity, and thymidine incorporation into DNA were performed 72 hours after siRNA delivery. For thymidine incorporation, HCT-8 cells were pulsed with [$^3$H]-thymidine for 2 hours before harvest using a rubber policeman. Acidic insoluble nucleic acids were precipitated by 15% trichloroacetic acid and radioactivity measured by scintillation counter and corrected with protein amounts. All values represent mean±SD from three independent measurements. * denotes statistical significance ($P<0.05$ or $P<0.01$, if two asterisks), compared to control.

FIGS. 14 A-D are photomicrographs of immunohistochemistry of normal prostate tissue, prostate cancer tissue or prostate tissues with precancerous lesions stained with an AKR1B10-specific antibody as described in Example 2. Images show that AKR1B10 (ARL-1) was overexpressed in a prostate adenocarcinoma (FIG. 14B, arrow) (20× objective).

FIGS. 16A-D are photomicrographs of immunohistochemistry stained with ARL-1 antibody (arrows) in breast tissues of hyperplasia (FIG. 16A) ductal carcinoma in situ (DCIS) (FIG. 16B), recurrent breast cancer (FIG. 16C) and metastatic lymph node (FIG. 16D).

FIG. 19A shows photographs of Western blot analyses using capture anti-AKR1B10 polyclonal antibodies generated in a goat using the whole AKR1B10 (ARL-1) protein as an immunogen. FIG. 19B shows a graph demonstrating sensitivity and specificity of sandwich ELISA using detection polyclonal antibodies described in Example 2 and capture polyclonal antibodies. Purified AKR1B1 or AKR1B10 protein at concentrations of 0, 0.098, 0.195, 0.391, 0.781, 1.5625, 3.125, 6.25, 12.5, and 25 ng/ml was used as standards.

FIG. 21A shows immunohistochemical staining of AKR1B10 (ARL-1) of tissue sections of small intestine and colon from healthy individuals. FIG. 21B shows expression levels of AKR1B10 (ARL-1) in ileal fluids from normal healthy individuals.

FIGS. 23A-23B show results demonstrating that AKR1B10 (ARL-1) was secreted via the lysosome-mediated pathway. FIG. 23A shows photographs of Western blot analysis demonstrating that AKR1B10 was present in the lysosomal fraction protected from proteinase K digestion, and pretreatment with Triton X-100 destroyed lysosomal membrane and abolished protection from proteinase K digestion (S-supernatant; P-pellet). FIG. 23B shows photomicrographs of fluorescence protease protection assay. The left panel shows signals of GFP in the presence of trypsin (100 μg/ml); the middle panel shows signals of LYSOTRACKER® RedDND-00 (100 nM); and the right panel shows the merged image where cell nuclei was stained with Hoechst. Protease-protected EGFP-AKR1B10 (ARL-1) protein was co-localized with lysosome staining.

DETAILED DESCRIPTION OF THE PREFERRED EMBODIMENTS

Figure 3:
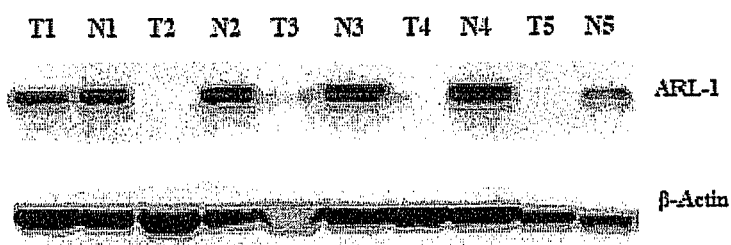
FIG. 3 is a photograph of Western blot analysis of ARL-1 protein in normal and colon cancer samples. Soluble proteins (50 μg each) isolated from normal and cancer colon tissues were used for Western blot using ARL-1 specific antibody of the invention. ARL-1 protein was not detectable in Tumor 2, 4 and 5 and dramatically reduced in Tumor 3. T, tumor; N, Normal.

This invention provides antibodies specific for ARL-1 protein and methods of using thereof. Suitable antibodies for use in the present invention include polyclonal antisera, monoclonal antibodies and fragments and derivatives thereof, that are immunologically specific for a particular member of the aldo-keto reductase (AKR) superfamily of proteins. This member, aldose reductase-like-1 (ARL-1, also designated aldo-keto reductase family 1 B10, AKR1B10) is a protein recently identified by the inventor that is overexpressed in hepatocellular carcinoma (GenBank Accession No. U37100 as described in Cao et al., 1998, *J Biol. Chem.* 273: 11429-11435, 1998, which is incorporated herein by reference in its entirety). When expressed recombinantly, this protein showed strong enzymatic activity with a range of carbonyls. As shown herein, the expression and cellular distribution of ARL-1 protein in the gastrointestinal tract, an organ with high frequency of malignant disease, and its enzymatic activity and kinetic constants in relation to acrolein and crotonaldehyde, two highly mutagenic and carcinogenic carbonyls with wide dietary distributions, indicated that ARL-1 is a marker for gastrointestinal cancer cells and precancerous cells. These results were supported further by the effect of cellular ARL-1 activity on cell viability, clonogenic growth, and response to extra carbonyl stress. The results disclosed herein showed that ARL-1 is an important protein that protects gastrointestinal cells from dietary carbonyl carcinogenic lesions and a marker for gastrointestinal precancerous and cancer cells, and cells resistant to certain anticancer chemotherapeutic drugs.

The ARL-1 protein is related by amino acid sequence to other members of the aldo-keto reductase (AKR) superfamily of proteins. The term ARL-1 is used interchangeably with AKR1B10 throughout this application. The full-length polynucleotide and amino acid sequences of ARL-1 are identified by SEQ ID NOs: 4 and 5, respectively. These sequences set forth in SEQ ID NOs: 4 and 5 are identical to the sequences under GenBank Accession No. U37100, based on Cao et al., 1998, *J Biol. Chem.* 273: 11429-11435, 1998, which is incorporated herein by reference in its entirety. The sequences under U37100 were publicly available since 1998 and to the best of the applicant's knowledge have not been changed up to the filing date of this application.

Despite the close sequence relationship between the members of this superfamily of proteins (Cao et al., 1998, Id.), the inventor has found a peptide antigen derived from the ARL-1 amino acid sequence capable of being used to produce antibodies as defined herein having specificity for ARL-1 and that do not cross-react with other members of the superfamily. This peptide antigen is identified by the sequence:

DDKGNAIGGKATFLC (SEQ ID NO. 1).

It will be understood in the art that this peptide forms an epitope that is recognized by said immunologically specific antibodies of the invention, wherein the peptide epitope is in a configuration that is sufficiently structurally equivalent to the configuration of this amino acid sequence in the native ARL-1 protein. The immunological specificity of antibodies of this invention is shown, inter alia, in FIG. 1 as described in more detail herein. As used herein, the term "immunologically specific" is intended to mean that the antibodies of this invention specifically bind to the ARL-1 species of protein without significantly detectable cross-reactivity to any other species of the AKR superfamily that are expressed in gastrointestinal and other tissues.

Antibodies of the invention can be produced by any method known in the art for the synthesis of antibodies, including chemical synthesis or recombinant expression techniques, or preferably using conventional immunological methods. As used herein, the term "antibody" includes, but is not limited to, both naturally occurring and non-naturally occurring antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. More specifically, the term "antibody" includes polyclonal and monoclonal antibodies, and antigen-binding fragments thereof such as Fab, Fab', and F(ab')$_2$ fragments. Furthermore, the term "antibody" includes chimeric antibodies and wholly synthetic antibodies, including genetically engineered antibodies, and fragments thereof. The polyclonal and monoclonal antibodies may be "purified" which means the polyclonal and monoclonal antibodies are free of any other antibodies.

The ARL-1 epitope peptide or ARL-1 protein fragment comprising said epitope peptide disclosed herein is advantageously used to prepare antibodies that specifically bind to ARL-1 species of the AKR protein family. Alternatively, full-length ARL-1 protein can be used to prepare antibodies that specifically bind to ARL-1 protein. Antibodies are defined to be specifically binding if they bind ARL-1 with a $K_a$ of greater than or equal to $10^7$/M. The affinity of a monoclonal antibody can be readily determined by one of ordinary skill in the art (see, for example, ANTIBODIES: A LABORATORY MANUAL, Harlow and Lane (eds.), Cold Spring Harbor Laboratory Press, 1988).

Methods for preparing polyclonal and monoclonal antibodies are well known in the art (see for example, Sambrook et al., 1989, MOLECULAR CLONING: A LABORATORY MANUAL, Second Edition, Cold Spring Harbor, N.Y.; Hurrell (Ed.), MONOCLONAL HYBRIDOMA ANTIBODIES: TECHNIQUES AND APPLICATIONS, CRC Press, Inc., Boca Raton, Fla., 1982, which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of an ARL-1 epitope peptide or ARL-1 protein fragment comprising said epitope peptide as disclosed herein or the full-length ARL-1 polypeptide or fragments thereof can be increased through the use of an adjuvant such as Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Information concerning adjuvants and various aspects of immunoassays are disclosed, for example, in Tijssen (1987, PRACTICE AND THEORY OF ENZYME IMMUNOASSAYS, 3rd Ed., Elsevier: N.Y.). Other useful references covering methods for preparing polyclonal antisera include MICROBIOLOGY (1969, Hoeber Medical Division, Harper and Row); Landsteiner (1962, SPECIFICITY OF SEROLOGICAL REACTIONS, Dover Publications: New York), and Williams et al. (1967, METHODS IN IMMUNOLOGY AND IMMUNOCHEMISTRY, Vol. 1, Academic Press: New York).

As is well known in the art, a given composition may vary in its immunogenicity. An ARL-1 antigenic protein fragments may be joined to other materials, particularly polypeptides, as fused or covalently joined polypeptides to be used as immunogens. An antigen and its fragments may be fused or covalently linked to a variety of immunogens, such as keyhole limpet hemocyanin (KLH), bovine serum albumin (BSA) and other albumins such as ovalbumin, mouse serum albumin or rabbit serum albumin, tetanus toxoid, etc. Means for conjugating a polypeptide to a carrier protein are well known in the art and include glutaraldehyde, m-maleimidobenzoyl-N-hydroxysuccinimide ester, carbodiimide and bis-biazotized benzidine. See MICROBIOLOGY, 1969, Id.; Landsteiner, 1962, Id.; Williams et al., 1967, Id.; and Harlow and Lane, 1988, Id., for descriptions of methods of preparing polyclonal antisera.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored.

Serum produced from animals immunized using standard methods can be used directly, or the IgG fraction can be separated from the serum using standard methods such as plasmaphoresis or adsorption chromatography with IgG-specific adsorbents such as immobilized Protein A.

Antibody fragments, such $F(ab')_2$ and Fab fragments, can be produced from the corresponding antibodies by cleavage of and collection of the desired fragments in accordance with known methods (see, for example, Andrew et al., 1992, "Fragmentation of Immunoglobulins" in CURRENT PROTOCOLS IN IMMUNOLOGY, Unit 2.8, Greene Publishing Assoc. and John Wiley & Sons).

A variety of assays known to those skilled in the art can be utilized to detect antibodies that specifically bind to an ARL-1 antigenic fragment. Exemplary assays are described in detail in Harlow & Lane (1988, Id.). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Alternatively, monoclonal antibodies against the ARL-1 antigenic peptides of the invention can be prepared according to well-known techniques, such as those exemplified in U.S. Pat. No. 4,196,265, incorporated herein by reference. Hybridomas producing monoclonal antibodies against the ARL-1 antigenic peptides of the invention are produced by well-known techniques. Usually, the process involves the fusion of an immortalizing cell line with a B-lymphocyte that produces the desired antibody. Immortalizing cell lines are usually transformed mammalian cells, particularly myeloma cells of rodent, bovine, and human origin. Rodents such as mice and rats are preferred animals, however, the use of rabbit or sheep cells is also possible. Mice are preferred, with the BALB/c mouse being most preferred as this is most routinely used and generally gives a higher percentage of stable fusions.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen, and the animal is permitted to generate the desired antibody-producing cells before they are harvested for fusion with the immortalizing cell line. Most frequently, immortalized cell lines are rat or mouse myeloma cell lines that are employed as a matter of convenience and availability. Techniques for fusion are also well known in the art, and in general involve mixing the cells with a fusing agent, such as polyethylene glycol.

Generally, following immunization somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately fifty million to two hundred million lymphocytes.

Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art. Available murine myeloma lines, such as those from the American Type Culture Collection (ATCC), 10801 University Boulevard, Manassas, Va. 20110-2209, USA, may be used in the hybridization. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler et al., 1975, Nature 256:495; Kohler et al., 1976, Eur. J. Immunol. 6:511; Kohler et al., 1976, Eur. J. Immunol. 6:292), and those using polyethylene glycol (PEG), such as 37% (v/v) PEG, by Gefter et al., 1977, Somat. Cell Genet. 3: 231-236). The use of electrically induced fusion methods is also appropriate (Goding, 1986, MONOCLONAL ANTIBODIES: PRINCIPLES AND PRACTICE, Academic Press: N.Y.).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. The preferred selection medium is HAT. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

Culturing the fusion products under these conditions provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Hybridomas secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques (such as Tijssen, 1985, Id.). The assay should be sensitive, simple and rapid, such as radioimmunoassay, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide mAbs. The cell lines may be exploited for mAb production in at least two ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Many references are available to provide guidance in applying the above techniques, including Kohler et al. (1980, HYBRIDOMA TECHNIQUES, Cold Spring Harbor Laboratory, New York); Tijssen (1985, Id.); Campbell (1984, MONOCLONAL ANTIBODY TECHNOLOGY, Elsevier: Amsterdam); Hurrell (1982, Id.). Monoclonal antibodies can also be produced using well-known phage library systems. See, for example, Huse et al. (1989, *Science* 246:1275); Ward et al. (1989, *Nature* 341:544).

Antibodies of the present invention can also be generated using various phage display methods known in the art. In phage display methods, functional antibody domains are displayed on the surface of phage particles that carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, $F_v$ or disulfide stabilized $F_v$ antibody domains recombinantly fused to either the phage gene III or gene VIII protein.

Examples of phage display methods that can be used to make the antibodies of the present invention include those disclosed in Brinkman et al. (1995, *J. Immunol. Methods* 182:41-50); Ames et al. (1995, *J. Immunol. Meth.* 184:177-186); Kettleborough et al. (1994, *Eur. J. Immunol.* 24:952-958); Persic et al. (1997, *Gene* 187:9-18); Burton et al. (1994, *Adv. Immunol.* 57:191-280); PCT application No. PCT/GB91/01134; PCT publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and U.S. Pat. No. 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al. (1992, *BioTechniques* 12:864-869); Sawai et al. (1995, *AJRI* 34:26-34); and Better et al. (1988, *Science* 240:1041-1043), said references incorporated by reference in their entireties.

Examples of techniques that can be used to produce single-chain $F_v$s and antibodies include those described in U.S. Pat. No. 4,946,778 and U.S. Pat. No. 5,258,498; Huston et al. (1991, *Methods in Enzymology* 203:46-88); Shu et al. (1993, *Proc. Natl. Acad. Sci. USA* 90:7995-7999); and Skerra et al. (1998, *Science* 240:1038-1040).

The invention further provides polynucleotides comprising a nucleotide sequence encoding an antibody of the invention and fragments thereof. The invention also encompasses polynucleotides that hybridize under stringent hybridization conditions to polynucleotides that encode an antibody, preferably, that specifically binds to a polypeptide of the invention, preferably, an antibody that binds to a peptide having the amino acid sequence of SEQ ID NO:1.

The polynucleotides may be obtained, and the nucleotide sequence of the polynucleotides determined, by any method known in the art. For example, if the amino acid or nucleotide sequence of the antibody is known, a polynucleotide encoding the antibody may be assembled from chemically synthesized oligonucleotides (such as described in Kutmeier et al., 1994, BioTechniques 17:242). Alternatively, a polynucleotide encoding an antibody may be generated from nucleic acid from a suitable source, such as a hybridoma that expresses said antibody. In the embodiments, the polynucleotide can be obtained from the cellular source using conventional methods, such as from a cDNA library or by PCR amplification of reverse-transcriptase (RT)-treated hybridoma cellular mRNA using synthetic primers that hybridize to the 3' and 5' ends of the sequence. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Id. and Ausubel et al., eds., 1998, CURRENT PROTOCOLS IN MOLECULAR BIOLOGY, John Wiley & Sons, NY, which are both incorporated by reference herein in their entireties), to generate antibodies having a different amino acid sequence, for example to create amino acid substitutions, deletions, and/or insertions.

In specific embodiments, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described in the art. The framework regions may be naturally occurring or consensus framework regions, and preferably human framework regions (see, for example, Chothia et al., 1998, *J. Mol. Biol.* 278: 457-479 for a listing of human framework regions). Preferably, the polynucleotide generated by the combination of the framework regions and CDRs encodes an antibody that specifically binds a polypeptide of the invention. Preferably, as discussed herein, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, *Proc. Natl. Acad. Sci. USA* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, *Science* 242:423-42; Huston et al., 1988, *Proc. Natl. Acad. Sci. USA* 85:5879 5883; and Ward et al., 1989, *Nature* 334: 544-54) can be adapted to produce single chain antibodies. Single chain antibodies are formed by linking the heavy and light chain fragments of the $F_v$ region via an amino acid bridge, resulting in a single chain polypeptide. Techniques for the assembly of functional $F_v$ fragments in *E. coli* may also be used (Skerra et al., 1988, *Science* 242:1038 1041).

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein.

Methods well-known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, for example, PCT Publication Nos. WO86/05807, WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed herein.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Preferably, bacterial cells such as *E. coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; Cockett et al., 1990, *Bio/Technology* 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors that direct expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, *J. Biol. Chem.* 24:5503-5509); and the like. pGEX vectors (Stratagene, LaJolla, Calif.) may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems maybe utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (See, for example, Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and other elements (see Bittner et al., 1987, *Methods in Enzymol.* 153:515-44).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter and enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc.] Natl. Acad. Sci. USA* 48:202), and adenine phosphoribosyltransferase (Lowy et al., 1980, *Cell* 22:817) genes can be employed in TK-, HGPRT- or APRT-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527; gpt, which confers resistance to mycophenolic acid (Mulligan & Berg, 1981, *Proc. Natl. Acad. Sci. USA* 78:2072; neo, which confers resistance to the aminoglycoside G-418 (Mulligan, 1993, *Science* 260:926-932; and hyg, which confers resistance to hygromycin (Santerre et al., 1984, *Gene* 30:147. Methods commonly known in the art of recombinant DNA technology may be routinely applied to select the desired recombinant clone, and such methods are described, for example, in Ausubel et al. (eds.), 1993, Id.; Kriegler, 1990, GENE TRANSFER AND EXPRESSION, A LABORATORY MANUAL, Stockton Press, NY; and Colberre-Garapin et al., 1981, *J. Mol. Biol.* 150:1, which are incorporated by reference herein in their entireties.

The expression levels of an antibody molecule can be increased by vector amplification. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers that enable equal expression of heavy and light chain polypeptides (U.S. Pat. Nos. 4,816,567, 6,331,415). Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibodies thus produced, whether polyclonal or monoclonal, can be used, e.g., in an immobilized form bound to a solid support by well-known methods.

Antibodies against the antigenic peptides of the invention can also be used, unlabeled or labeled by standard methods, as the basis for immunoassays and immunospecific binding to ARL-1. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Id.).

In particular, the antibodies of the present invention may also be used in conjunction with both fresh-frozen and/or formalin-fixed, paraffin-embedded tissue blocks prepared for study by immunohistochemistry (IHC). For example, immunohistochemistry may be utilized to evaluate tumor tissue for expression of ARL-1 species.

Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. The particular label used will depend upon the type of immunoassay. Examples of labels that can be used include but are not limited to radiolabels such as $^{3}$H, $^{14}$C, $^{32}$P, $^{125}$I, $^{131}$I, $^{111}$In or $^{99}$Tc; fluorescent labels such as fluorescein and its derivatives, rhodamine and its derivatives, dansyl and umbelliferone; chemiluminescers such as luciferase and 2,3-dihydro-phthalazinediones; and enzymes such as horseradish peroxidase, alkaline phosphatase, lysozyme, glucose-6-phosphate dehydrogenase, and acetylcholinesterase. The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, for example, in IMMUNOASSAY: A PRACTICAL GUIDE (1987, Chan (Ed.), Academic Press, Inc.:Orlando, Fla.).

Further, antibodies of the invention may also be used as therapeutic agents in treating cancer, particularly lung and liver cancer where ARL-1 is overexpressed relative to normal liver and lung tissues. An antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepachlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Alternatively, antibody treatment itself, for example with neutralizing antibodies (deactivating functional ARL-1), can be efficacious if it blocks detoxification or enhances the sensitivity of antitumor agents that are ARL-1 substrates. The high specificity of the antibodies of this invention are advantageous, since this property of the antibodies minimizes cross-reactivity with other members of the AKR superfamily of related proteins, and hence reduces cytotoxicity in normal tissues.

Also provided are related epitope compounds within the understanding of those with skill in the art, such as chemical mimetics, organomimetics or peptidomimetics. As used herein, the terms "mimetic," "peptide mimetic," "peptidomimetic," "organomimetic" and "chemical mimetic" are intended to encompass peptide derivatives, peptide analogues and chemical compounds having an arrangement of atoms is a three-dimensional orientation that is equivalent to that of a peptide of the invention and form an antigenic epitope sufficient to raise antibodies, including polyclonal antisera and monoclonal antibodies, that are immunologically equivalent to the native peptide epitope. It will be understood that the phrase "immunologically equivalent to" as used herein is intended to encompass compounds having substitution of certain atoms or chemical moieties in said peptide with moieties having bond lengths, bond angles and arrangements thereof in the mimetic compound that produce the same or sufficiently similar arrangement or orientation of said atoms and moieties to be recognized by antibodies having the complementary arrangement of amino acids to produce substantially the same antigen binding site in said antibodies and that bind to the native epitope with substantially the same affinity and avidity. In the peptide mimetics of the invention, the three-dimensional arrangement of the chemical constituents is structurally and/or functionally equivalent to the three-dimensional arrangement of the peptide backbone and component amino acid sidechains in the peptide, resulting in such peptido-, organo- and chemical mimetics of the peptides of the invention having substantial biological activity. These terms are used according to the understanding in the art, as illustrated for example by Fauchere, 1986, *Adv. Drug Res.* 15: 29; Veber & Freidinger, 1985, *TINS* p. 392; and Evans et al., 1987, *J. Med. Chem.* 30: 1229, incorporated herein by reference.

It is understood that the peptide portion of ARL-1 protein used as an antigen for raising the antibodies of the invention comprises an epitope that defines the chemical and three-dimensional structure of these antibodies. This antigenic epitope is understood in the art as comprising a three-dimensional structure that defines the immunological activity of the epitope. Peptido-, organo- and chemical mimetics can be designed to fit each epitope with current computer modeling software (computer aided drug design). Said mimetics are produced by structure-function analysis, based on the positional information from the substituent atoms in the peptides of the invention.

Peptides as provided by the invention can be advantageously synthesized by any of the chemical synthesis techniques known in the art, particularly solid-phase synthesis techniques, for example, using commercially-available automated peptide synthesizers. Mimetics of the present invention can be synthesized by solid phase or solution phase methods conventionally used for the synthesis of peptides (see, for example, Merrifield, 1963, *J. Amer. Chem. Soc.* 85: 2149-54; Carpino, 1973, *Acc. Chem. Res.* 6: 191-98; Bin, 1978, Aspects of the Merrifield Peptide Synthesis, Springer-Verlag: Heidelberg; The Peptides: Analysis, Synthesis, Biology, Vols. 1, 2, 3, 5, (Gross & Meinhofer, eds.), Academic Press: New York, 1979; Stewart et al., 1984, Solid Phase Peptide Synthesis, 2nd. ed., Pierce Chem. Co.: Rockford, Ill.; Kent, 1988, *Ann. Rev. Biochem.* 57: 957-89; and Gregg et al., 1990, *Int. J. Peptide Protein Res.* 55: 161-214, which are incorporated herein by reference in their entirety.)

The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization and coupling of successive protected amino acid derivatives are used to link the amino acids from the C-terminus according to the amino acid sequence. For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydryl-amine resin, and 4-(2', 4'-dimethoxyphenyl-FMOC-amino-methyl)-phenoxyacetamidonorleucyl-MBHA resin (Rink amide MBHA resin). In addition, acid-sensitive resins also provide C-terminal acids, if desired. A particularly preferred protecting group for alpha amino acids is base-labile 9-fluorenylmethoxy-carbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys(Trit), FMOC-Ser (But), FMOC-Asn(Trit), FMOC-Leu, FMOC-Thr(Trit), FMOC-Val, FMOC-Gly, FMOC-Lys(Boc), FMOC-Gln (Trit), FMOC-Glu(OBut), FMOC-His(Trit), FMOC-Tyr (But), FMOC-Arg(PMC (2,2,5,7,8-pentamethylchroman-6-sulfonyl)), FMOC-Arg(BOC)$_2$, FMOC-Pro, and FMOC-Trp (BOC). The amino acid residues can be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophosphonium hexa-fluorophosphate), PyB OP (benzotriazole-1-yl-oxy-tris-pyrrolidinophosphonium hexafluoro-phosphate), PyBrOP (bromo-tris-pyrrolidinophosphonium hexafluorophosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU (2-(1H-benzotriazole-1-yl),1,1,3,3-tetramethyluronium hexafluorophosphate) or HATU (2-(1H-7-aza-benzotriazole-1-yl),1,1, 3,3-tetramethyluronium hexafluoro-phosphate) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like; Applied Biosystems, Foster City, Calif.) is preferred. In a typical synthesis, the first (C-terminal) amino acid is loaded on the chlorotrityl resin. Successive deprotection (with 20% piperidine/NMP (N-methylpyrrolidone)) and coupling cycles according to ABI FastMoc protocols (ABI user bulletins 32 and 33, Applied Biosystems) are used to build the whole peptide sequence. Double and triple coupling, with capping by acetic anhydride, may also be used.

The synthetic peptides, or when appropriate synthetic mimetic peptides, are cleaved from the resin and deprotected by treatment, for example, with TFA (trifluoroacetic acid) containing appropriate scavengers. Many such cleavage reagents, such as Reagent K (0.75 g crystalline phenol, 0.25 mL ethanedithiol, 0.5 mL thioanisole, 0.5 mL deionized water, 10 mL TFA) and others, can be used. The peptide is separated from the resin by filtration and isolated by ether precipitation. Further purification may be achieved by conventional methods, such as gel filtration and reverse phase HPLC (high performance liquid chromatography). Synthetic mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization out of the appropriate base.

Generally, those skilled in the art will recognize that peptides as described herein may be modified by a variety of chemical techniques to produce compounds forming essentially the same immunological epitope as the unmodified peptide, and optionally having other desirable properties. For example, carboxylic acid groups of the peptide may be provided in the form of a salt of a pharmaceutically-acceptable cation. Amino groups within the peptide may be in the form of a pharmaceutically-acceptable acid addition salt, such as the HCl, HBr, acetic, benzoic, toluene sulfonic, maleic, tartaric and other organic salts, or may be converted to an amide. Thiols can be protected with any one of a number of well-recognized protecting groups, such as acetamide groups. Those skilled in the art will also recognize methods for introducing cyclic structures into the peptides of this invention so that the native binding configuration will be more nearly approximated. For example, a carboxyl terminal or amino terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Specifically, a variety of techniques are available for constructing peptide derivatives and analogues with the same or similar desired immunological activity as the corresponding peptide compound but with more favorable activity than the peptide with respect to solubility, stability, and susceptibility to hydrolysis and proteolysis. Such derivatives and analogues include peptides modified at the N-terminal amino group, the C-terminal carboxyl group, and/or changing one or more of the amido linkages in the peptide to a non-amido linkage. It will be understood that two or more such modifications can be coupled in one peptide mimetic structure (e.g., modification at the C-terminal carboxyl group and inclusion of a —$CH_2$— carbamate linkage between two amino acids in the peptide).

Amino terminus modifications include alkylating, acetylating, adding a carbobenzoyl group, and forming a succinimide group. Specifically, the N-terminal amino group can then be reacted to form an amide group of the formula RC(O)NH— where R is alkyl, preferably lower alkyl, and is added by reaction with an acid halide, RC(O)Cl or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—. Alternatively, the amino terminus can be covalently linked to succinimide group by reaction with succinic anhydride. An approximately equimolar amount or an excess of succinic anhydride (e.g., about 5 equivalents) are used and the terminal amino group is converted to the succinimide by methods well known in the art including the use of an excess (e.g., ten equivalents) of a tertiary amine such as diisopropylethylamine in a suitable inert solvent (e.g., dichloromethane), as described in Wollenberg et al., U.S. Pat. No. 4,612,132, is incorporated herein by reference in its entirety. It will also be understood that the succinic group can be substituted with, for example, $C_2$- through $C_6$-alkyl or —SR substituents, which are prepared in a conventional manner to provide for substituted succinimide at the N-terminus of the peptide. Such alkyl substituents are prepared by reaction of a lower olefin ($C_2$- through $C_6$-alkyl) with maleic anhydride in the manner described by Wollenberg et al., supra, and —SR substituents are prepared by reaction of RSH with maleic anhydride where R is as defined above. In another advantageous embodiments, the amino terminus is derivatized to form a benzyloxycarbonyl-NH— or a substituted benzyloxycarbonyl-NH— group. This derivative is produced by reaction with approximately an equivalent amount or an excess of benzyloxycarbonyl chloride (CBZ—Cl) or a substituted CBZ—Cl in a suitable inert diluent (e.g., dichloromethane) preferably containing a tertiary amine to scavenge the acid generated during the reaction. In yet another derivative, the N-terminus comprises a sulfonamide group by reaction with an equivalent amount or an excess (e.g., 5 equivalents) of R—$S(O)_2$Cl in a suitable inert diluent (dichloromethane) to convert the terminal amine into a sulfonamide, where R is alkyl and preferably lower alkyl. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes). Carbamate groups are produced at the amino terminus by reaction with an equivalent amount or an excess (e.g., 5 equivalents) of R—OC(O)Cl or R—OC(O)O$C_6H_4$-p—$NO_2$ in a suitable inert diluent (e.g., dichloromethane) to convert the terminal amine into a carbamate, where R is alkyl, preferably lower alkyl. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes). Urea groups are formed at the amino terminus by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. preferably, the inert diluent contains an excess (e.g., about 10 equivalents) of a tertiary amine, such as diisopropylethylamine. Reaction conditions are otherwise conventional (e.g., room temperature for about 30 minutes).

In preparing peptide mimetics wherein the C-terminal carboxyl group is replaced by an ester (e.g., —C(O)OR where R is alkyl and preferably lower alkyl), resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester. In preparing peptide mimetics wherein the C-terminal carboxyl group is replaced by the amide —C(O)$NR_3R_4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)$NH_2$). Alternatively, use of the chloromethylated resin during peptide synthesis coupled with reaction with ammonia to cleave the side chain Protected peptide from the support yields the free peptide amide and reaction with an alkylamine or a dialkylamine yields a side chain protected alkylamide or dialkylamide (i.e., the C-terminus is —C(O)$NRR_1$, where R and $R_1$ are alkyl and preferably lower alkyl). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by displacement of the —OH or the ester (—OR) of the carboxyl group or ester respectively with the N-terminal amino group to form a cyclic peptide. For example, after synthesis and cleavage to give the peptide acid, the free acid is converted in solution to an activated ester by an appropriate carboxyl group activator such as dicyclohexylcarbodiimide (DCC), for example, in methylene chloride ($CH_2Cl_2$), dimethyl formamide (DMF), or mixtures thereof. The cyclic peptide is then formed by displacement of the activated ester with the N-terminal amine. Cyclization, rather than polymerization, can be enhanced by use of very dilute solutions according to methods well known in the art.

Peptide mimetics as understood in the art and provided by the invention are structurally similar to the paradigm peptide of the invention, but have one or more peptide linkages optionally replaced by a linkage selected from the group consisting of: —$CH_2$NH—, —$CH_2$S—, —$CH_2CH_2$—, —CH=CH— (in both cis and trans conformers), —$COCH_2$—, —CH(OH)$CH_2$—, and —$CH_2$SO—, by methods known in the art and further described in the following references: Spatola, 1983, in CHEMISTRY AND BIOCHEMISTRY OF AMINO ACIDS, PEPTIDES, AND PROTEINS, (Weinstein, ed.), Marcel Dekker: New York, p. 267; Spatola, 1983, *Peptide Backbone Modifications* 1: 3; Morley, 1980, *Trends Pharm. Sci.* pp. 463-468; Hudson et al., 1979, *Int. J. Pept. Prot. Res.* 14: 177-185; Spatola et al., 1986, *Life Sci.* 38: 1243-1249; Hann, 1982, *J. Chem. Soc. Perkin Trans.* 1307-314; Almquist et al., 1980, *J. Med. Chem.* 23: 1392-1398; Jennings-White et al., 1982, *Tetrahedron Lett.* 23: 2533; Szelke et al., 1982, European Patent Application, Publication No. EP045665A; Holladay et al., 1983, *Tetrahedron Lett.* 24: 4401-4404; and Hruby, 1982, *Life Sci.* 31: 189-199, each of which is incorporated herein by reference. Such peptide mimetics may have significant advantages over polypeptide embodiments, including, for example: being more economical to produce, having greater chemical stability or enhanced pharmacological properties (such half-life, absorption, potency, efficacy, etc.), enhanced antigenicity, and other properties.

Mimetic analogs of the epitope peptides of the invention may also be obtained using the principles of conventional or rational drug design (see, Andrews et al., 1990, *Proc. Alfred Benzon Symp.* 28: 145-165; McPherson, 1990, *Eur. J. Biochem.* 189:1-24; Hol et al., 1989a, in MOLECULAR RECOGNITION: CHEMICAL AND BIOCHEMICAL PROBLEMS, (Roberts, ed.); Royal Society of Chemistry; pp. 84-93; Hol, 1989b, *Arzneim-Forsch.* 39:1016-1018; Hol, 1986, *Agnew Chem. Int. Ed. Engl.* 25: 767-778, the disclosures of which are herein incorporated by reference).

In accordance with the methods of conventional drug design, the desired mimetic molecules are obtained by randomly testing molecules whose structures have an attribute in common with the structure of a "native" peptide. The quantitative contribution that results from a change in a particular group of a binding molecule can be determined by measuring the biological activity of the putative mimetic in comparison with the antigenic capacity, or binding affinity to the antibodies of the invention, of the native peptide. In a preferred embodiment of rational drug design, the mimetic is designed to share an attribute of the most stable three-dimensional conformation of the peptide. Thus, for example, the mimetic may be designed to possess chemical groups that are oriented in a way sufficient to cause ionic, hydrophobic, or van der Waals interactions that are similar to those exhibited by the antigenic capacity, or binding affinity to the antibodies of the invention, of the native peptides of the invention, as disclosed herein.

The preferred method for performing rational mimetic design employs a computer system capable of forming a representation of the three-dimensional structure of the peptide, such as those exemplified by Hol, 1989a, Id.; Hol, 1989b, Id.; and Hol, 1986, Id. Molecular structures of the peptido-, organo- and chemical mimetics of the peptides of the invention are produced according to those with skill in the art using computer-assisted design programs commercially available in the art. Examples of such programs include SYBYL 6.5®, HQSAR™, and ALCHEMY 2000™ (Tripos); GALAXY™ and Am2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.) and CHEMBUILDER3D™ (Interactive Simulations, Inc., San Diego, Calif.).

The peptido-, organo- and chemical mimetics produced using the peptides disclosed herein using, for example, art-recognized molecular modeling programs are produced using conventional chemical synthetic techniques, most preferably designed to accommodate high throughput screening, including combinatorial chemistry methods. Combinatorial methods useful in the production of the peptido-, organo- and chemical mimetics of the invention include phage display arrays, solid-phase synthesis and combinatorial chemistry arrays, as provided, for example, by SIDDCO, Tuscon, Ariz.; Tripos, Inc.; Calbiochem/Novabiochem, San Diego, Calif.; Symyx Technologies, Inc., Santa Clara, Calif.; Medichem Research, Inc., Lemont, Ill.; Pharm-Eco Laboratories, Inc., Bethlehem, Pa.; or N.V. Organon, Oss, Netherlands. Combinatorial chemistry production of the peptido-, organo- and chemical mimetics of the invention are produced according to methods known in the art, including but not limited to techniques disclosed in Terrett, 1998, COMBINATORIAL CHEMISTRY, Oxford University Press, London; Gallop et al., 1994, "Applications of combinatorial technologies to drug discovery. 1. Background and peptide combinatorial libraries," *J. Med. Chem.* 37: 1233-51; Gordon et al., 1994, "Applications of combinatorial technologies to drug discovery. 2. Combinatorial organic synthesis, library screening strategies, and future directions," *J. Med. Chem.* 37: 1385-1401; Look et al., 1996, *Bioorg. Med. Chem. Lett.* 6: 707-12; Ruhland et al., 1996, *J. Amer. Chem. Soc.* 118: 253-4; Gordon et al., 1996, *Acc. Chem. Res.* 29: 144-54; Thompson & Ellman, 1996, *Chem. Rev.* 96: 555-600; Fruchtel & Jung, 1996, *Angew. Chem. Int. Ed. Engl.* 35: 17-42; Pavia, 1995, "The Chemical Generation of Molecular Diversity," Network Science Center, www-.netsci.org; Adnan et al., 1995, "Solid Support Combinatorial Chemistry in Lead Discovery and SAR Optimization," Id., Davies and Briant, 1995, "Combinatorial Chemistry Library Design using Pharmacophore Diversity," Id., Pavia, 1996, "Chemically Generated Screening Libraries: Present and Future," Id.; and U.S. Pat. No. 5,880,972 to Horlbeck; 5,463,564 to Agrafiotis et al.; U.S. Pat. No. 5,331,573 to Balaji et al.; and U.S. Pat. No. 5,573,905 to Lerner et al.

Kits as provided by the invention comprise antibodies of the invention, in embodiments that are polyclonal antisera, monoclonal antibodies or fragments or derivatives thereof, preferably conjugated to a detectable substance, and instructions for their use. The components of the kit are advantageously provided in a container to preserve their integrity. In certain embodiments, the antibodies of the invention are provided in dry form, as powders or lyophilizates, and in these embodiments the kit advantageously includes liquid buffers or other reagents for reconstitution of the dry antibody preparations, as well as instructions for such reconstitution. Certain embodiments of the kits of the invention include reagents, in dried or liquid form, for use in the practice of the methods of the invention. These reagents can include, inter alia, a control sample, buffers, salts, hybridization solutions, washing solutions, secondary antibodies, reagents for labeling primary or secondary antibodies, and reagents such as enzyme substrates for developing the results of, for example, an in situ hybridization assay. Instructions for use of any of these reagents are also advantageously included in such kits. Still another aspect of the invention is a pharmaceutical composition comprising an antibody of the invention. In one embodiment, the pharmaceutical composition comprises an antibody of the invention and a pharmaceutically acceptable carrier.

Figure 27:
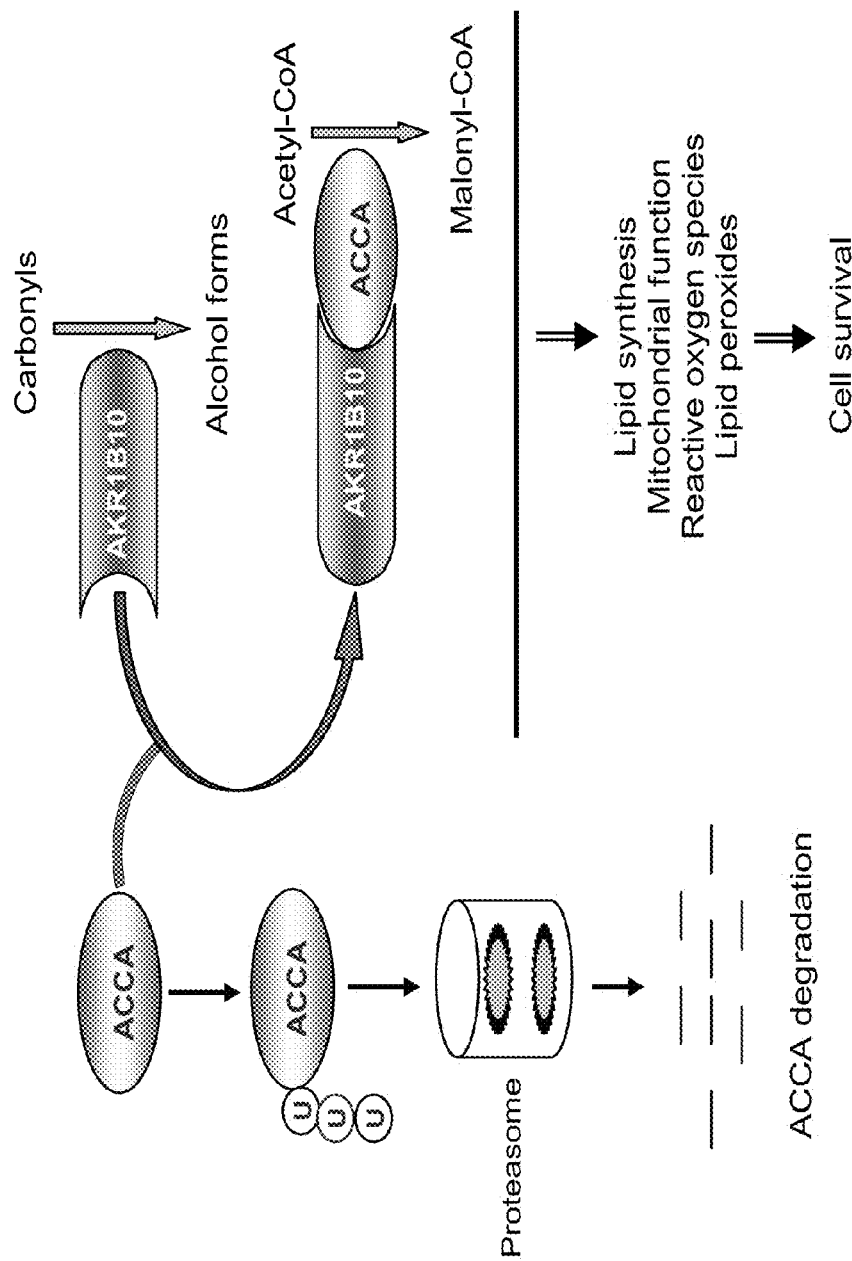
FIG. 27 is a diagram illustrating the role of AKR1B10 (ARL-1) in lipogenesis.

The roles of ARL-1 in detoxifying carbonyls and mediating fatty acid synthesis and lipid metabolism in relation to cell growth and survival have been suggested (Yan, et al., 2007, *Int J Cancer*, 121: 2301-2306; Zu et al., 2007, *Toxicol Sci*, 97: 562-568; Wang et al., 2009, *J Biol Chem* 284: 26742-26748; Ma et al., 2008, *J Biol Chem* 283: 3418-3423). ARL-1 reduces cellular $\alpha,\beta$-unsaturated carbonyls at physiological levels to less toxic alcohols (Zhong et al., 2009, *Biochem Biophys Res Commun* 387: 245-250). Introduction of ARL-1 into 293T cells promotes cell proliferation and clonogenic growth whereas siRNA-triggered ARL-1 silencing leads to cell growth inhibition, apoptotic death, and susceptibility to carbonyls in HCT-8 and NCI-H460 cells (Yan et al., 2007, *Int J Cancer* 121: 2301-2306; Zu et al., 2007, *Toxicol Sci* 97: 562-568; Wang et al., 2009, *J Biol Chem* 284: 26742-26748). In addition, lipogenesis is critical to cancer cell growth and division, and increased lipogenesis and lipogenic enzymes such as fatty acid synthase (FAS) and acetyl-CoA carboxylase alpha (ACCA) are early events during carcinogenesis and cancer development (Rossi et al., 2003, *Mol Cancer Res* 1: 707-715; Witters et al., 1994, *Int J Biochem* 26: 589-594). ARL-1 associates with and stabilizes ACCA, the rate-limiting enzyme in cellular lipogenesis, thereby promoting lipid metabolism (FIG. 27).

ARL-1 protein is over expressed in human breast carcinoma, human hepatocellular carcinoma and lung squamous cell carcinoma and adenocarcinoma. On the other hand, ARL-1 protein is under-expressed or expression is lost in gastrointestinal cancer and precancerous lesions. Thus, ARL-1 is a marker for the diagnosis and/or early diagnosis of cancer, using either the antibodies of the invention or antibodies raised by immunizing an animal with a peptide having the sequence set forth in SEQ ID NO:1 or with a full-length ARL-1 protein having the sequence set forth in SEQ ID NO:5, or a combination thereof. The full-length nucleic acid and protein sequences of ARL-1 are set forth in SEQ ID NOs: 4 and 5, respectively, as disclosed under GenBank Accession No. U37100. It is within the knowledge of an ordinary skilled in the art, and further described throughout this application how to purify native or recombinantly expressed ARL-1 protein for use as an immunogen, immunizing animals according to standard procedures, and isolating and testing sera for reactivity and specificity for ARL-1 protein.

The results presented herein demonstrated that ARL-1 was expressed in elevated levels in hyperplasia, cancer, and DCIS of the breast, as well as cancer and hyperplasia of the prostate, as compared to normal breast tissue or normal prostate tissue, respectively. Thus, in one aspect of the invention, methods are provided for identifying cancer or a precancerous lesion comprising the step of assaying a tissue sample from a human to detect differential ARL-1 expression, wherein cancer or a precancerous lesion is identified when ARL-1 expression in the tissue sample from the human is greater than ARL-1 expression in a normal tissue sample. In certain particular embodiments, the cancer or a precancerous lesion is breast cancer or prostate cancer, or a precancerous lesion thereof.

Reduction or loss of ARL-1 expression in a biopsy specimen of gastrointestinal organs or tissues, even in the absence of clinical manifestations of disease, as compared with a control normal gastrointestinal tissue, is a risk factor for development of cancer in gastrointestinal organs and tissues. Conversely, increased ARL-1 expression in certain other tissues, even in the absence of clinical manifestations of cancer, is a risk factor for development of cancer in these tissues. In certain particular embodiments of the invention, the tissue wherein increased ARL-1 expression is a risk factor for development of cancer even in the absence of clinical manifestations of cancer comprises breast tissue or prostate tissue. Thus, in another aspect, the invention provides methods for identifying a human at risk for developing cancer of a non-gastrointestinal tissue, comprising the step of assaying a non-cancerous human non-gastrointestinal tissue sample from a human to detect differential ARL-1 expression, wherein a human at risk for developing cancer is identified when ARL-1 expression in the non-cancerous tissue sample from the human is greater than ARL-1 expression in a corresponding control normal tissue sample. In certain embodiments, the non-gastrointestinal cancer is breast cancer or prostate cancer.

As used herein, the term "a non-cancerous tissue" refers to a tissue that does not exhibit the hallmarks of cancer, including a histologically normal tissue, a tissue with a pre-cancerous lesion and a hyperplastic tissue. In certain particular embodiments, the non-cancerous tissue is a non-cancerous breast, prostate, lung and liver tissue.

As used herein, the term a "normal," "control," "control normal," or "normal control" tissue refers to a tissue from a normal, healthy individual or volunteer, who does not have cancer, precancerous lesion or hyperplasia in the tissue. In certain particular embodiments, a normal tissue comprises a histologically normal tissue located adjacent to the cancerous tissue of the same patient. In certain other embodiments, the normal tissue comprises normal breast, prostate, lung or liver tissue located adjacent to the corresponding cancerous tissue. The ARL-1 expression levels of a normal or control human refers to the amounts or concentrations of ARL-1 protein levels of a normal healthy individual, or an average amounts or concentrations of ARL-1 protein levels of a normal healthy population. In certain embodiments, the normal healthy population refers to a control population based on corresponding ethnic, gender, or geographical groups. Accordingly, in certain particular embodiments, the ARL-1 expression levels in a tissue sample or body fluid sample from a human are compared with the ARL-1 expression levels in the corresponding tissue or body fluid samples obtained from a normal healthy population of the same ethnic group, of the same gender group, or of the same geographic group, as the human. These particular embodiments are contemplated for any and all aspects and embodiments described throughout this application. It is within the knowledge and ability of one of skill in the art to determine the suitable normal healthy population for a particular test human subject.

As shown in the examples below, ARL-1 expression in metastatic cancer cells in lymph nodes strongly correlated with ARL-1 expression in primary breast tumors ($r=0.45$, $p=0.0180$), indicating that ARL-1 can be used as a marker for tumor metastasis. Further, the percentage of recurrent breast tumors that overexpressed ARL-1 was larger than the percentage of primary breast tumors that overexpressed ARL-1. These recurrent tumors were obtained from patients who had previously received radiotherapy, chemotherapy, or hormone therapy before cancer recurrence. These therapies have been shown to induce cancer cell death by creating damages or stress in tumor cells (Girdhani et al., 2005, *J Cancer Res Ther* 1: 129-131; Viktorsson et al., 2005, *Adv Cancer Res* 94: 143-196; Zheng et al., 2007, *Endocrinology* 148: 2764-2777; Masuda et al., 2009, *Cancer Chemother Pharmacol* 64: 361-369) The results presented herein suggested that ARL-1 overexpression may confer a survival advantage to metastatic cells during metastasis and cancer treatment, and can be used as a marker for cancer recurrence and metastasis.

Thus, in another aspect of the invention, methods are provided for identifying a human at risk for recurrence of breast cancer or prostate cancer, comprising the step of assaying a breast tissue sample or a prostate tissue sample from a human who is in remission of breast cancer or prostate cancer to detect differential ARL-1 expression, wherein a human at risk for recurrence of breast cancer or prostate cancer is identified when ARL-1 expression in the breast tissue sample or prostate tissue sample from the human in remission of breast cancer or prostate cancer is greater than ARL-1 expression in a control normal breast tissue sample or control normal prostate tissue sample. In certain other embodiments, a human at risk for recurrence of breast cancer or prostate cancer is identified when ARL-1 expression in the breast tissue sample or prostate tissue sample from the human in remission of breast cancer or prostate cancer is greater than ARL-1 expression of the human in the tissue sample at an earlier time point during remission.

As used herein, the term "remission" refers to a state of absence of disease activity in a patient that is known to have a chronic disease, such as cancer. In certain embodiment, the remission is a result of treatment of a primary tumor, said treatment including without limitation chemotherapy, radiation therapy, and surgical removal of the primary tumor. In other particular embodiments, the patient in remission of a primary tumor exhibits normal level of ARL-1 expression as compared with the level of ARL-1 expression in a normal control sample. In certain embodiments, the cancer is breast, lung, liver or prostate cancer. A patient in remission of breast, lung, liver or prostate cancer exhibits significantly reduced levels of ARL-1 protein expression as compared to the levels of ARL-1 expression during the time the patient is suffering from primary tumors.

In addition, results presented herein surprisingly suggested that ARL-1 levels were inversely correlated with breast patient survival, particularly breast cancer-related survival. ARL-1 expression appeared to divide the early stage breast cancer (tumor size<2.0 cm and lymph node negative) into two distinct groups: more than 90% of patients with ARL-1-negative tumors had a 25-year survival rate while less than 50% of patients with ARL-1-expressing tumors did. The data suggested that ARL-1 expression should be taken into account and can be used as a novel marker when deciding the best treatment mode at the early stage of breast cancer that most benefits patients. Thus, in a further aspect, the invention provides methods for detecting ARL-1 expression as a cancer patient prognosis marker, wherein the levels of ARL-1 expression inversely correlate with the prognosis of the patients.

In certain advantageous embodiments, ARL-1 expression is detected in a body fluid sample. It was unexpectedly discovered and further demonstrated by the inventor that ARL-1 is a secreted protein and can be used as a cancer marker for detecting ARL-1 expression in a bodily fluid in a less invasive manner that does not require surgery. Thus, in a further aspect, the invention provides methods for identifying cancer metastasis, comprising the step of assaying a bodily fluid sample from a human to detect differential amounts or concentrations of ARL-1 protein, wherein cancer metastasis is identified when the amounts or concentrations of ARL-1 protein in the bodily fluid sample from the human is greater than the amounts or concentrations of ARL-1 protein in a control bodily fluid sample from a human without cancer or a precancerous lesion thereof, and wherein the cancer is breast cancer, lung cancer, liver cancer or prostate cancer. In certain other embodiments, cancer metastasis is identified when ARL-1 expression in a bodily fluid of the human is greater than ARL-1 expression of the human in the same type of bodily fluid at an earlier time point after the treatment of primary tumor.

As used herein, "metastasis," "cancer metastasis," or "metastatic cancer" refers to the spread of cancer from a first organ to another organ. In certain particular embodiments, the invention provides methods for identifying cancer metastasis, comprising the step of assaying a bodily fluid sample from a human having a tumor in a first organ before or after treatment thereof to detect differential amounts or concentrations of ARL-1 protein, wherein cancer metastasis is identified when the amounts or concentrations of ARL-1 protein in the bodily fluid sample from the human is greater than the amounts or concentrations of ARL-1 protein in a control bodily fluid sample from a control normal human. In certain particular embodiments, cancer metastasis refers to metastasis of breast, lung, liver or prostate cancer.

In yet a further aspect, the invention provides methods for identifying a human at risk for recurrent cancer, comprising the step of assaying a bodily fluid sample from a human in remission of a cancer to detect differential amounts or concentrations of ARL-1 protein, wherein the human is identified as at risk for recurrent cancer when the amounts or concentrations of ARL-1 protein in the bodily fluid sample from the human is greater than the amounts or concentrations of ARL-1 protein in a control bodily fluid sample from a control normal human, and wherein the cancer is breast cancer, lung cancer, liver cancer or prostate cancer. In certain other embodiments, a human is identified as at risk for recurrent cancer when ARL-1 expression in a bodily fluid of the human is greater than ARL-1 expression of the human in the same type of bodily fluid at an earlier time point during remission.

Because ARL-1 can be detected in a bodily fluid, such as serum, cancer progression in a patient can be closely monitored by analyzing ARL-1 protein levels in the patient's bodily fluids and thereby evaluating the efficacy of a particular cancer treatment. Thus, in certain other advantageous aspect, the invention provides methods for treating cancer in a cancer patient comprising the step of administering a treatment to the cancer patient, and assaying a bodily fluid sample from the cancer patient before and after the treatment to detect differential ARL-1 protein amounts or concentrations, wherein the cancer patient continues to receive the treatment when ARL-1 protein amounts or concentrations in the bodily fluid sample from the cancer patient are greater before treatment than ARL-1 protein amounts or concentrations in the bodily fluid sample from the cancer patient after treatment, wherein the treatment requires modification when ARL-1 protein amounts or concentrations in the bodily fluid sample from the cancer patient before the treatment are equal to or less than ARL-1 protein amounts or concentrations in the bodily fluid sample from the cancer patient after the treatment, and wherein the cancer is breast cancer, lung cancer, liver cancer or prostate cancer. In certain embodiments, the modification of treatment comprises increasing the dosage of a previous treatment; in certain other embodiments, the modification of treatment comprises switching from one type of treatment to a different type of treatment. By analyzing the levels of ARL-1 proteins, preferably detected in a patient's bodily fluids, as a proxy for patients' response to a treatment, a physician can decide whether any modification to the course of treatment is needed, such as termination of the existing treatment, increasing the dosage of the existing treatment, switching to a different type of treatment, or a combination thereof. The decision of choosing alternative type of treatment or proper dosage of a treatment is within the knowledge of a skilled physician.

Any immunologically-based assay can be used for these diagnostic embodiments, including immunohistochemistry of tissue samples, radioimmune assay or ELISA assay of bodily fluids or exudates, FACS analysis of shed epithelial cells in stool, and other methods and tumor sample sources known to those with skill in the art. ARL-1 related detection in body fluids include the detection of ARL-1 protein and ARL-1 antibodies that may be produced in humans in responding to ARL-1 protein in normal or cancer cells.

The description set forth above and the Examples set forth below recite exemplary embodiments of the invention. However, the disclosure set forth herein is intended to encompass any biologic anticancer agent useful against any tumor cell type for which resistance can be developed. The following Examples are intended to further illustrate certain preferred embodiments of the invention and are not limiting in nature.

EXAMPLES

Example 1

Preparation of Antigenic Peptide by Solid Phase Peptide Synthesis

A peptide (having the amino acid sequence: DDKGNAIG-GKATFLC; SEQ ID NO. 1) provided by the invention for use as specific antigen for raising the anti-ARL-1 antibodies of the invention was prepared as follows.

Solid phase peptide synthesis (SPPS) was carried out on a 0.25 millimole (mmole) scale using an Applied Biosystems Model 431A Peptide Synthesizer and using 9-fluorenylmethyl-oxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluoro-phosphate/hydroxybenzotriazole (HBTU/HOBT), and using p-hydroxymethyl phenoxymethyl-polystyrene (HMP) resin or Sasrin™, or chlorotrityl resin for carboxyl-terminus acids or Rink amide resin for carboxyl-terminus amides.

Sasrin™ resin-bound peptides are cleaved using a solution of 1% TFA in dichloromethane to yield the protected peptide. Where appropriate, protected peptide precursors are cyclized between the amino- and carboxyl-termini by reaction of sidechain-protected, amino-terminal free amine and carboxyl-terminal free acid using diphenylphosphorylazide.

HMP or Rink amide resin-bound products are routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5-3 hours at room temperature. Where appropriate, products were re-S-tritylated in triphenolmethanol/TFA, and N-Boc groups re-introduced into the peptide using $(Boc)_2O$.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or by electrospray mass spectroscopy (ESMS).

Example 2

Preparation of Polyclonal Antibodies

Polyclonal antibodies specific for the ARL-1 protein species were prepared using the epitopic peptide disclosed in Example 1. Polyclonal antibodies against an oligopeptide of SEQ ID NO. 1 prepared according to Example 1, or against purified recombinant peptide of SEQ ID NO. 1, were generated in rabbits according to standard procedures well known in the art (see, for example, Harlow & Lane, Id.). Briefly, purified peptides were conjugated with keyhole limpet hemocyanin (KLH) using conventional methods (Harlow & Lane, Id.) and immunization were performed below:

| Day 0 | Pre-immunization bleed | |
| Day 0 | Initial immunization (KLH) | 500 ug (CFA) |
| Day 14 | Boost (KLH) | 250 ug (IFA) |
| Day 28 | Boost (KLH) | 250 ug (IFA) |
| Day 37 | Test bleed (~5 ml) | ~5.0 ml |
| Day 42 | Boost (KLH) | 250 ug (IFA) |
| Day 59 | Terminal bleed (Exsanguination) | (~70-100 ml) |

The polyclonal antisera obtained from these animals were used in Western blots performed using conventional methods and protocols. Briefly stated, cells expressing different AKR superfamily members were lysed on ice for 30 min with lysis buffer (containing 10 mM HEPES, 10 mM KCl, 1 mM EDTA (pH 8.0), 0.1% NP-40, 1 mM DTT, 1 mM PMSF and 0.5 mM $Na_3VO_4$). Soluble protein (30 µg) or purified AR and ARL-1 protein (2 µg) was separated on a 12% SDS-PAGE gel and blotted onto a pure nitrocellulose membrane (Bio-Rad, CA) at 180 mA for 2 hours. After blockage with 5% skim milk in PBS at room temperature for 45 min, membranes were incubated with ARL-1 antibody-containing polyclonal antisera (1:500) in the same buffer for 1 hour or at 4° C. overnight, followed by incubation with goat anti-rabbit IgG (1:2000) for 1 hour. Antibody binding was detected using an enhanced chemiluminescence system (Pierce, Ill.). To correct protein loading amounts, membranes were re-probed with β-actin monoclonal antibody (1:40,000).

The specificity of the polyclonal antisera disclosed herein is shown in FIG. 1A, which is a photograph of Western blot analyses of three antisera used as probes of blotted recombinant ARL protein species. The results shown in FIG. 1 demonstrated that the ARL-1 antisera of this invention were the only antisera showing specificity for ARL-1 species shown herein to be differentially expressed in gastrointestinal tissues. Both of the other antisera testes showed varying levels of cross-reactivity with other AKR species, including extensive cross-reactivity with ARL-1A1, -1B1 and -IC2. These results established that the ARL-1-reactive antisera of this invention are specific for the ARL-1 species differentially expressed in gastrointestinal tissues including stomach, small intestine and colon.

Specificity of the antibodies of the invention was further shown by the experimental results set forth in FIGS. 1B and 1C. Whole cell lysates from human A549 cells (which express both ARL-1 and related AR proteins) in increasing cell numbers (Lane 2: 10,000 cells; Lane 3: 50,000 cells; Lane 4: 100,000 cells) were mixed with an equal volume of 2× SDS loading buffer and heated to 75° C. for 10 min. Before being loaded on an SDS-polyacrylamide gel and subjected to electrophoresis. The gel was then stained with Coomassie blue stain (left panel) and subjected to Western blot analysis as described above. AR (middle panel) and ARL-1 (AKR1B10; right panel) proteins were detected.

FIG. 1C shows results obtained using both cell lysates and purified protein subjected to SDS-PAGE and Western blot analysis as set forth above. Western blots were probed with antibodies specific for AR (middle panel) or ARL-1 (AKR1B10; right panel) and showed AR cross-reactivity against purified AR protein (Lane 1) and 293T cell lysates (that express AR but not ARL-1 protein; Lane 3), as well as ARL-1 cross-reactivity to ARL-1 purified protein (Lane 2) and HCT-8 cell lysates (that express ARL-1 but not AR protein; Lane 4).

Example 3

Analysis of ARL-1 Expression in Normal, Precancerous and Cancer Tissues of the GI Tract The ARL-1 specific polyclonal antisera prepared as set forth in Example 2 was used to investigate expression of ARL-1 protein in normal human gastrointestinal tract, precancerous lesions and cancers. Previously the inventor had shown that this protein was overexpressed in hepatocarcinoma (Cao et al., 1998, Id.) and overexpression of ARL-1 was independently demonstrated in certain lung cancers (Fukumoto et al., 2005, *Clin Cancer Res.* 11:1776-85.). However, little was known about ARL-1 expression in stomach, small intestine, and colon prior to this invention.

Expression in human colon epithelia was demonstrated using immunohistochemical methods as set forth in Martinet et al. (2006, *Autophagy* 2: 55-57). Briefly, formalin-fixed paraffin-embedded sections were dewaxed and stained with polyclonal antisera of the invention at a dilution of 1:5. Hematoxylin counter staining was used to indicate nuclei. The results of these assays are shown in FIG. 2. Results indicated that ARL-1 protein was specifically expressed at very high level in epithelial cells of the colon. To understand the maturation of the ARL-1 expression cells, adjacent sections were stained with Ki-67, a marker of proliferating cells, and the results clearly indicated that ARL-1 and Ki-67 were expressed in distinct cell populations. ARL-1 cells were shown by these experiments to be expressed in terminally-differentiated colon epithelia. Equivalent results were obtained when section of normal stomach and small intestine were assayed as described herein (data not shown).

Figure 4:
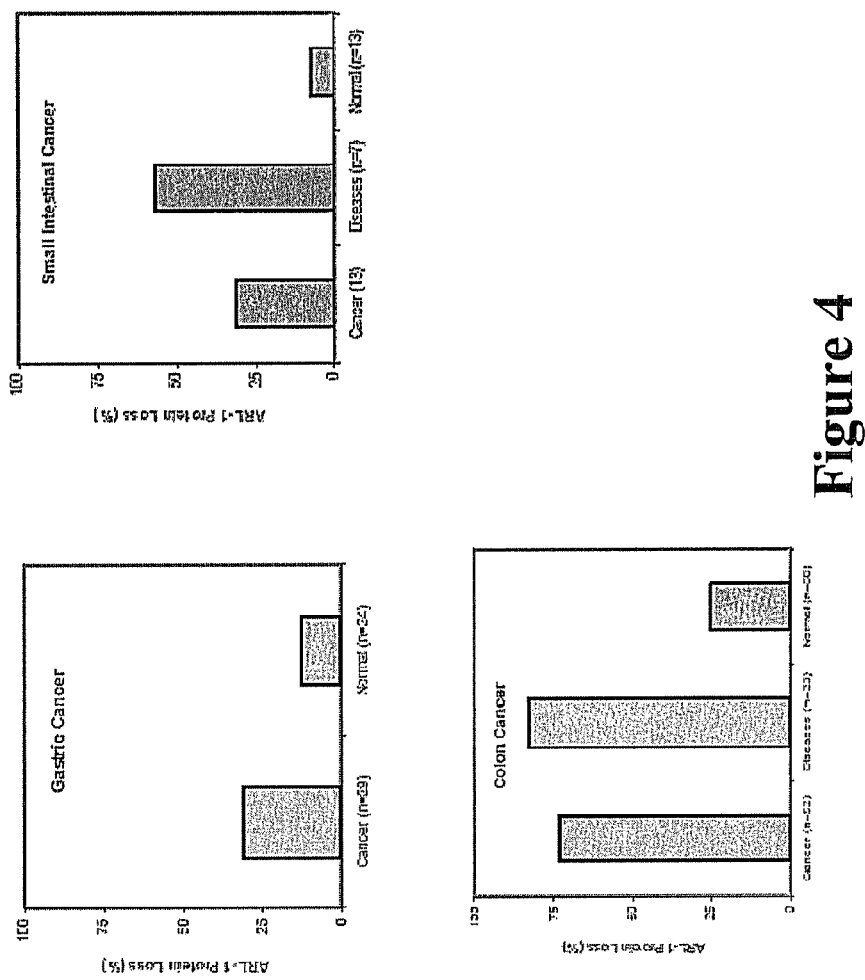
FIG. 4 is a graphical representation of ARL-1 protein loss in gastric, colon, and small bowel tissues. ARL-1 protein levels were examined by Western blot, as indicated in FIG. 3. Results are indicated as the percentage of ARL-1 loss samples over the total tested specimens. Normal indicates the matched normal tissues, and disease denotes precancerous disease samples.

To investigate the role of ARL-1 in colon tumorigenesis, mRNA and protein expression of ARL-1 gene in gastrointestinal (GI) cancer tissues was investigated. After electrophoretic separation of 50 µg solubilized protein per sample, Western blot analysis was performed as described in Example 2. ARL-1 polyclonal antisera prepared as set forth in Example 2 was used at a dilution of 1:500. Protein loading amounts per well were corrected by probing with β-actin monoclonal antibody (Sigma, St. Louis, Mo.). The results of these assays are shown in FIG. 3, where colon cancer sample were paired with normal surrounding tissues. As seen in the Figure, ARL-1 protein was undetectable in Tumor 2, 4, and 5, and was dramatically decreased in Tumor 3, compared to the paired normal tissue. Western blot assays were performed on a total of 29 gastric, 13 small bowel, and 52 colon cancer tissues, the majority of which were paired with surrounding normal tissues. ARL-1 protein levels were also checked in the surgical specimens of small intestinal (n=7) and colon (n=23) precancerous diseases. FIG. 4 shows the results obtained in these assays, indicating that in many GI disease and cancer tissues, especially in the colon, ARL-1 protein was undetectable. Interestingly, ARL-1 protein was also undetectable in some matched normal tissues, indicating genetic loss of ARL-1 protein in these patients (FIG. 4). These results are significant, because they suggest that ARL-1 loss may be a risk factor of GI cancer by leaving the GI cells vulnerable to dietary carbonyl carcinogens. Thus, ARL-1 can serve as marker useful for identifying individuals at risk for developing gastrointestinal cancer due to the loss of this protein protection against carcinogenic reactive carbonyls, particularly dietary carbonyls. These results also suggest that ARL-1 is a candidate for developing specific intervention agents that target to ARL-1, which will significantly prevent GI cancer.

Figure 5:
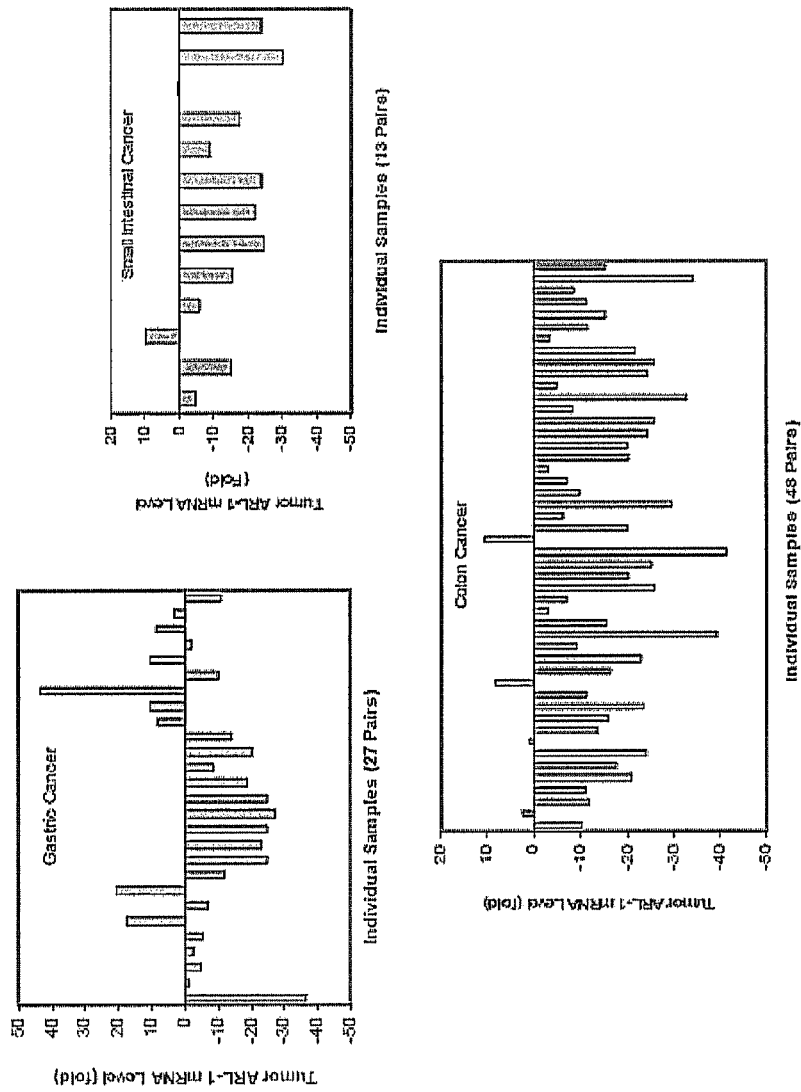
FIG. 5 is a graphical representation of the results of quantitative analysis of ARL-1 mRNA in gastric, colon, and small bowel tissues using real-time PCR. The results were expressed as fold of ARL-1 mRNA levels in tumor over in the matched normal tissue. Negative indicates decrease of mRNA in tumor tissues while positive indicates increase. In this study, only the tumor tissues with matched normal tissues were investigated.

ARL-1 gene expression was investigated using quantitative real-time PCR to determine mRNA levels of this gene in normal and colon cancer tissues. Real-time PCR was performed using ARL-1 specific primers according to the manufacturer's instructions (Applied Biosystems, CA). The primer and probes are commercially purchased from Applied Biosystems (Catalog number: Hs00252524_ml, Foster City, Calif.). In this study, only tumor samples with matched normal tissues were examined for the comparison purpose. The results are shown in FIG. 5 as the "fold" changes in ARL-1 mRNA levels. In this Figure, negative results reveal decrease of ARL-1 mRNA levels in colon cancer samples.

These results established that ARL-1 expression was reduced in a significant proportion of human gastrointestinal tumors and precancerous lesions, a result consistent with ARL-1's purported role in providing these tissues with protection from reactive carbonyl species.

Figure 6:
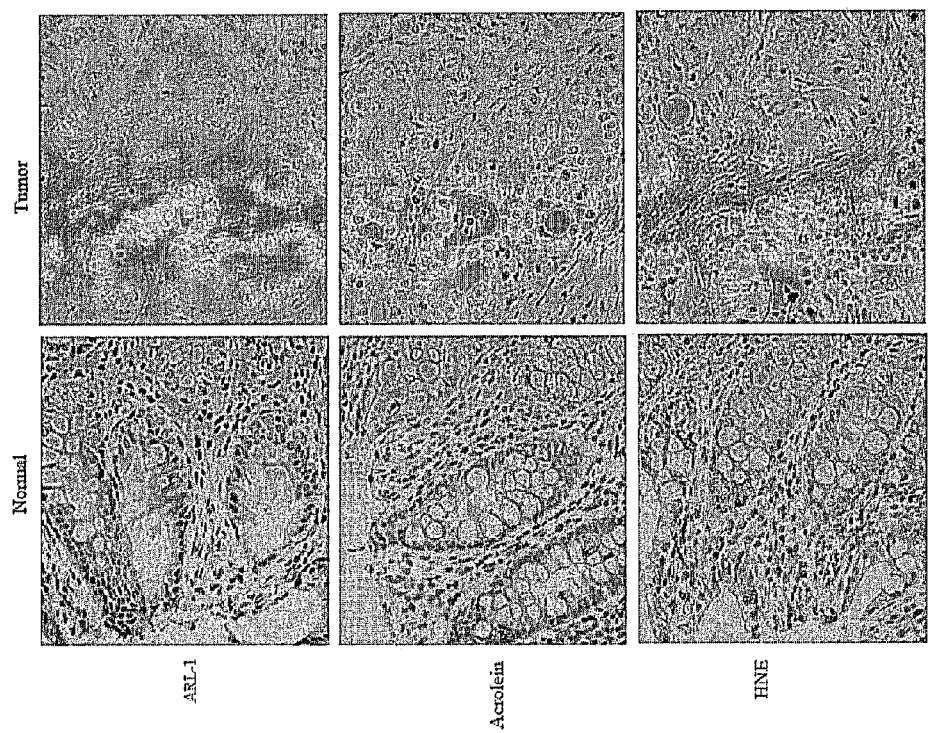
FIG. 6 is a photomicrograph of immunohistochemical analysis of ARL-1 expression and reactive carbonyl adduct formation in normal and colon tumor tissues. Both normal and tumor tissues were from the same cancer patient. Paraffin-embedded sections were used for immunohistochemistry study and assayed for ARL-1 expression and acrolein or 4-hydroxynonenal (HNE) adduct formation. Results indicated ARL-1 significantly prevents the formation of acrolein and HNE adducts. (20× objectives).

The existence of reactive carbonyl-protein adducts in normal and colon tumor tissues was assayed by immunohistochemistry. A role in cytoprotection for ARL-1 suggests that normal colon epithelium displaying ARL-1 activity would show the presence of little or no adducts formed between reactive carbonyls and cellular components (proteins and nucleic acids) compared with colon tumors, which would be expected to show adduct formation to a greater extent due to the loss of ARL-1. Immunohistochemical study of carbonyl adducts is an art-recognized method for detecting carbonyl-protein adducts (Suzuki et al., 1999, *J Am Soc Nephrol* 10:822-832). Accordingly, paired normal and colon tumor tissues were assayed using antibodies (obtained from Chemicon International, CA) against acrolein and 4-hydroxynonenal (HNE) adducts, respectively. These results are shown in FIG. 6, where acrolein and HNE adducts are detected in tumor tissues with reduced ARL-1 expression and not in normal colon epithelia. In paired normal and tumor tissue samples, ARL-1 was expressed in the epithelial cells of normal colon, which efficiently blocked the formations of acrolein and HNE adducts in these cells (arrows). However, in tumor tissue ARL-1 protein was undetectable in cancer cells, and consequently, acrolein and HNE adducts were formed at very high levels in the cells (arrows).

These results indicate that ARL-1 expression is associated with protection of normal colon epithelium from reactive carbonyl adduct formation, a protection lost in colon tumor cells.

Example 4

Analysis of ARL-1 Activity on Dietary-Associated Reactive Carbonyls and its Cellular Protection Enzymatic activity of ARL-1 toward reactive carbonyls were first measured using purified ARL-1 protein, by assaying oxidation of NADPH to NADP$^+$ as described in Cao et al. (1998, Id.). Michaelis-Menten constants ($K_m$ and $V_{max}$) were calculated with GraphPad Prism 4 (Graph Pad Software, CA). These results showed that ARL-1 has strong enzymatic activity to reactive carbonyls.

The capacity for ARL-1 to provide protection to gastrointestinal cells, and the consequences stemming from loss of such capacity, were assessed using an in vitro model system. Human HCT-8 cells, a colon cancer cell line, were purchased from the American Type Culture Collection (ATCC, Manassas, Va.) and grown and maintained in RPM1-1640 medium (Hyclone, Utah), supplemented with 10% fetal bovine serum (FBS), 2 mM glutamine, and 100 U/ml penicillin and 100 µg/mL streptomycin at 37° C., 5% $CO_2$.

To test for intracellular ARL-1 function, two small interfering RNAs (siRNAs) were designed and used to downregulate ARL-1 levels in cultured HCT-8 cells derived from human colon carcinoma. These siRNAs were targeted to encoding region (siRNA 1,5' GCAAGUUGUGGCCCACU-UUtt; SEQ ID NO: 2) and 3' untranslational region (siRNA 2,5'CGAGAAUCGAGGUGCUGUUtt; SEQ ID NO: 3), respectively, and were chemically synthesized (obtained from Ambion, Tex.). A randomly-scrambled siRNA was used as a negative control. For siRNA delivery, HCT-8 cells (3.5× $10^3$ to $10^5$ in Opti-MEM I medium) were mixed gently with siRNA and OligofectAMINE (Invitrogen, CA) in a total volume of 0.5~1.5 mL and then incubated at 37° C., 5% $CO_2$ for 4 hours, followed by an addition of equal volumes of fresh medium containing 20% FBS. Cells were allowed to incubate until harvest.

Figures 7A, 7B, 7C, 7D:
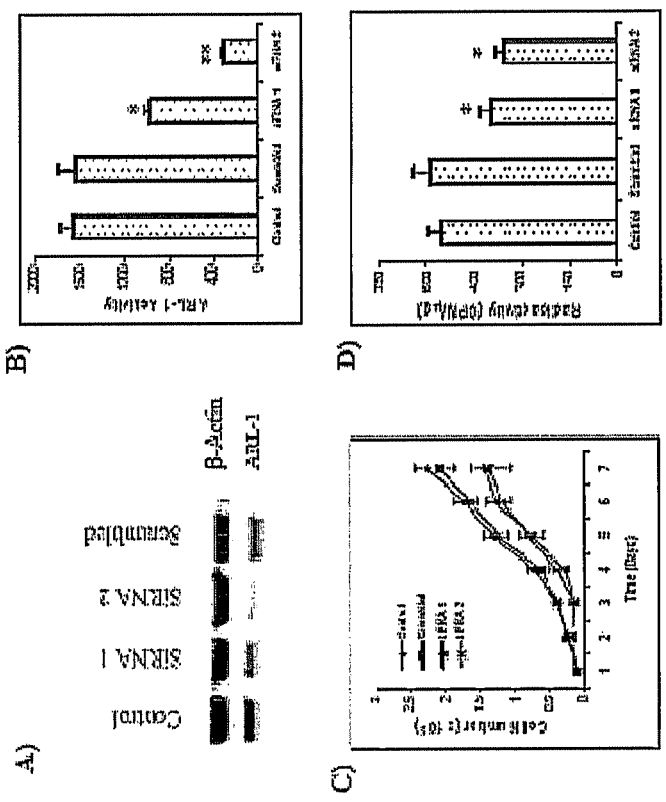
FIGS. 7A through 7D show the effects of ARL-1 knockdown on cell growth. An HCT-8 cell suspension ($3 \times 10^5$ cells) was mixed with siRNA (50 nM) and OligofectAMINE transfection reagent, and then spread into 24-well plates at $10^4$ cells/well for cell growth tests (FIG. 7C). The remaining cells were cultured in 6-well plates for Western blot analysis (FIG. 7A), enzymatic activity (nmoles/mg protein/hour.

The effects of siRNA inhibition of ARL-1 expression were assessed by Western blot analysis (results shown in FIG. 7A), ARL-1 activity (FIG. 7B), cell growth (FIG. 7C) and tritiated thymidine incorporation (FIG. 7D). Western blot analysis was performed as set forth above using the polyclonal antisera of this invention. These results correlated with a decrease in ARL-1 activity in these cells, as shown in FIG. 7B. These assays were performed by assaying oxidation of NADPH to $NADP^+$ as described in Cao et al. (1998, Id.). These results in FIGS. 7A and 7B showed a siRNA-specific decrease in ARL-1 protein and enzymatic activity, consistent with the other results shown herein. These results showed that both siRNA 1 and 2 (50 nM) specifically downregulated ARL-1 protein up to 60 and 95%, respectively.

Having successful reduced ARL-1 expression in these cells provided a cell model system for investigating the intracellular role of this protein in regulating carbonyl stress. Cell growth and DNA synthesis were assayed in cells having reduced ARL-1 expression caused by siRNAs. In cell growth experiments, $10^4$ cells per well were seeded into 24-well plates and incubated at 37° C., 5% $CO_2$ atmosphere and viable cells were counted by trypan blue exclusion staining. These results are shown in FIG. 7C. ARL-1 knockdown significantly inhibited HCT-8 cell growth rate by more than 30% compared to the control cells.

Tritiated thymidine incorporation was assayed as follows. Cells were pulsed with 10 µCi $^3$H-thymidine for 2 hours and then lysed in 15% trichloroacetic acid (TCA) on ice. After washing twice with 15% TCA, acidic-insoluble materials were completely dissolved in 0.1 N NaOH. An aliquot (10 µL) was used to determine protein amount and the remaining was subjected to radioactivity assay. $^3$H-thymidine incorporation was corrected by protein amount as described in Dake et al. (2004, *Endocrinology* 145: 3369-3374). These results are shown in FIG. 7D, where siRNA treated HCT-8 cells incorporated about 30% less tritium into cellular DNA than control cells.

Cytotoxicity comparisons were performed by exposing cells (with ARL-1 knockdown) to acrolein (25 µM) or crotonaldehyde (50 µM) for 72 hours. In these experiments, after the cells were incubated with carbonyl compounds the culture medium was gently removed, and cells were washed with cold PBS and trypsinized. Viable cells were counted by trypan blue exclusion staining.

The mechanisms of cell death induced by reactive carbonyls were investigated by flow cytometry and lactate dehydrogenase leakage assay. For flow cytometry assay, cells (with ARL-1 knockdown) were incubated with acrolein (25 µM) for 24 hours. After medium was gently removed, cells were washed with cold PBS and trypsinized. Cells in PBS and trypsin digestion were pooled, washed with PBS twice at 1200 rpm for 10 min, and then subjected to immediate propidium iodide (PI) and annexin V-FITC staining for 10 minutes in the dark as set forth in Yuan et al. (2004, *Oncogene* 23: 5843-5852, 2004). FACScan analysis was performed using a FACScan cytometer (Becton Dickinson, Calif.).

For lactate dehydrogenase (LDH) efflux assays, cells were plated at $5\times10^4$ cells/well in 12-well plates and exposed to 25 µM of acrolein for 12 hours. Medium was collected and cells were lysed for 10 min in 0.5% (v/v) Triton X-100 in 0.1 M potassium phosphate buffer (pH 7.4). Supernatants were collected by centrifugation at 10,000×g for 5 min. LDH activity in medium and cell lysates was measured using LDH assay kit (Roche, Ind.). Samples (100 µl each, diluted if necessary) were mixed with equal volumes of LDH reagent in 96-well plates. Three wells were prepared for each sample to obtain averages. After incubation at room temperature in the dark for 10 min, reactions were stopped by addition of 50 µl of 1 N HCl. Absorbance at 490 nm was read in a microplate reader (Bio-Rad, CA), with 650 nm as a reference wavelength. LDH release was calculated as: LDH release (%)=[LDH in medium/(LDH in medium+LDH in cell lysate)]×100 (Koh and Choi, 1987, *J Neurosci Methods* 20: 83-90).

The results showed that in HCT-8 cells with ARL-1 knockdown the cell death induced by acrolein was featured with LDH efflux and annexin V staining, a characteristic of oncosis.

Anchorage-independent growth in soft agar, an art-recognized characteristic of oncogenically transformed cells, was also assessed in ARL-1 siRNA-containing HCT-8 cells. In these experiments, 100 cells/well in a 24-well plate were suspended in 0.5 mL of 0.3% Noble agar (Sigma, Mo.) and layered over 0.5 mL of 0.5% agar in the same medium. After being cultured at 37° C., 5% $CO_2$ for 2 weeks, cell foci were photographed and scored under inverted microscope. Clonogenic efficiency was calculated as: clonogenic efficiency (%)=(number of clones/number of seeded cells)×100 (Li et al., 2004, *Cancer Res.* 64: 7058-7064).

Figure 8A:
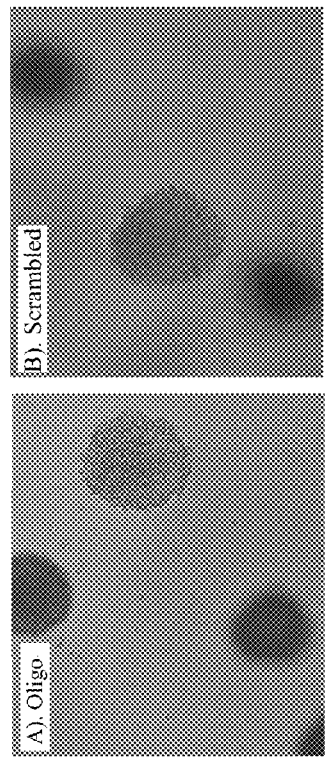
FIGS. 8A and 8B show photomicrographs of anchorage-independent growth of HCT-8 cells. HCT-8 cells were transfected with siRNA (50 nM) as described in Example 4 and grown in soft agar. Two weeks later, formed foci were photographed (FIG. 8A) and scored (FIG. 8B). Values in FIG. 8B represent mean±SD from three independent experiments.
Figure 8B:
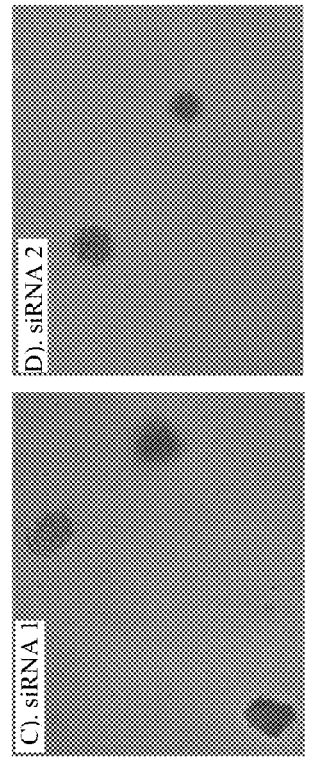

The results of these experiments are shown in FIGS. 8A and 8B. The ARL-1 knockdown dramatically reduced the viability and clonogenic growth of HCT-8 cells. Focus formation rate and size of HCT-8 cells with ARL-1 knockdown were significantly reduced compared with controls. These result support the evidence set forth herein that ARL-1 protected cells from endogenous carbonyl lesions.

To verify phenotypic specificity to ARL-1, an EGFP/ARL-1 fusion protein was transiently expressed in 293T cells to assess cell response to acrolein exposure. 293T cells were purchased from American Type Culture Collection, grown and maintained in DMEM medium supplemented with 10% fetal bovine serum (FBS), 2 mM glutamine, and 100 U/ml penicillin and 100 µg/mL streptomycin at 37° C., 5% $CO_2$. In these experiments, a eukaryotic expression vector of EGFP/ARL-1 fusion protein was constructed by inserting ARL-1 cDNA (Cao et al., 1998, Id.) into the expression plasmid EGFP-C3 (Promega, Wis.) at Pst I and Apa I sites in the vector.

Plasmid DNA was isolated and delivered into 293T cells using LipofectAMINE, following manufacturer's instruction (Invitrogen, CA).

Figures 9A, 9B, 9C:
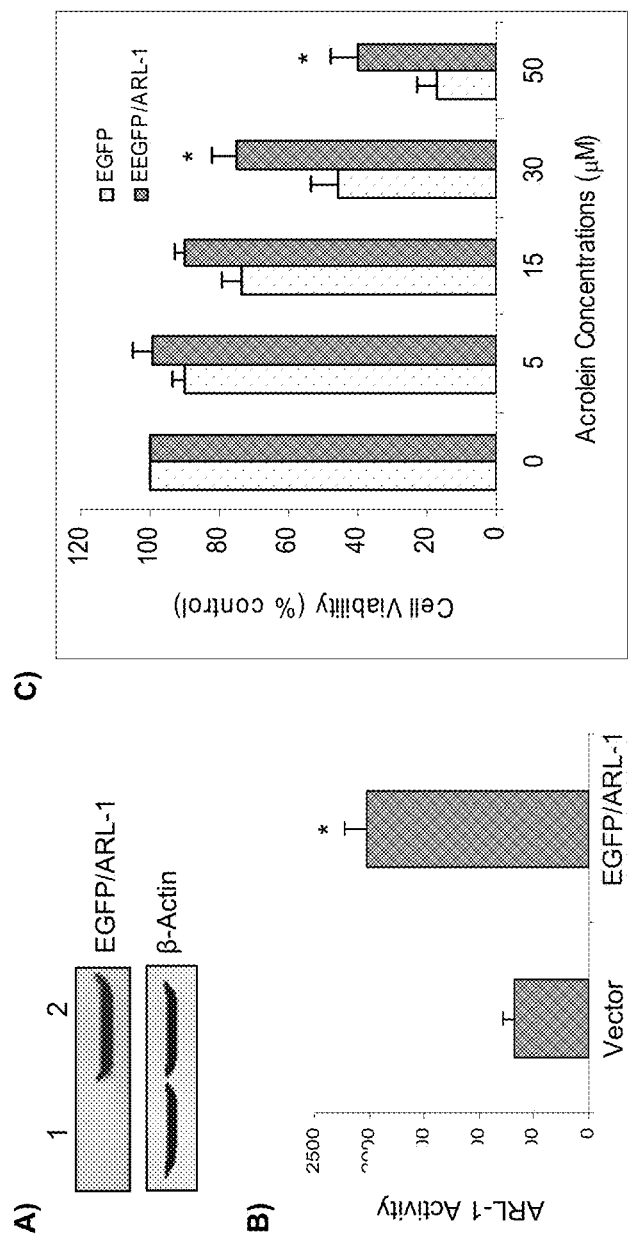
FIGS. 9A through 9C show protection by ARL-1 of 293T cells from acrolein toxicity. 293T cells were harvested for Western blot (FIG. 9A) and ARL-1 activity assays (nmol/mg protein/hour) (FIG. 9B) 36 hours after transfection with EGFP (control) or EGFP/ARL-1 plasmid DNA. For acrolein cytotoxicity tests, cells ($3 \times 10^3$) were spread into 96-well plates 24 hours after transfection. The next day, cells were fed with fresh medium containing acrolein at concentrations as indicated. Viable cells were evaluated by MTT kit (Roche, Ind.) following manufacturer's instructions. Results were expressed at percentage of control (FIG. 9C). Values in FIGS. 9B and 9C represent mean±SD from three independent experiments. * indicates statistical significance ($P<0.05$), compared to EGFP vector control. Lane 1, EGFP vector control, and lane 2, EGFP/ARL-1 fusion protein

The results of these experiments are shown in FIGS. 9A through 9C. EGFP/ARL-1 fusion protein was successfully expressed in 293T cells as shown by Western blot analysis in FIG. 9A. Cells containing these constructs had strong ARL-1 activity, indicating functionality of this fusion protein. Using these ARL-1 transferred cells, the cellular response to acrolein, administered at concentrations ranging from 5-50 µM, was assessed. A comparison between cells overexpressing ARL-1 and vector cells indicated that ARL-1 was capable of protecting cells from acrolein cytotoxicity at the concentrations tested (FIG. 9C).

Figure 10:
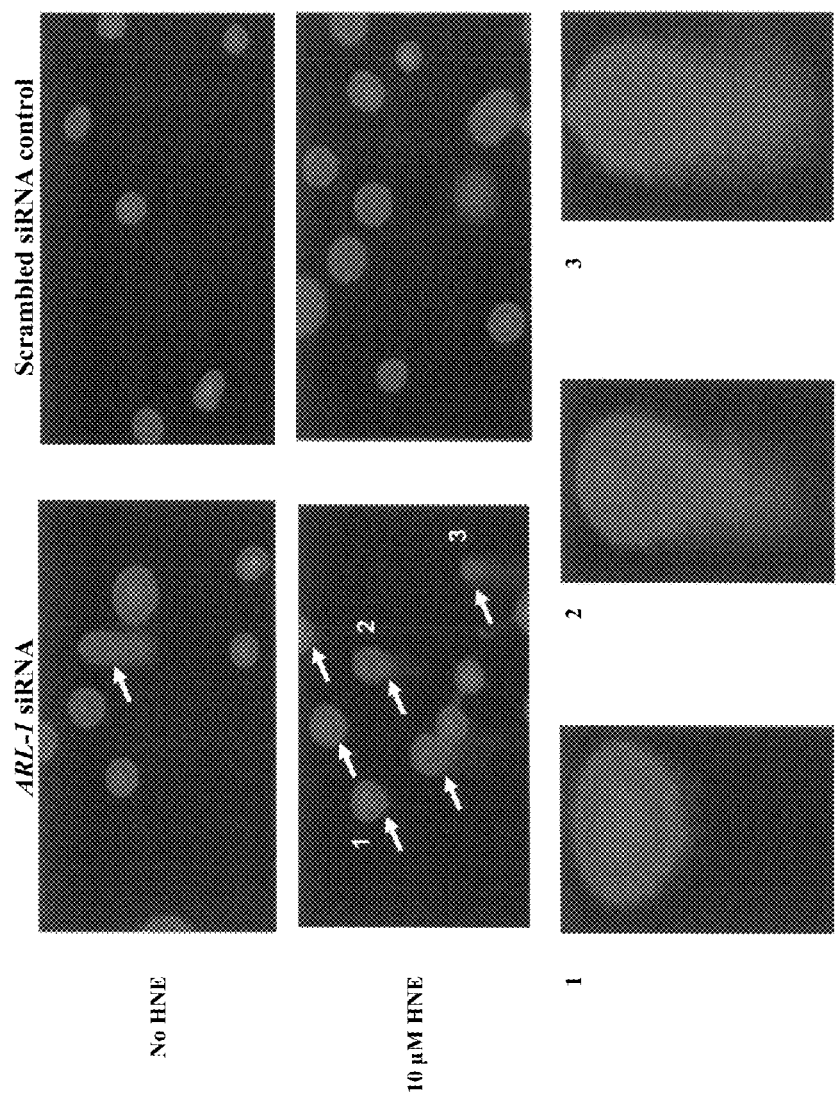
FIG. 10 shows the results of comet assays for DNA breaks in HCT-8 cells with ARL-1 gene silencing. Results indicate that ARL-1 silencing led to DNA breaks (arrow, top panel). When the ARL-1 silenced cells were exposed to FINE, DNA breaks were dramatically increased (arrows, middle panel). Length and shape of comet tails reflect extent of DNA breaks (bottom panel).

Another assay for the capacity of reactive carbonyl species to have deleterious effects on colon epithelial cells detects the presence of DNA breaks in these cells, a well-known factor of cell carcinogenesis. 4-hydroxynonenal (HNE) exposure was performed by incubating HCT-8 cells with 50 µM FINE in serum free medium for 1 hour, followed by incubation for 12 hours in regular medium containing 10% FBS. Comet assay was used for detection of the DNA breaks. These results indicated that silencing of ARL-1 resulted in DNA breaks and the DNA breaks were dramatically enhanced when exposed to FINE (FIG. 10). These data indicate the critical role of ARL-1 in protecting HCT-8 cells from DNA breaks that occurred automatically or are induced by HNE.

These results established that ARL-1 has the capacity to detoxify reactive carbonyl species in vitro and in vivo and that loss of function for this enzyme is associated with reduced growth and cell death. These results are also consistent with loss of function existing in a significant proportion of precancerous lesions and cancers in the gastrointestinal tract, and thus provide a target for diagnostic and chemopreventive interventions.

Example 5

Analysis of ARL-1 Function on Drug Resistance of Cancer

Figure 11A:
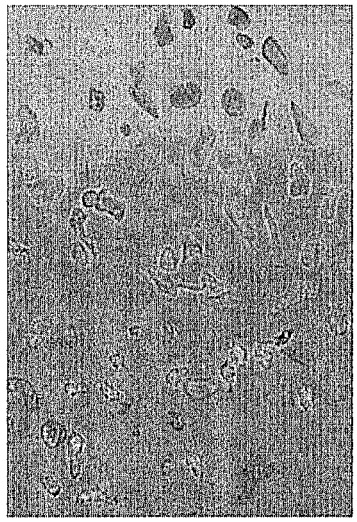
FIG. 11 shows the results of immunohistochemistry of human hepatocellular carcinoma using the anti-ARL-1 antibodies of the invention. Frozen sections of a human hepatocellular carcinoma tissue was stained with the specific ARL-1 antibody (A) (Arrow). An adjacent section was used for negative control (B), in which ARL-1 primary antibody was replaced by PBS. Hematoxylin counter staining was used to demonstrate nuclei.
Figure 11B:
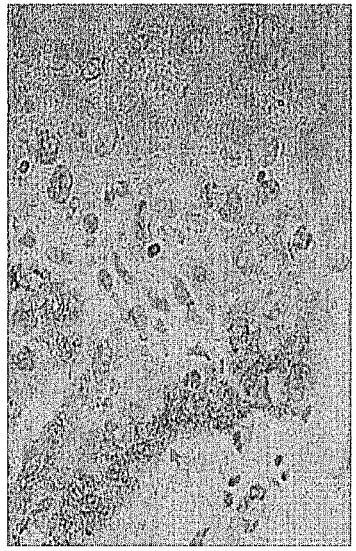

ARL-1 is a strong protein enzyme toward carbonyls, by reducing the carbonyl groups. Many anticancer agents contain active carbonyl group, such as anthracyclines (daunorubicin and doxorubicin). Therefore, ARL-1 may be implicated in the drug resistance of cancer cells that overexpress this protein, such as hepatocellular carcinoma (HCC; Cao et al., 1998, *J Biol. Chem.* 273: 11429-11435) and lung cancer (Fukumoto et al., 2005, Id.). Immunohistochemistry was performed on frozen sections of HCC tissues, using the specific ARL-1 antibodies of the invention, and showed high expression of ARL-1 protein in hepatocellular carcinoma tissues (FIGS. 11A and 11B).

Biochemical experiments were performed to assess the biological activity of purified recombinant ARL-1 protein in detoxifying daunorubicin to its alcohol form, daunorubicinol. In this study, ARL-1 protein (2 μg/mL) was incubated with 10 mM daunorubicin at 30° C. for 20 min, in the presence of 0.2 mM NADPH, 0.4 M $Li_2SO_4$, and 135 mM sodium phosphate (pH 6.4). Enzymatic products were analyzed with a liquid chromatography-mass spectrometry. Briefly, the reaction mixture was filtered with a 5 kD filter to remove proteins and other macromolecules, and then diluted with acetonitrile (1:3). After being well mixed, this solution was further diluted with 5 mM ammonium acetate/acetonitrile. Daunorubicin and its enzymatic product (marked as X in FIGS. 12A and 12 B) were separated and characterized using reversed-phase high-performance liquid chromatography (HPLC) with electron spray ionization tandem mass spectrometry (LC-MS).

Figure 12A:
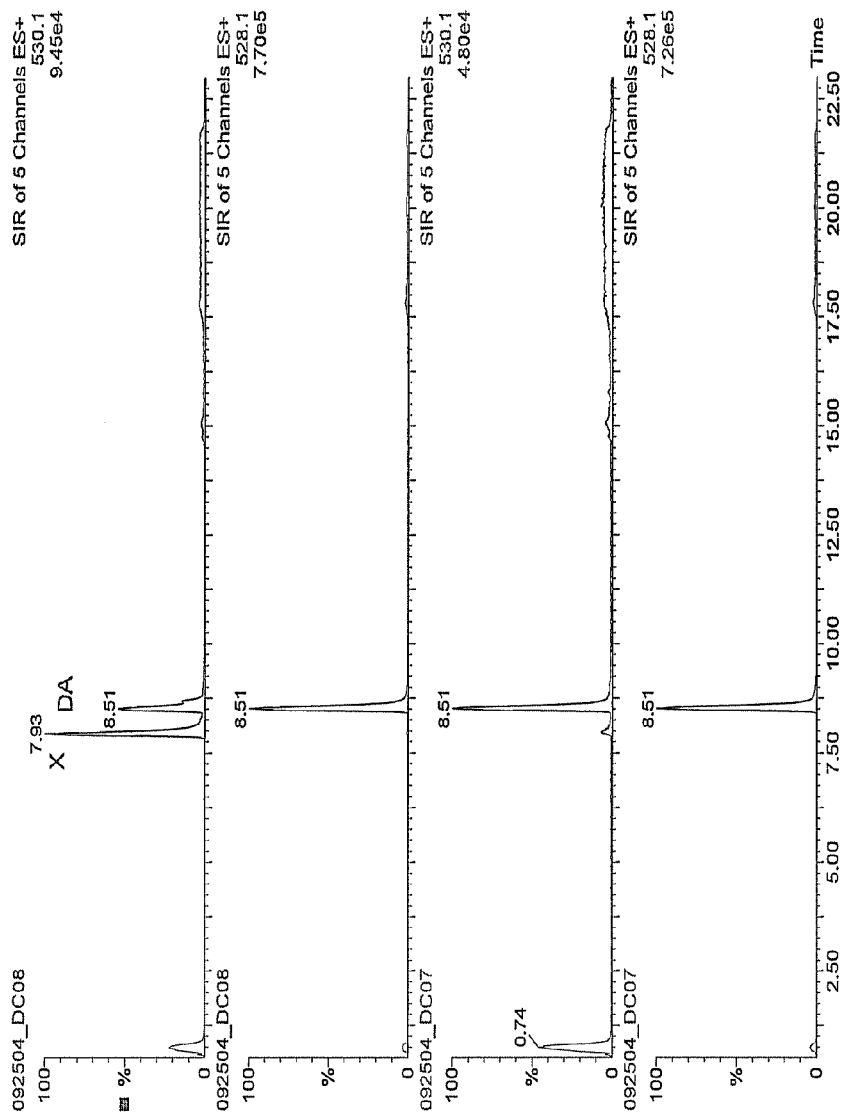
FIG. 12A shows the results of LC-MS analysis of daunorubicin analytes in a reaction mixture with purified, recombinant ARL-1 protein to assess the biological activity of recombinant ARL-1 protein. Small molecule metabolites were assays using selective ion recording (SIR) mode monitoring ion transitions. A peak with m/z 530.1 in daunorubicin (DA) and ARL-1 reaction mixture (two upper traces) is 30 times higher than that in daunorubicin control (two lower traces).
Figure 12B:
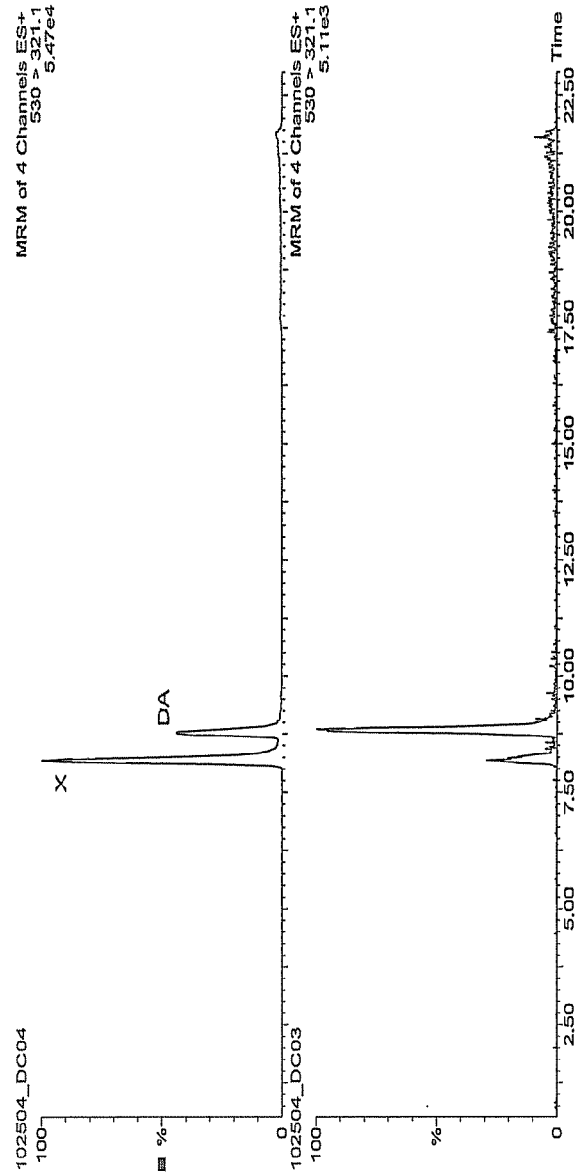
FIG. 12B shows the results of multiple reaction monitoring (MRM) mode monitoring ion transitions to confirm the existence of reduced product of daunorubicin. This different monitoring method confirms the presence of reductive product with m/z 530.1 (top, reactants), compared with its parental mass 528.1 (lower, control).

The instrument used was a micromass triple quadrapole mass spectrometer (Waters, Milford, Mass.), operated in a positive ionization mode with a unit mass resolution. Resulting ions were first monitored using the selective ion recording (SIR) mode (FIG. 12A). Ion transitions, m/z 528.1 ($MH^+$) to 321.1 and 530.1 to 321.1 or 323.1, were monitored in multiple reaction monitoring (MRM, second order MS) mode (FIG. 12B). Capillary and cone voltages were set at 4.3 kV and 33 V, respectively. Source and desolvation temperatures were 120° C. and 325° C., respectively. Electron spray gas was provided with a high pressured liquid nitrogen tank. For MRM, argon of ultra high purity was used as the collision gas. A Waters HPLC system (Waters, Milford, Mass.) with a reversed phase, C18 column 2×50 mm was used, at a flow rate of 0.2 ml/min. Chromatographic separation was carried out with a gradient elution, from 5% to 95% acetonitrile for 20 min.

FIG. 12A shows the results from SIR analysis. Two upper traces from the reaction mixture of daunorubicin and ARL-1 show an ion ratio (530.1/528.1) for daunorubicin of approximately 6.63%, which is in agreement with the ratio of 6.61% shown in two lower traces from the control of daunorubicin alone (without ARL-1). It is important to note the peak with a retention time of 7.93 min (marked with X in FIGS. 12A and 12B). This peak is only present in the daunorubicin reactant sample, and is well separated from daunorubicin's peak, which has retention time of 8.51 min. This peak is only detectable with m/z 530.1 (indicating addition of two hydrogen protons), and its amount in the daunorubicin reactant sample is approximately 30 times more in height than in the daunorubicin control. This data indicates that this peak, with m/z 530.1, may represent the reduced products of daunorubicin (m/z 528.1).

This hypothesis was confirmed using an additional MRM analysis. FIG. 12B displays the presence of the reduced products with an ion transition of 530.1 to 321.1, showing the same amount of increase (approximately 30 times) in the daunorubicin and ARL-1 mixture (upper panel), compared to the daunorubicin control (lower panel). Furthermore, m/z 530.1 gives an ion transition of 321.1, rather than 323.1 (FIG. 12B), indicating that this reduction occurred on the $C_{13}$ ketone group ($COCH_3$) of daunorubicin, producing daunorubicinol. In view of the stronger cardiotoxicity of daunorubicinol rather than its antitumor activity, this finding may imply that the tumor-specifically induced ARL-1 may not only result in tumor drug resistance, but also contribute to cardiovascular side effects.

These results indicated that ARL-1 overexpressed in hepatocellular carcinoma can catalyze the reduction of daunorubicin, one of anthracyclines with C13 ketonic group, to its alcohol form, daunorubicinol. Daunorubicinol, and also, the alcohol forms of other anthracyclines have less antitumor activity but strong cardiovascular toxicity. Therefore, cancer with ARL-1 overexpression is unlikely to be suitable for treatment of anthracyclines, and it would be advantageous for patients to screen ARL-1 expression before beginning a fruitless course of chemotherapy.

Figure 13:
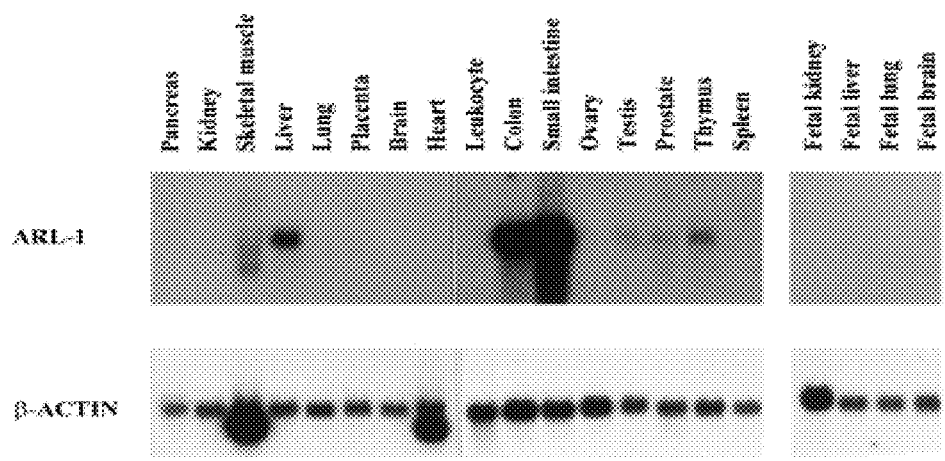
FIG. 13 is a photograph of Western blot analysis detecting ARL-1 protein in normal tissue samples. In normal tissues, ARL-1 protein was expressed at high levels in colon and small intestine and relatively lower levels in prostate, liver and lung.

ARL-1 is expressed at high levels in normal small intestine and colon, and expression was significantly decreased in colon cancer. The levels of ARL-1 were examined in other normal GI-tract tissues as well as normal non-GI tract tissues by Western blot analysis using ARL-1-specific polyclonal antisera described in Example 2. As shown in FIG. 13, ARL-1 was expressed at high levels in normal colon and small intestine, and at much reduced levels in normal liver, lung, and prostate tissues. The levels of ARL-1 in normal, cancer or precancerous lesions of the prostate and breast tissues were investigated and the results will be described in the following examples.

Example 6

Tissue Microarray Analysis of ARL-1 Expression in Prostate Cancer

A tissue microarray from Cibrdi, Inc. (Rockville, Md.) containing normal and prostate cancer tissues was examined by immunohistochemistry with an ARL-1-specific antibody as described in Example 2. ARL-1 expression in 67 prostate cancer tissues was evaluated and the results summarized in Table 1. ARL-1 protein was detected positive in 10 (14.9%) and strongly positive in 28 (41.8%) of 67 prostate cancer samples (Table 1).

TABLE 1

| Tumor | ARL-1 (n = 67) | | |
|---|---|---|---|
| AJCC Stages* | Negative | Positive | Strongly Positive |
| I (n = 23) | 10 | 3 | 10 |
| II (n = 26) | 13 | 4 | 9 |
| III (n = 10) | 4 | 2 | 4 |
| IV (n = 8) | 2 | 1 | 5 |
| Subtotal (%) | 29 (43.3) | 10 (14.9) | 28 (41.8) |

*AJCC staging: American Joint Committee on Cancer (AJCC) staging system.

Representative images of immunohistochemistry using ARL-1-specific antibodies are shown in FIG. 14. The results demonstrated that ARL-1 was undetectable in normal prostate (FIG. 14A), and was overexpressed in prostate tumors (FIGS. 14B and 14C) and prostate hyperplasia (FIG. 14D).

Example 7

1. Tissue Microarray Analysis of ARL-1 Expression in Breast Cancer

Five breast cancer tissue microarrays (TMA) were investigated throughout the following studies: (1) YTMA-23 (Yale Tissue Microarray-23) containing 246 breast cancer cases with complete clinical records and nearby 30 years' follow-up (Table 2); (2) YTMA-89 consisting of 54 recurrent breast cancer cases; (3) YTMA-77 composed of 81 ductal carcinoma in situ (DCIS), (4) an array containing 50 breast cancer with matched metastatic lymph nodes (BR10010; Biomax, Md.), and (5) an array of 63 breast cancer (CC08-01-006; Cybrdi, Md.). Normal breast tissues were included in all TMAs as an internal control.

ARL-1 (AKR1B10) in normal and cancerous breast tissues was examined by immunohistochemistry. Briefly, after dewaxing and hydration, tissue microarray slides were immerged in preheated citric acid buffer (pH 6.5) at 90-95° C. for 20 min microwaving with intervals. It is a standard procedure for antigen retrieval. The slides were blocked with 5% horse serum for 30 min, and were incubated with the ARL-1-specific rabbit polyclonal antibody (1:2-5 dilutions) as described in Example 2 at 4° C. in a humid box overnight. Thereafter, slides were washed 3 times and then incubated with HRP conjugated secondary antibody (1:800; Pierce, Ill.) at room temperature for 1 hour. Enhanced DAB staining buffer (Pierce, Ill.) was used to visualize signals. Staining intensity was evaluated blindly by at least a researcher and a pathologist using a classification from '0' to '3', representing no staining ('0'), low staining ('1'), intermediate staining ('2'), or high staining intensity ('3'), respectively.

Descriptive statistics were examined for all variables. Given the distributional characteristics of the variables, non-parametric statistical tests were employed to examine the relationships between ARL-1 expression and the other variables. Specifically, Spearman rank correlation coefficients were used to assess the relationship between ARL-1 (AKR1B10) expression and continuous or ordinal variables, while Wilcoxon rank-sum tests or Kruskal-Wallis tests were utilized with categorical variables. Additionally, Kaplan-Meier survival curves were produced to examine the relationship between ARL-1 expression and mortality. The log-rank test was used to test for differences between the survival curves. Cox proportional hazard regression model was employed in multivariate analysis. Results were considered statistically significant for $p<0.05$. Table 2 summarizes the ARL-1 expression in different breast cancer TMAs.

TABLE 2

| Tissue Microarrays | Description | Interpretable Cases/tTotal cases | ARL-1 expression levels (%) | | | |
|---|---|---|---|---|---|---|
| | | | 3 | 2 | 1 | 0 |
| YTMA-23 | Breast Cancer | 220/246 | 33 (15.0) | 69 (31.4) | 82 (37.3) | 36 (16.4) |
| YTMA-89 | Recurrence | 32/54 | 3 (9.4) | 10 (31.3) | 15 (49.6) | 4 (12.5) |
| YTMA-77 | DCIS | 28/81 | 4 (14.3) | 6 (21.4) | 10 (35.7) | 8 (28.6) |
| CC08-01-006 | Breast Cancer | 61/63 | 11 (18.0) | 20 (32.8) | 21 (34.4) | 9 (14.8) |
| BR10010 | Breast Cancer with self-paired Metastasized Lymph Nodes | 50/50 | 8 (16.0) | 14 (28.0) | 21 (42.0) | 7 (14.0) |

As shown in Table 2, among all the interpretable cases, about 85% of breast cancer tissues, about 87.5% of recurrent breast cancer tissues, about 86% of metastasized lymph nodes, about 71% of DCIS showed detectable ARL-1 staining.

2. ARL-1 was Overexpressed in Invasive Breast Cancers

Figure 15:
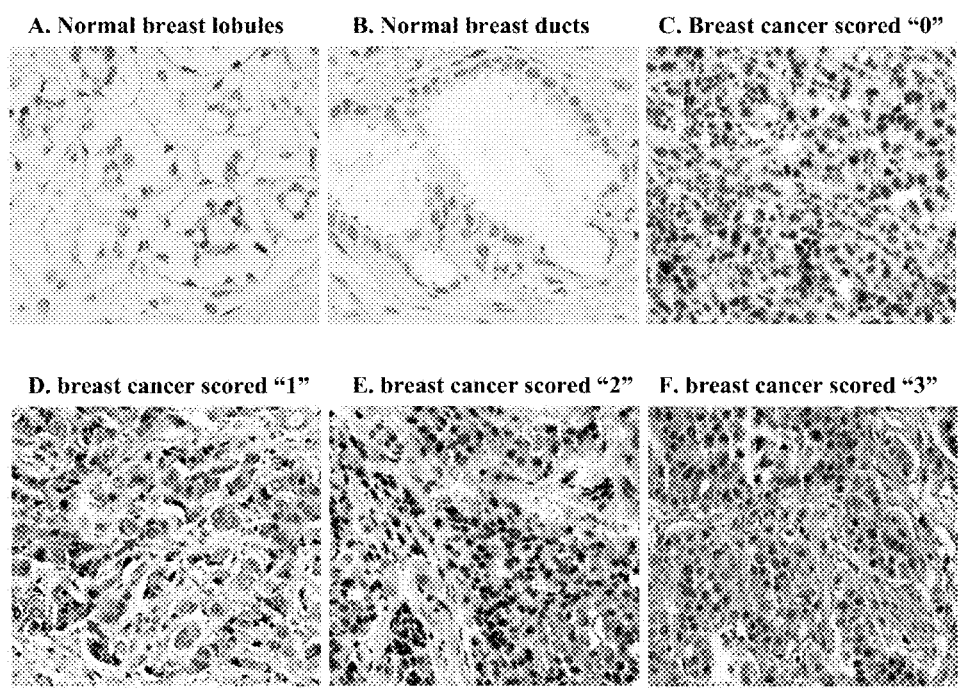
FIGS. 15A-F are photomicrographs of immunohistochemistry stained with ARL-1 antibody in tissues of normal breast lobules (FIG. 15A), normal breast ducts (FIG. 15B), and breast cancers scored at '0' (FIG. 15C), '1' (FIG. 15D), '2' (FIG. 15E), and '3' (FIG. 15F), respectively.

Tissue microarray YTMA-23 consisted of 6 normal and 246 cancerous breast tissues from different patients, in which 4 normal and 220 malignant high quality tissue sections were evaluated for ARL-1 (AKR1B10) expression. The results showed that ARL-1 was undetectable in normal breast lobules and ducts (FIGS. 15A and 15B), but detectable in 184 out of 220 (83.6%) breast cancer tissues, scored at '1' to '3' based on the intensity of ARL-1 staining (FIGS. 15D-15F). The results were reviewed blindly by a researcher and a pathologist. Similar results were obtained from another tissue microarray (CC08-01-006), where 52 of 61 (85.2%) breast cancer tissues were stained positively for ARL-1.

2. ARL-1 was Expressed in Hyperplasia of the Breast

ARL-1 expression in hyperplasia of the breast (NC08-11-001) (FIG. 16A) was investigated. As summarized in Table 2, ARL-1 was detected in 6 of 10 (60%) hyperplasia, indicating that ARL-1 induction can be an early event in breast cancer development.

3. ARL-1 was Expressed in Ductal Carcinoma in Situ (DCIS) and Metastatic and Recurrent Breast Tumors ARL-1 expression in ductal carcinoma in situ (YTMA-77) and metastatic and recurrent breast tumors (FIGS. 16B-16D) was investigated for its role in the development and progression of breast cancer. As summarized in Table 2, ARL-1 was detected in 20 of 28 (71.4%) interpretable ductal carcinoma in situ, in 43 of 50 (86.0%) metastasized lymph nodes, and in 16 of 27 (87.5%) recurrent tumors.

4. ARL-1 Overexpression Positively Correlated with Tumor Size, Metastasis and Recurrence YTMA-23 tissue microarray contained samples from patients whose complete clinical and follow-up records were available. Samples from 220 of such breast cancer cases were examined and analyzed for the correlation between ARL-1 expression and other clinicopathological parameters. As shown in Table 3, ARL-1 expression positively correlated with tumor size (p=0.0012), lymph node metastasis (p=0.0123) and recurrence (p=0.0116), but not with patient age, tumor type, and nuclear grade. Data showed that the tumors with ARL-1 expression scored as '3' were approximately 1.3 fold larger than those scored '1' and 1.6 fold larger to those scored '0'. In 184 patients with an ARL-1 positive tumor, 112 (60.9%) had regional node metastasis, compared to a lower regional metastasis rate of 22.2% (8 of 36) of ARL-1 negative patients. ARL-1 expression also impacted tumor recurrence. The data indicated that 48 of 184 (26.1%) ARL-1 positive tumors recurred compared to a lower recurring rate of 8.3% (3 of 36) of ARL-1 negative tumors. In addition, tumors with distant metastasis had an ARL-1 expression levels 1.37 fold higher than the ARL-1 expression levels of tumors without distant metastasis (p=0.0470) and 1.50 times higher than those of tumors without any lymph node metastasis (p=0.0210). Similarly, the tumor ARL-1 level was 1.46 fold higher in breast cancer-related deaths than in disease-free survival (p=0.0140). Immunohistochemistry results showed strong ARL-1 staining in recurrent breast cancer (FIG. 16C) and lymphatic metastasis (FIG. 16D). Taken together, the data demonstrated that ARL-1 levels positively correlated with breast tumor size, recurrence and metastasis, and negatively correlated with patient survival.

Estrogen receptor (ER), Progesterone receptor (PR) and human epidermal growth factor receptor 2 (HER-2) are well-established biomarkers and therapeutic targets for breast cancer. Using Kruskal-Wallis tests, the correlation of ARL-1 expression with these three molecular markers was examined. The results showed that ARL-1 expression did not correlate with ER, PR or HER-2, alone or in any combinations (Table 3).

TABLE 3

Correlation of ARL-1 expression with clinicopathological parameters.

| Variables | ARL-1 (n = 220) | | | | p-value |
|---|---|---|---|---|---|
| | 3 | 2 | 1 | 0 | |
| Subtotal | 33 (15.0) | 69 (37.3) | 82 (37.3) | 36 (16.4) | |
| Age (years) | | | | | |
| Mean (range) | 58.3 (33-79) | 57.8 (35-86) | 61.3 (24-83) | 60.7 (33-83) | 0.5534 |
| >50 (%) | 22 (12.9) | 57 (33.5) | 69 (40.6) | 22 (13.0) | |
| ≤50 (%) | 11 (22.0) | 12 (24.0) | 13 (26.0) | 14 (28.0) | |
| Tumor Type | | | | | |
| Collid (%) | 0 | 2 (22.2) | 4 (44.4) | 3 (33.3) | 0.6730 |
| Ductal (%) | 19 (21.8) | 27 (31.0) | 34 (39.1) | 5 (5.7) | |
| Lobular (%) | 2 (6.1) | 13 (39.4) | 15 (45.5) | 3 (9.1) | |
| Tumor Size (cm$^3$) | | | | | |
| Mean (range) | 2.8 (0.8-7.0) | 2.8 (0.7-8.0) | 3.7 (0.5-14.5) | 2.5 (0.4-5.5) | 0.0012 |
| >2 (%) | 21 (15.3) | 36 (26.3) | 62 (45.3) | 18 (13.1) | |
| ≤2 (%) | 12 (14.5) | 33 (39.8) | 20 (24.1) | 18 (21.7) | |
| Recurrence | | | | | |
| Yes (%) | 12 (23.5) | 15 (29.4) | 21 (41.2) | 3 (5.9) | 0.0116 |
| No (%) | 22 (13.0) | 54 (32.0) | 61 (36.1) | 32 (18.9) | |
| Node Metastasis | | | | | |
| Positive (%) | 20 (16.9) | 39 (33.1) | 51 (43.2) | 8 (6.8) | 0.0123 |
| Negative (%) | 13 (12.9) | 30 (29.7) | 31 (30.7) | 27 (26.7) | |
| Nuclear Grade | | | | | |
| 1 (%) | 3 (10.7) | 8 (28.6) | 8 (28.6) | 9 (32.1) | 0.0822 |
| 2 (%) | 16 (13.9) | 38 (33.1) | 49 (42.6) | 12 (10.4) | |
| 3 (%) | 14 (20.0) | 22 (31.4) | 24 (34.3) | 10 (14.3) | |
| ER | | | | | |
| Positive (%) | 18 (16.4) | 35 (31.8) | 40 (36.4) | 17 (15.5) | 0.8680 |
| Negative (%) | 15 (13.6) | 34 (30.9) | 42 (38.2) | 19 (17.3) | |
| PR | | | | | |
| Positive (%) | 13 (13.1) | 31 (31.3) | 37 (37.4) | 18 (18.2) | 0.4143 |
| Negative (%) | 20 (16.5) | 38 (31.4) | 45 (37.2) | 18 (14.9) | |
| HER-2 | | | | | |
| Positive (%) | 20 (14.4) | 44 (31.7) | 50 (36.0) | 25 (17.9) | 0.6871 |
| Negative (%) | 13 (16.0) | 25 (30.9) | 32 (39.5) | 11 (13.6) | |

5. ARL-1 was Expressed in Metastatic Lymph Nodes and Recurrent Tumors

Tissue microarrays BR10010 (metastasis) and YTMA-89 (recurrence) were examined to analyze the expression of ARL-1 in metastatic lymph nodes and recurrent breast tumors. In the BR10010 microarray, 50 primary breast cancers were matched with the metastatic lymph nodes. The results showed that, similar to the primary tumors, ARL-1 was also detected in the metastatic tumors in the lymph nodes, with a correlation to the primary breast tumors r=0.45 (p=0.0180).

ARL-1 was also detected in 28 of 32 (87.5%) recurrent breast tumors. Among patients who received radiotherapy after first diagnosis of breast cancer, 13 developed recurrent breast tumors and all 13 recurrent breast rumors were ARL-1-positive. This rate was even higher than the rate of detection of ARL-1 in primary tumors (p=0.0290). Similarly, ARL-1 was detected in 5 out of 7 patients with recurrent breast tumors who received chemotherapy, and 7 out of 8 patients with recurrent tumors who received hormone therapy.

6. ARL-1 Overexpression Negatively Correlated with Patient Survival

Figure 17:
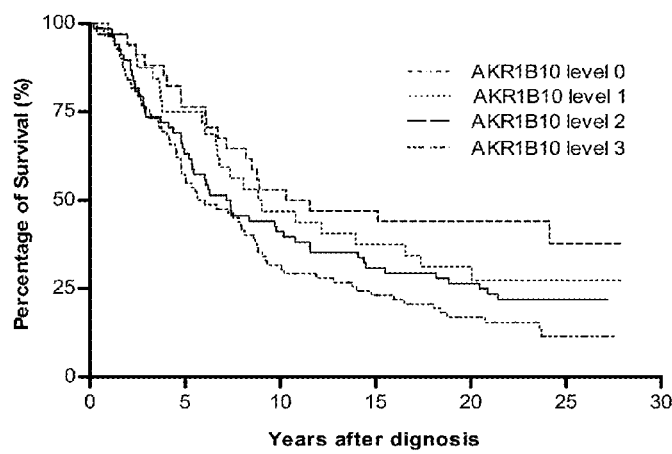
FIG. 17A shows Kaplan-Meier analysis of AKR1B10 (ARL-1) expression and survival (n=220, p=0.0026), the results of which are summarized in FIG. 17B.
FIG. 17C shows Kaplan-Meier analysis of AKR1B10 expression and disease-related survival (n=109, p=0.0120). Data were collected from breast cancer tissue microarray YTMA-23, which consisted of 220 interpretable breast cancer cases with more than 30-year's of follow-up. In disease-related survival analysis, only patients who died from breast cancer or disease-free survivals were counted.
Figure 17:
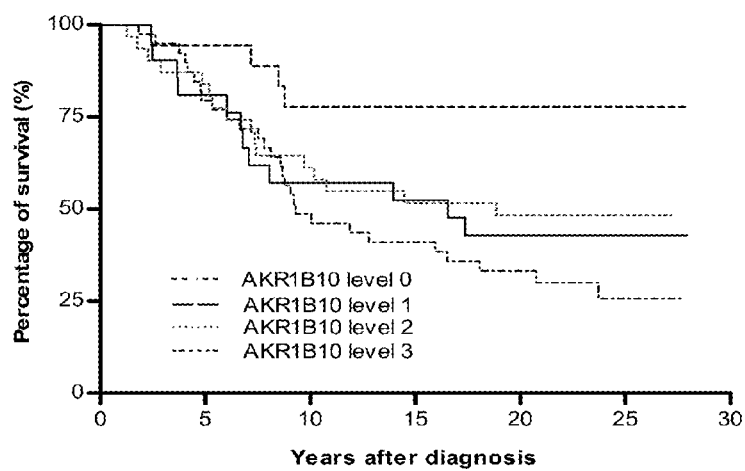

The correlation of ARL-1 expression in tumors and tumor size and lymph node metastasis led to the investigation of the effect of its expression on patient survival. Kaplan-Meier analysis showed that increasing ARL-1 expression was negatively associated with overall patient survival (n=220, p=0.0026) (FIGS. 17A and 17B) and in particular, disease-related survival (n=109, p=0.0120) (FIG. 17C), suggesting that ARL-1 can be used as a negative prognostic marker for breast cancer.

Figure 18:
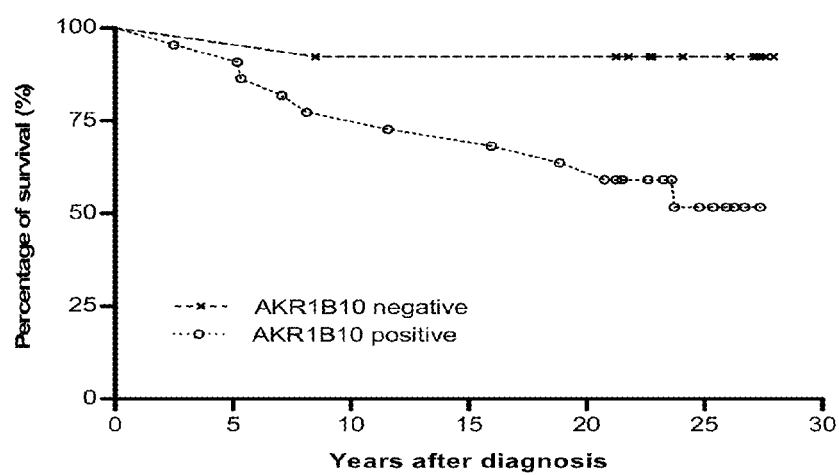
FIG. 18 shows Kaplan-Meier analysis of disease-related survival of early stage breast cancers (p=0.0270). Data were collected from YTMA-23, in which 35 patients were diagnosed at the early stage (tumor size<2 cm$^3$ and lymph node metastasis negative) and were analyzed for survival as a function of AKR1B10 (ARL-1) expression.

A correct intervention for breast cancer at early stages in order to avoid over-treatment is important for patient survival. Prognostic markers for early staged diseases are critical for the design of a balanced treatment strategy. In the data pool presented here, 35 patients had a tumor<2 cm$^3$ without node and distant metastasis and thus were designated as breast cancer at stage I (early stage) according to TNM (primary tumor size, node metastasis and distant metastasis) classification. ARL-1-related survival analysis indicated that patients with an ARL-1-negative tumor had much better survival rate than those with an ARL-1-positive tumor (p=0.0270) (FIG. 18). The data suggest that ARL-1 may be a prognostic marker for breast cancer at early stages, providing physicians with valuable information for designing an effective disease treatment plan for a given patient.

Example 8

Sandwich ELISA was Highly Sensitive and Specific to ARL-1 Protein Detection

A sandwich enzyme-linked immunosorbent assay (ELISA) was developed to increase detection sensitivity of ARL-1. Goat polyclonal antisera raised using the whole ARL-1 protein (SEQ ID NO: 5) as an immunogen was developed for use as a capture antibody as described below. Rabbit polyclonal antisera as described in Example 2 against the ARL-1-specific peptide having the sequence of SEQ ID NO:1 was used as a detection antibody.

High binding 96-well plates were coated with 100 μl of 7 μg/ml capture antibody in coating buffer and incubated at 4° C. overnight. The wells were washed 3 times with PBS and blocked with 250 μl blocking buffer (Alpha Diagnostic Intl. Inc., CA) at 37° C. for 2 h. Samples (100 μl each) were added into wells in duplicate. Plates were incubated at 37° C. for 1 h, washed 5 times with PBST (PBS with 0.05% Tween-20), and incubated at 37° C. for 1 h with 1000 per well of biotin-labeled detection antibody diluted at 1:100 with antibody diluent. The plates were washed 5 times with PBST, and incubated at 37° C. for 30 min with 100 μl per well of strepta-vidin-HRP conjugates (1:5000). HRP enzymatic reactions were initiated by adding 100 μl of the substrate TMB (Thermo Scientific, FL) at 37° C. and the reactions continued for 20 min. The reactions were stopped by adding 50 μl stop solution (Alpha Diagnostic Intl. Inc.) and $OD_{450}$ was measured within 30 min using $OD_{620}$ as a reference. Purified ARL-1 or AKR1B1 protein at concentrations of 0, 0.098, 0.195, 0.391, 0.781, 1.5625, 3.125, 6.25, 12.5, and 25 ng/ml was used as standards.

The capture anti-ARL-1 antibody showed strong specificity for ARL-1 and low cross-activity to AKR1B1, a protein that is homologous but not identical to ARL-1 (FIG. 19A) (Cao et al., 1998, *J Biol Chem* 273: 11429-11435). In this system, the detection sensitivity to ARL-1 can be as low as about 0.1 ng/ml, and the cross-reactivity to AKR1B1 remained neglectable at up to 25 ng/ml of AKR1B1 protein (FIG. 19B).

Example 9

ARL-1 was Detected in Tissue Culture Medium of Cancer Cell Lines

Figure 20:
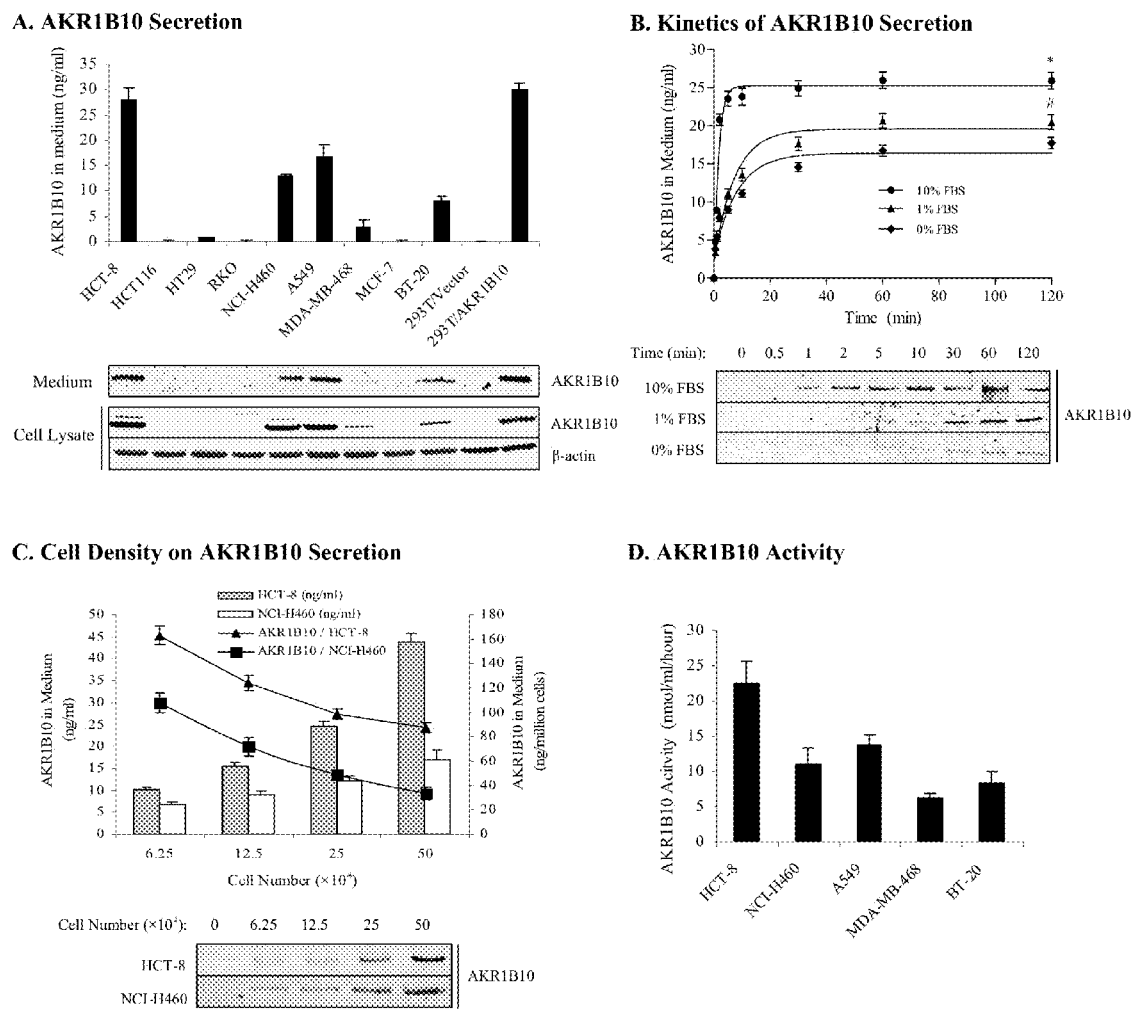
FIG. 20A shows the results of sandwich ELISA and photographs of Western blot analysis of secreted AKR1B10 (ARL-1) in tissue culture medium. HCT-8: colorectal adenocarcinoma, HCT116 and HT29: colorectal carcinoma, RKO: colon carcinoma, H460: large cell lung cancer, A549: lung carcinoma, MDA-MB-468 and MCF-7: breast adenocarcinoma, and BT-20: breast carcinoma.
FIG. 20B shows the results of sandwich ELISA and photographs of Western blot analysis demonstrating the kinetics of AKR1B10 secretion in tissue culture medium of HCT-8 cells incubated in the indicated amounts of FBS.
FIG. 20C shows the results of sandwich ELISA and photographs of Western blot analysis demonstrating the effects of cell density on AKR1B10 secretion: the bar graph shows the effects of cell density on the amount of AKR1B10 secreted into the culture medium, and the line graph shows the effects of cell density on the rate of AKR1B10 secretion.
FIG. 20D shows a bar graph demonstrating that AKR1B10 activity was detected in the tissue culture medium containing secreted AKR1B10 protein.

Using this sandwich ELISA, ARL-1 was also detected in culture medium of several cancer cell lines-HCT-8, NCI-H460, A549, MDA-MB-468, BT-20, HCT116, HT29, RKO, and MCF-7 (2.5×10$^5$ each), which were cultured in RPMI 1640, DMEM, or F-12K medium supplemented with 10% fetal bovine serum (FBS), 2 mM glutamine, 100 U/ml penicillin, and 100 μg/ml streptomycin (Invitrogen, CA) at 37° C. under 5% $CO_2$. ARL-1 in the medium from the indicated cells were cultured overnight in 6-well plates and then fed with 1 ml of serum-free medium for 30 min. Medium was harvested and cell lysates were prepared for sandwich ELISA and Western blot analysis. In addition, 293T cells were transfected with EGFP or EGFP-ARL-1 expression vector for the detection of exogenously expressed ARL-1 (Zu, et al., 2007, *Toxicol Sci.* 97: 562-568). As shown in FIG. 20A, ARL-1 was detected in the medium of HCT-8, NCI-H460, A549, MDA-MB-468, and BT-20, but not in the medium of HCT116, HT29, RKO, and MCF-7. Western blot confirmed the presence of ARL-1 in the medium, which correlated with its expression levels in the corresponding cell lysates (FIG. 20A). In addition, exogenously expressed EGFP-ARL-1 in 293T cells was also secreted (293/AKR1B10, FIG. 20A). These data suggest that ARL-1 is a secretory protein in cancer cells.

The kinetics of ARL-1 secretion was examined. HCT-8 cells (2.5×10$^5$) were cultured in a 6-well plate. On the next day, cells were fed with 1.5 ml of fresh medium containing 0, 1, or 10% FBS. Aliquots of 200 μl of medium were collected and processed for sandwich ELISA and Western blot analysis. The results showed that ARL-1 secretion was stimulated by serum, which was detected in HCT-8 cell cultural medium at 0.5 min and peaked within 2 min after the cells were exposed to fresh medium containing 10% FBS (FIG. 20B). ARL-1 secretion was less efficient when cells were cultured in serum free or low serum medium (FIG. 20B).

Cell density also affected ARL-1 secretion. HCT-8 and NCI-460 cells were incubated in 6-well plates overnight in the presence of fetal bovine serum and then fed with 1 ml of serum-free medium. After 30 min, medium was collected for ELISA and Western blot analysis. As shown in FIG. 20C, the amounts of ARL-1 protein in the medium increased with cell number, but the secretion rates exhibited an inverse correlation with the increase of cell numbers.

The aldehyde reductase activity of secreted ARL-1 was examined as follow. Cells ($2.5 \times 10^5$ in a 60 mm dish,) were incubated overnight in medium containing 10% FBS. The next day, the cells were washed once with PBS, and fed with serum-free medium for 30 min. Medium was collected, centrifuged at 600×g for 10 min to remove cells and debris, and concentrated by 5-fold with dialysis column (Millipore, Calif.). Concentrated medium in the volume of 200 µl was added to a 500 µl aldehyde reductase assay mixture in the presence of a final concentration of 20 mM DL-glyceraldehyde, 135 mM sodium phosphate (pH 7.0), 0.2 mM NADPH, and 50 mM KCl. Reactions were conducted at 35° C. for 30 min. Oxidized NADPH was measured at $OD_{340}$ as an indicator of enzymatic activity. Purified ARL-1 recombinant protein was used as a positive control, and fresh serum-free medium was used as a negative control. Enzymatic activity is expressed as nmol (oxidized NADPH)/ml medium/hour. The data showed that ARL-1 secreted to the culture medium was enzymatically active (FIG. 20D).

Example 10

ARL-1 Protein was Detected in Mature Intestinal Epithelium and Secreted into the Lumen ARL-1 mRNA was detected in the colon and small intestine (Cao et al., 1998, *J Biol Chem* 273: 11429-11435), and the ARL-1 protein was expressed specifically in the mature epithelium of colon and small intestine (FIG. 21A). To understand its secretory behavior in vivo, ARL-1 protein in ileal fluids from 11 individuals was examined. Ileal fluids from normal donors were collected through colonoscopy following the IRB protocol approved by the Springfield Committee for Research Involving Human Subjects (SCRIHS). Informed written consents were obtained from all donors. The ileal fluids were centrifuged at 600×g to remove cells and debris, and clear supernatants were harvested at 10,000×g for 20 min for sandwich ELISA. The results showed that ARL-1 was secreted into lumen at 188.6~535.7 ng/ml of ileal fluids (average: 298.1 ng/ml) (FIG. 21B), indicating that ARL-1 is secreted in the normal intestine, consistent with that in cultured cancer cells.

Example 11

1. ARL-1 Secretion was not Mediated by the Classical Secretion Pathway

Figure 22:
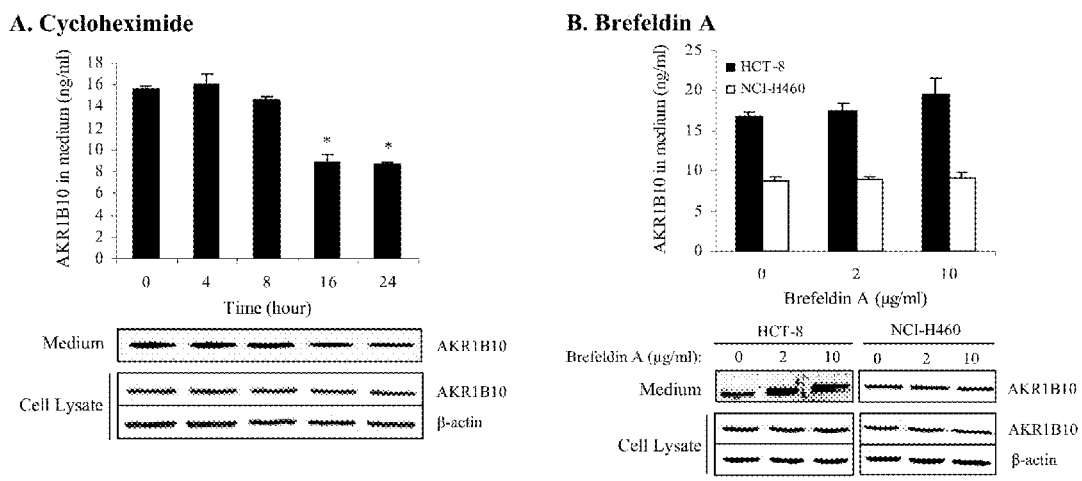
FIG. 22A shows results of sandwich ELISA and Western blot analyses indicating that treatment with the protein synthesis inhibitor cycloheximide for up to 8 hours did not significantly affect secretion of AKR1B10 (ARL-1) protein. * p<0.01 compared to AKR1B10 in medium at 0, 4, 8 hours.
FIG. 22B shows results of sandwich ELISA and Western blot analysis indicating that treatment of brefeldin A, an ER-Golgi protein transport inhibitor, for 6 hours did not significantly affect secretion of AKR1B10.

Soluble proteins are secreted by either the classical or nonclassical pathway (Nickel et al., *Eur J. Biochem.* 270: 2109-2119, 2003). In the classical protein secretion pathway, a secretory protein is translocated by an N-terminal signal peptide into endoplasmic reticulum and Golgi complex concomitant with protein synthesis. Thus, this pathway is affected by inhibitors of protein synthesis and protein transport from ER to Golgi. The amino acid sequence of ARL-1 was analyzed using SignalP 3.0 (http://www.cbs.dtu.dk/services/SignalP/) and no signal peptide was identified (probability=0.000, data not shown). In support of this finding, ARL-1 secretion was found not affected by inhibitors to protein synthesis and ER-Golgi transport pathway. HCT-8 cells ($1.25 \times 10^5$) were cultured in 12-well plates overnight and the next day the cells were exposed to 15 µg/ml of protein synthesis inhibitor cycloheximide in fresh serum-free medium. Medium was collected at different time points for sandwich ELISA and Western blot analysis. As shown in FIG. 22A, ARL-1 secretion was not affected by cycloheximide for up to 8 hours after treatment. Next, the effects of an ER-Golgi pathway inhibitor were examined. HCT-8 and NCI-460 cells ($1.25 \times 10^5$) were cultured in 12-well plates overnight and then exposed to an ER-Golgi protein transport inhibitor brefeldin A at 0, 2, or 10 µg/ml in fresh serum-free medium for 6 hour. Medium was collected for sandwich ELISA and Western blot analysis. As shown in FIG. 22B, ARL-1 was not affected by the ER-Golgi pathway inhibitor. These data suggested that ARL-1 was not secreted via the classical protein secretion pathway. Statistic analysis was performed using Student's t test or Chi square tests, as appropriate, with INSTAT statistical analysis package (GraphPad Software, CA), for statistical significance at $p<0.05$.

2. ARL-1 was Secreted by the Non-Classical Lysosome-Mediated Secretion Pathway

Lysosome-mediated protein secretion was known as a non-classical protein secretion pathway (Johansson, et al., *Exp Hematol,* 37: 969-978, 2009). Whether ARL-1 secretion was mediated by the lysosome-mediated pathway was tested. Lysosomes were isolated as previously described (Andrei et al., *Mol Biol Cell* 10: 1463-1475, 1999). Briefly, $5 \times 10^7$ cells were washed 3 times with PBS, re-suspended in 2 ml PBS containing 10 µg/ml leupeptin and 0.5 mM phenylmethylsulfonyl fluoride, and disrupted by a Dounce homogenizer. Debris and nuclei were removed by centrifugation at 1200×g. The supernatants were subjected to ultracentrifugation at 50,000×g for 10 min at 4° C. The supernatants and lysosomal-containing pellets were separately collected. The pellets were washed with PBS for 3 times and suspended in 15 µl of PBS. For protease protection assays, the resuspended pellets and supernatants (50 µl each) were incubated with 0.0125 mg/ml proteinase K for 30 min on ice, with or without 0.5% Triton X-100, and subjected to Western Blot analysis to detect ARL-1, a lysosome marker Cathepsin D (Cell signaling Technology, CA), and β-actin as loading control. Western blot analysis showed that ARL-1 was present in the lysosomes-containing pellets, protected from proteinase K digestion. This protection was abolished when 0.5% Triton-X100 was added to destroy the lysosomal membranes (FIG. 23A).

Lysosomal-localization of ARL-1 was further proven by a fluorescent protease protection assay in living cells. NCI_H460 cells ($4 \times 10^5$ in 0.5 ml medium) were transfected with EGFP-ARL-1 expression vector and seeded onto polylysine-coated cover slides. After incubation for 36 hr, cells were stained with 100 nM LYSOTRACKER® Red DND-99 (Invitrogen, CA) in serum-free medium for 30 min, followed by staining with 0.5 µg/ml Hoechst for 5 min. Cells were switched to 1 ml of warm Hank's balanced salt solution (HBSS), and images were taken immediately at excitation and emission wavelengths of 577 nm and 590 nm for DND-99, 488 nm and 509 nm for EGFP, and 365 nm and 480 nm for Hoechst, respectively. For protection assays, 1 ml of 2× digitonin (20 µM final concentration) in warm HBSS was added to the cells. After incubation at room temperature for 5 min, cells were treated with trypsin (100 µg/ml) to digest free cytosolic proteins in the presence of digitonin and the fluorescence images were captured. The image of EGFP-ARL-1 staining was merged with the image of LYSOTRACKER® staining. As shown in FIG. 23B, EGFP-ARL-1 staining detected in cellular organelles was protected from protease digestion, and the signals were colocalized with lysosomes staining. The results further proved that ARL-1 was secreted via the lysosome-mediated exocytosis pathway.

3. ARL-1 Secretion was Affected by Temperature, ATP, $Ca^{2+}$ and $NH_4Cl$

Figure 24:
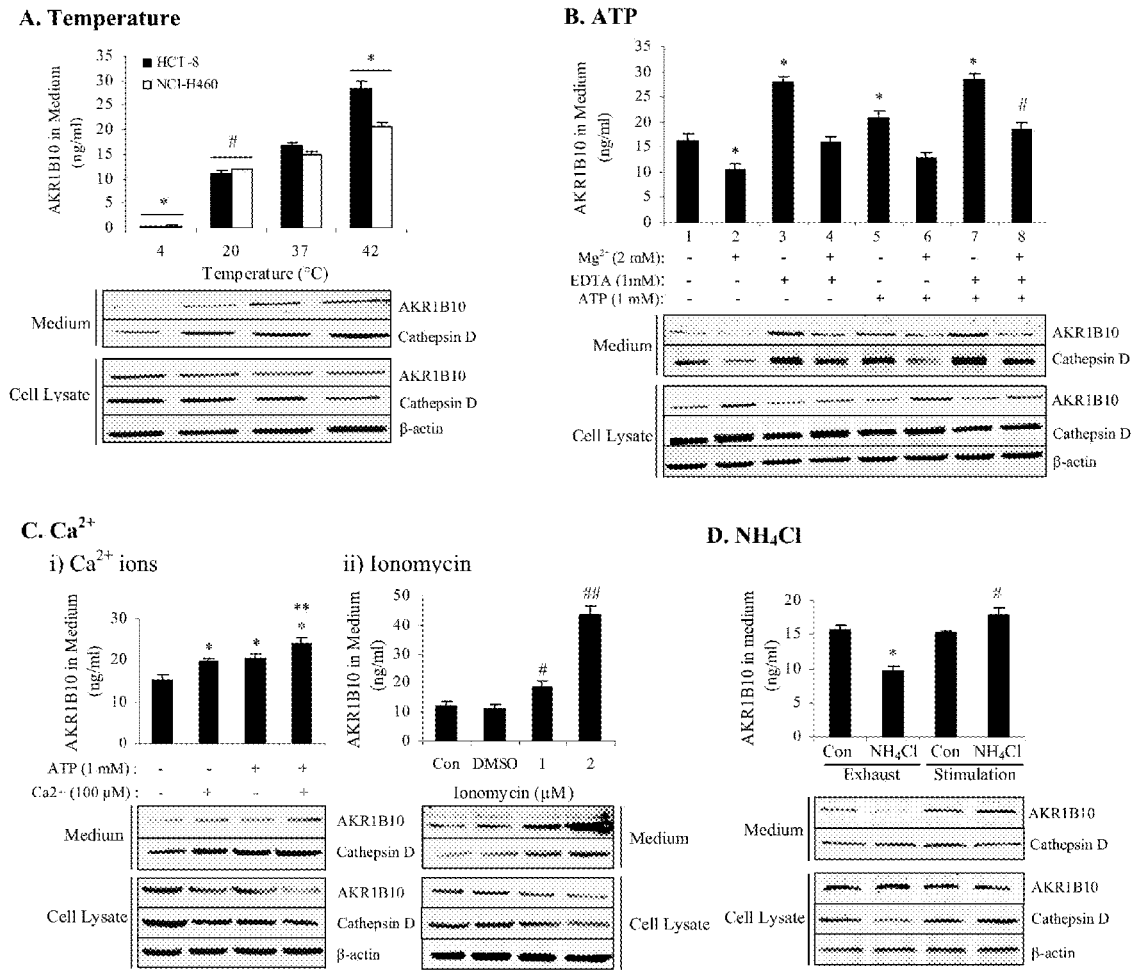
FIGS. 24A-D show results of sandwich ELISA and Western blot analysis showing the effects of temperature (FIG. 24A)* p<0.01 and # p<0.05; ATP (FIG. 24B), * p<0.01 compared to control cells without treatment, # p<0.01 compared to Mg$^{2+}$ alone, or p<0.05 compared Mg$^{2+}$ plus ATP; calcium (FIG. 24C)* p<0.05 compared to control, ** p<0.01 compared to ATP or Ca$^{2+}$ alone, # p<0.05 and ## p<0.01 compared to blank control (con) and DMSO vehicle; and NH$_4$Cl (FIG. 24D)* p<0.01 compared to no NH$_4$Cl control, and # p<0.05 compared to no NH$_4$Cl control, on AKR1B10 (ARL-1) protein secretion via the lysosome-mediated pathway.

The effects of the factors that influence lysosomal exocytosis, e.g., temperature, ATP, $Ca^{2+}$, and $NH_4Cl$, on ARL-1 secretion were examined. The results are shown in FIG. 24A. HCT-8 and NCI-460 cells ($2.5 \times 10^5$ each) were seeded into 6-well plates overnight and then exposed to indicated temperature in serum-free medium for 30 min. The medium was collected for sandwich ELISA ad Western blot analysis. Data showed that in both HCT-8 and NCI-H460 cells ARL-1's secretion was stimulated at 42° C. but almost completely blocked at 4° C., demonstrating that ARL-1 was exocytosed in a temperature-dependent manner (FIG. 24A).

It has been shown that ATP enhances exocytosis by increased membrane fusion or by activating purinergic receptor (Ferrari et al., 1997, *J. Immunol.* 159: 1451-1458; Ferrari et al., 1997 *J Exp Med* 185: 579-582). Purinergic receptors are a family of G protein-coupled P2 receptors. The members of this family of receptors such as P2Y and P2X can be activated by ATP, the activation of which triggers $Ca^{2+}$ mobilization (del Rey et al., 2006, *J Biol Chem* 281: 35147-35155). $Ca^{2+}$ plays a critical role in docking lysosomes to cytoplasm and promoting lysosome exocytosis (Rodriguez et al., 1997, *J Cell Biol* 137: 93-104).

In these studies, HCT-8 cells ($1.25 \times 10^5$) were incubated in 12-well plates overnight and then exposed to 1 mM EDTA and/or 2 mM $Mg^{2+}$ in serum-free medium for 2 hours. At 30 min before harvest, ATP (1 mM) was added and the medium was subjected to sandwich ELISA and Western blot analysis. The results are shown in FIG. 24B. In addition, HCT-8 cells ($1.25 \times 10^5$) were seeded into 12-well plates and exposed to $Ca^{2+}$ ions (100 μM) or ionomycin at 1 or 2 μM in serum-free medium for 30 min and the medium was harvested for sandwich ELISA and Western blot analysis. The results are shown in FIG. 24C. The results demonstrated that ARL-1's secretion was significantly stimulated by ATP (1 mM), $Ca^{2+}$ ions (100 μM), and ionomycin (1-2 μM), a chemical carrier of $Ca^{2+}$ (Mason et al., 1993, *Biochem J*, 296 (Pt 1): 33-39) (FIGS. 24B and C). Further, ATP played a synergistic role in $Ca^{2+}$-mediated stimulation (FIG. 24C). In addition, $Mg^{2+}$ (2 mM) blocked lysosome-mediated ARL-1 secretion by chelating $ATP^{4-}$, an active form of ATP, and the addition of EDTA reversed the inhibition effect of $Mg^{2+}$ (FIG. 24B).

Protein translocation and lysosomal exocytosis is also affected by the luminal pH of lysosomes (Tapper et al., 1990, *Biochem J* 272: 407-414). Reagents that increase lysosomal luminal pH can stimulate exocytosis, but the resulting decrease in ΔpH between cytosol and lysosomal lumen can block protein translocation into lysosomes. $NH_4Cl$ is a lysosomotropic reagent that can increase lysosomal pH and play such a dual role in the lysosome-mediated protein secretion (Andrei et al., 1999, *Mol Biol Cell*, 10: 1463-1475; Ling, et al. 1998, *Kidney Int*, 53: 1706-1712). In this study, serum-free cell culture medium was collected for sandwich ELISA or Western blot analysis where $NH_4Cl$ (50 mM) was either added to the cells for 2 hours before the cells were switched to fresh serum-free medium or $NH_4Cl$ was added to the cells simultaneously with the fresh serum-free medium. The results showed that cells first treated with $NH_4Cl$ (50 mM) for 2 hours exhibited exhausted lysosomal exocytosis, as evidenced by a significant decrease of ARL-1 in freshly fed serum-free medium as compared with control. On the other hand, ARL-1 secretion was increased while $NH_4Cl$ (50 mM) was added simultaneously with the fresh serum-free medium (FIG. 24D).

4. ARL-1 was Translocated into Lysosomes via ABC Transporters

Figure 25:
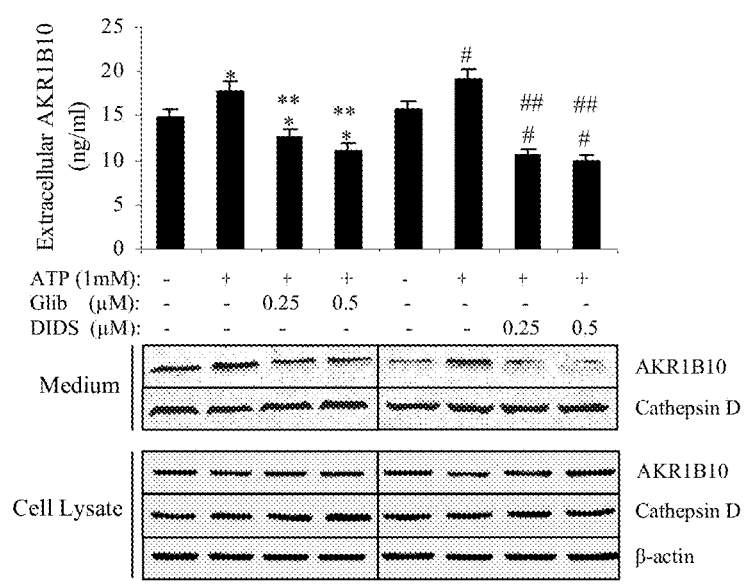
FIG. 25 shows results of sandwich ELISA and Western blot analyses demonstrating the effects of GLIB (glibenclamide) and DIDS (4,4'-diisothiocyanatostilbene-2,2'-disulfonic acid), both ABC transporter inhibitors, on AKR1B10 (ARL-1) secretion.

Proteins that are secreted via the lysosome-mediated pathway are often translocated into lysosomes by the ABC transporters (Hamon et al., *Blood* 90: 2911-2915, 1997). To understand the transmembrane mechanism of ARL-1, HCT-8 cells ($1.25 \times 10^5$) were cultured in 12-well plates overnight and then exposed to ABC transporter inhibitor GLIB (glibenclamide) or DIDS (4,4'-diisothiocyanatostilbene-2,2'-disulfonic acid) (Sigma, Mo.) in serum-free medium for 2 hours. ATP (1 mM) was added 30 min before harvest. Medium and cells were collected for sandwich ELISA and Western blot analysis. The results showed that GLIB and DIDS both suppressed ARL-1 secretion (FIG. 25), suggesting that the ABC transporter played a role in the entry of ARL-1 into lysosomes.

Example 12

ARL-1 was Detected in the Serum of Breast Cancer Patients

Figure 26:
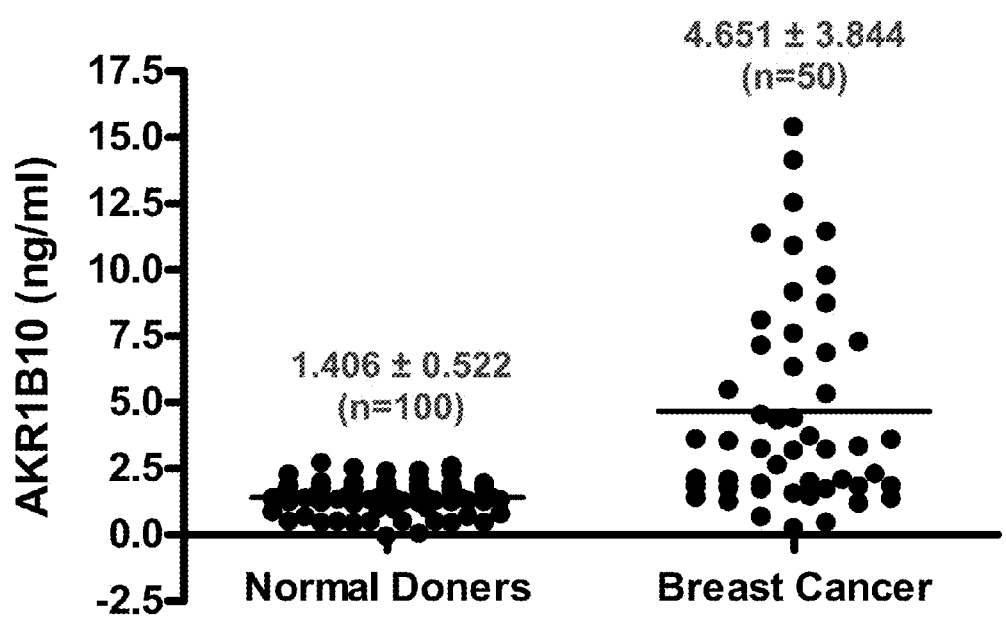
FIG. 26 is a graph showing the amount of AKR1B10 (ARL-1) detected in the serum of normal donors and breast cancer patients.

Data above demonstrated that ARL-1 was secreted into the culture medium in cancer cell culture. ARL-1 was detected in serum of a population of breast cancer patients, as shown in FIG. 26.

It should be understood that the foregoing disclosure emphasizes certain specific embodiments of the invention and that all modifications or alternatives equivalent thereto are within the spirit and scope of the invention as set forth in the appended claims.

I claim:

1. A method for detecting breast cancer or prostate cancer or a precancerous lesion of the breast or prostate, comprising:
   contacting, in vitro, a breast tissue sample or a prostate tissue sample from a human with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;
   detecting expression of the ARL-1 protein in the sample based on said contacting step;
   comparing expression of the ARL-1 protein, detected in said detecting step, with expression of the ARL-1 protein in a normal breast tissue sample or a normal prostate tissue sample; and
   detecting breast cancer or prostate cancer or precancerous lesion of the breast or the prostate when expression of detected ARL-1 protein is greater than expression of detected ARL-1 protein in said normal breast tissue sample or said normal prostate tissue sample.

2. A method of claim 1, wherein expression of the ARL-1 protein is detected by in situ immunohistochemistry or western blot analysis.

3. A method for identifying a human at risk for developing breast cancer or prostate cancer, comprising:
   contacting, in vitro, a non-cancerous breast tissue sample or a non-cancerous prostate tissue sample from the human with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;
   detecting expression of ARL-1 protein in the sample based on said contacting step; and
   identifying said human at risk for developing breast cancer or prostate cancer when expression of ARL-1 protein detected in the non-cancerous breast or prostate sample is greater than expression of ARL-1 protein in a normal breast tissue sample or prostate tissue sample.

4. A method of claim 3, wherein expression of the ARL-1 protein is detected by in situ immunohistochemistry or western blot analysis.

5. A method for identifying a human at risk for recurrence of breast cancer or prostate cancer, comprising:
   contacting, in vitro, a breast tissue sample or a prostate tissue sample from a human who is in remission of breast cancer or prostate cancer with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;

detecting expression of ARL-1 protein in the sample based on said contacting step;

identifying said human at risk for recurrence of breast cancer or prostate cancer when expression of ARL-1 protein in said breast or prostate tissue sample is greater than expression of ARL-1 protein a normal breast or prostate tissue sample.

6. The method of claim 5, wherein the expression of the ARL-1 protein is detected by in situ immunohistochemistry or western blot analysis.

7. A method for diagnosing cancer or a precancerous lesion thereof in a human, wherein the cancer is breast cancer, lung cancer, liver cancer, or prostate cancer, comprising:

contacting, in vitro, a bodily fluid sample from a human with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;

detecting amounts or concentrations of ARL-1 protein in the sample based on said contacting step; and diagnosing the cancer or the precancerous lesion thereof in the human when the amounts or concentrations of detected ARL-1 protein is greater than the amounts or concentrations of ARL-1 protein in the sample from the normal human; and subjecting the human to further testing to confirm the presence of the cancer or the precancerous lesion thereof in the human.

8. The method of claim 7, wherein the bodily fluid is blood plasma, serum, lymph, urine, breast secretion, breast milk, prostate fluid or sputa.

9. The method of claim 7, wherein the further testing comprises obtaining a tissue sample from the human for analysis, wherein the analysis comprises assaying the tissue sample to detect expression of the ARL-1 protein, wherein cancer or a precancerous lesion thereof is identified when expression of the ARL-1 protein ARL-1 expression in the tissue sample from the human is greater than expression of the ARL-1 protein in a normal tissue sample, wherein the tissue sample is a breast tissue, lung tissue, liver tissue or prostate tissue sample.

10. The method of claim 7, wherein the amounts or concentrations of the ARL-1 protein is detected by western blot analysis, radioimmunoassay or enzyme-linked immunosorbent assay (ELISA).

11. A method for identifying cancer metastasis or cancer recurrence of breast cancer, lung cancer, liver cancer or prostate cancer, comprising contacting, in vitro, a bodily fluid sample from a human who had primary tumor of breast, lung, liver or prostate and is in remission of the primary tumor with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;

detecting amounts or concentrations of ARL-1 protein in the sample based on said contacting step; and identifying the cancer metastasis or recurrence when the amounts or concentrations of detected ARL-1 protein in said bodily fluid sample is greater than the amounts or concentrations of ARL-1 protein in a sample from a normal human.

12. The method of claim 11, wherein the bodily fluid is blood plasma, serum, lymph, urine, breast secretion, breast milk, prostate fluid or sputa.

13. The method of claim 11, wherein the cancer metastasis is breast cancer metastasis.

14. The method of claim 11, wherein the amounts or concentrations of ARL-1 protein is detected by western blot analysis, radioimmunoassay or enzyme-linked immunosorbent assay (ELISA).

15. A method for identifying a human having cancer metastasis or at risk for cancer metastasis of breast cancer, lung cancer, liver cancer or prostate cancer, comprising:

contacting, in vitro, a bodily fluid sample from a human who had breast cancer, lung cancer, liver cancer or prostate cancer, and who is in remission of said cancer with one or more isolated antibodies or antigen-binding fragments thereof that specifically bind to human reductase-like-1 (ARL-1) protein, wherein the one or more isolated antibodies or antigen-binding fragments thereof comprise an isolated antibody produced by immunizing an animal using a peptide antigen with the amino acid sequence identified by SEQ ID NO:1, wherein the antibody is a monoclonal antibody;

detecting amounts or concentrations of ARL-1 protein in the sample based on said contacting step; and identifying the human as having cancer metastasis or at risk for cancer metastasis when the amounts or concentrations of ARL-1 protein detected in the bodily fluid sample is greater than the amounts or concentrations of ARL-1 protein in a bodily fluid sample from a normal individual.

16. The method of claim 15 wherein the amounts or concentrations of ARL-1 protein is detected by western blot analysis, radioimmunoassay or enzyme-linked immunosorbent assay (ELISA).

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Synthetic; Peptide used as specific antigen to
      raise anti-ARL-1 antibodies

<400> SEQUENCE: 1
```

```
Asp Asp Lys Gly Asn Ala Ile Gly Gly Lys Ala Thr Phe Leu Cys
1               5                   10                  15

<210> SEQ ID NO 2
<211> LENGTH: 21
<212> TYPE: DNA
<213> ORGANISM: Artificial Sequence
<220> FEATURE:
<223> OTHER INFORMATION: Synthetic; siRNA targeted to coding region of
      ARL-1

<400> SEQUENCE: 2
gcaaguugug gcccacuuut t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic; siRNA targeted to 3' untranslated
      region of ARL-1

<400> SEQUENCE: 3
cgagaaucga ggugcuguut t                                              21

<210> SEQ ID NO 4
<211> LENGTH: 1337
<212> TYPE: DNA
<213> ORGANISM: Homo sapiens
<220> FEATURE:
<221> NAME/KEY: CDS
<222> LOCATION: (70)..(1020)
<223> OTHER INFORMATION: Human ARL-1 gene

<400> SEQUENCE: 4
caaaaacagc aacagaaagc aggacgtgag acttctacct gctcactcag aatcatttct    60 gcaccaacc atg gcc acg ttt gtg gag ctc agt acc aaa gcc aag atg ccc   111
           Met Ala Thr Phe Val Glu Leu Ser Thr Lys Ala Lys Met Pro
            1               5                   10 att gtg ggc ctg ggc act tgg aag tct cct ctc ggc aaa gtg aaa gaa    159
Ile Val Gly Leu Gly Thr Trp Lys Ser Pro Leu Gly Lys Val Lys Glu
 15              20                  25                  30 gca gtg aag gtg gcc att gat gca gga tat cgg cac att gac tgt gcc    207
Ala Val Lys Val Ala Ile Asp Ala Gly Tyr Arg His Ile Asp Cys Ala
                 35                  40                  45 tat gtc tat cag aat gaa cat gaa gtg ggg gaa gcc atc caa gag aag    255
Tyr Val Tyr Gln Asn Glu His Glu Val Gly Glu Ala Ile Gln Glu Lys
             50                  55                  60 atc caa gag aag gct gtg aag cgg gag gac ctg ttc atc gtc agc aag    303
Ile Gln Glu Lys Ala Val Lys Arg Glu Asp Leu Phe Ile Val Ser Lys
         65                  70                  75 ttg tgg ccc act ttc ttt gag aga ccc ctt gtg agg aaa gcc ttt gag    351
Leu Trp Pro Thr Phe Phe Glu Arg Pro Leu Val Arg Lys Ala Phe Glu
     80                  85                  90 aag acc ctc aag gac ctg aag ctg agc tat ctg gac gtc tat ctt att    399
Lys Thr Leu Lys Asp Leu Lys Leu Ser Tyr Leu Asp Val Tyr Leu Ile
 95                 100                 105                 110 cac tgg cca cag gga ttc aag tct ggg gat gac ctt ttc ccc aaa gat    447
His Trp Pro Gln Gly Phe Lys Ser Gly Asp Asp Leu Phe Pro Lys Asp
                115                 120                 125 gat aaa ggt aat gcc atc ggt gga aaa gca acg ttc ttg gat gcc tgg    495
Asp Lys Gly Asn Ala Ile Gly Gly Lys Ala Thr Phe Leu Asp Ala Trp
            130                 135                 140 gag gcc atg gag gag ctg gtg gat gag ggg ctg gtg aaa gcc ctt ggg    543
```

-continued

| | | |
|---|---|---|
| Glu Ala Met Glu Glu Leu Val Asp Glu Gly Leu Val Lys Ala Leu Gly<br>    145                 150                 155 | | |
| gtc tcc aat ttc agc cac ttc cag atc gag aag ctc ttg aac aaa cct<br>Val Ser Asn Phe Ser His Phe Gln Ile Glu Lys Leu Leu Asn Lys Pro<br>160                 165                 170 | 591 | |
| gga ctg aaa tat aaa cca gtg act aac cag gtt gag tgt cac cca tac<br>Gly Leu Lys Tyr Lys Pro Val Thr Asn Gln Val Glu Cys His Pro Tyr<br>175                 180                 185                 190 | 639 | |
| ctc acg cag gag aaa ctg atc cag tac tgc cac tcc aag ggc atc acc<br>Leu Thr Gln Glu Lys Leu Ile Gln Tyr Cys His Ser Lys Gly Ile Thr<br>            195                 200                 205 | 687 | |
| gtt acg gcc tac agc ccc ctg ggc tct ccg gat aga cct tgg gcc aag<br>Val Thr Ala Tyr Ser Pro Leu Gly Ser Pro Asp Arg Pro Trp Ala Lys<br>        210                 215                 220 | 735 | |
| cca gaa gac cct tcc ctg ctg gag gat ccc aag att aag gag att gct<br>Pro Glu Asp Pro Ser Leu Leu Glu Asp Pro Lys Ile Lys Glu Ile Ala<br>    225                 230                 235 | 783 | |
| gca aag cac aaa aaa acc gca gcc cag gtt ctg atc cgt ttc cat atc<br>Ala Lys His Lys Lys Thr Ala Ala Gln Val Leu Ile Arg Phe His Ile<br>240                 245                 250 | 831 | |
| cag agg aat gtg att gtc atc ccc aag tct gtg aca cca gca cgc att<br>Gln Arg Asn Val Ile Val Ile Pro Lys Ser Val Thr Pro Ala Arg Ile<br>255                 260                 265                 270 | 879 | |
| gtt gag aac att cag gtc ttt gac ttt aaa ttg agt gat gag gag atg<br>Val Glu Asn Ile Gln Val Phe Asp Phe Lys Leu Ser Asp Glu Glu Met<br>            275                 280                 285 | 927 | |
| gca acc ata ctc agc ttc aac aga aac tgg agg gcc tgt aac gtg ttg<br>Ala Thr Ile Leu Ser Phe Asn Arg Asn Trp Arg Ala Cys Asn Val Leu<br>        290                 295                 300 | 975 | |
| caa tcc tct cat ttg gaa gac tat ccc ttc gat gca gaa tat tga<br>Gln Ser Ser His Leu Glu Asp Tyr Pro Phe Asp Ala Glu Tyr<br>    305                 310                 315 | 1020 | |
| ggttgaatct cctggtgaga ttatacagga gattctcttt cttcgctgaa gtgtgactac | 1080 | |
| ctccactcat gtcccatttt agccaagctt atttaagatc acagtgaact tagtcctgtt | 1140 | |
| atagacgaga atcgaggtgc tgttttagac atttatttct gtatgttcaa ctaggatcag | 1200 | |
| aatatcacag aaaagcatgg cttgaataag gaaatgacaa ttttttccac ttatctgatc | 1260 | |
| agaacaaatg tttattaagc atcagaaact ctgccaacac tgaggatgta aagatcaata | 1320 | |
| aaaaaaataa taatcat | 1337 | |

<210> SEQ ID NO 5
<211> LENGTH: 316
<212> TYPE: PRT
<213> ORGANISM: Homo sapiens

<400> SEQUENCE: 5

Met Ala Thr Phe Val Glu Leu Ser Thr Lys Ala Lys Met Pro Ile Val
1               5                   10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
        35                  40                  45

Tyr Gln Asn Glu His Glu Val Gly Glu Ala Ile Gln Glu Lys Ile Gln
    50                  55                  60

Glu Lys Ala Val Lys Arg Glu Asp Leu Phe Ile Val Ser Lys Leu Trp
65                  70                  75                  80

Pro Thr Phe Phe Glu Arg Pro Leu Val Arg Lys Ala Phe Glu Lys Thr
                85                  90                  95

-continued

```
Leu Lys Asp Leu Lys Leu Ser Tyr Leu Asp Val Tyr Leu Ile His Trp
            100                 105                 110

Pro Gln Gly Phe Lys Ser Gly Asp Asp Leu Phe Pro Lys Asp Asp Lys
            115                 120                 125

Gly Asn Ala Ile Gly Gly Lys Ala Thr Phe Leu Asp Ala Trp Glu Ala
            130                 135                 140

Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
            195                 200                 205

Ala Tyr Ser Pro Leu Gly Ser Pro Asp Arg Pro Trp Ala Lys Pro Glu
210                 215                 220

Asp Pro Ser Leu Leu Glu Asp Pro Lys Ile Lys Glu Ile Ala Ala Lys
225                 230                 235                 240

His Lys Lys Thr Ala Ala Gln Val Leu Ile Arg Phe His Ile Gln Arg
            245                 250                 255

Asn Val Ile Val Ile Pro Lys Ser Val Thr Pro Ala Arg Ile Val Glu
            260                 265                 270

Asn Ile Gln Val Phe Asp Phe Lys Leu Ser Asp Glu Glu Met Ala Thr
            275                 280                 285

Ile Leu Ser Phe Asn Arg Asn Trp Arg Ala Cys Asn Val Leu Gln Ser
            290                 295                 300

Ser His Leu Glu Asp Tyr Pro Phe Asp Ala Glu Tyr
305                 310                 315
```